US010765925B2

(12) United States Patent
Coza et al.

(10) Patent No.: US 10,765,925 B2
(45) Date of Patent: *Sep. 8, 2020

(54) SPORTS BALL ATHLETIC ACTIVITY MONITORING METHODS AND SYSTEMS

(71) Applicant: adidas AG, Herzogenaurach (DE)

(72) Inventors: Aurel Coza, Portland, OR (US); Christian Dibenedetto, Portland, OR (US)

(73) Assignee: adidas AG, Herzogenaurach (DE)

( * ) Notice: Subject to any disclaimer, the term of this patent is extended or adjusted under 35 U.S.C. 154(b) by 126 days.

This patent is subject to a terminal disclaimer.

(21) Appl. No.: 15/848,296

(22) Filed: Dec. 20, 2017

(65) Prior Publication Data

US 2018/0117436 A1    May 3, 2018

Related U.S. Application Data

(63) Continuation of application No. 14/120,272, filed on May 14, 2014, now Pat. No. 9,849,361.

(51) Int. Cl.
*A63B 69/00* (2006.01)
*A63B 71/06* (2006.01)
*A63B 24/00* (2006.01)
*G09B 19/00* (2006.01)

(52) U.S. Cl.
CPC ........ *A63B 69/002* (2013.01); *A63B 24/0062* (2013.01); *A63B 71/0619* (2013.01); *G09B 19/0038* (2013.01); *A63B 2208/0204* (2013.01); *A63B 2220/24* (2013.01); *A63B 2220/30* (2013.01); *A63B 2220/35* (2013.01); *A63B 2220/40* (2013.01)

(58) Field of Classification Search
CPC .............. A63B 69/002; A63B 24/0062; A63B 71/0619; A63B 2208/0204; A63B 2220/24; A63B 2220/30; A63B 2220/35; A63B 2220/40; G09B 19/0038
See application file for complete search history.

(56) References Cited

U.S. PATENT DOCUMENTS

2005/0233815 A1*  10/2005  McCreary .......... A63B 24/0021
                                                        473/131

* cited by examiner

*Primary Examiner* — Tramar Y Harper
*Assistant Examiner* — Jeffrey K Wong
(74) *Attorney, Agent, or Firm* — Sterne, Kessler, Goldstein & Fox P.L.L.C.

(57) ABSTRACT

A method for monitoring the motion of a sport ball that has been impacted by an individual during the course of an athletic activity includes the steps of a portable electronic device wirelessly receiving motion data from the sport ball, and the portable electronic device determining a point of impact based on the motion data, wherein the point of impact includes a location on a surface of the sport ball where the impact occurred.

17 Claims, 50 Drawing Sheets

Kick It

Position Ball

602

Tap when ready to kick

Select Kicking Foot

604

610  ←

608  Ball Strike

< Challenges    Results smart_ball bend challenge

Tom wins!

Fig. 44

< Back    Record Book

600  ★ Favorite Kicks         >

Top Power Kicks          >

Top Spin Kicks           >

Top Knuckle Ball Kicks   >

Fig. 46

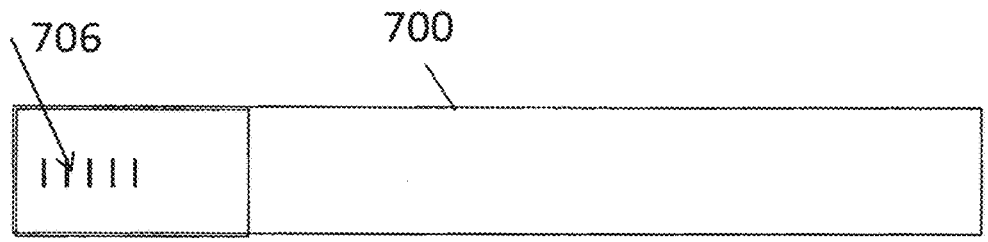
Fig. 50A
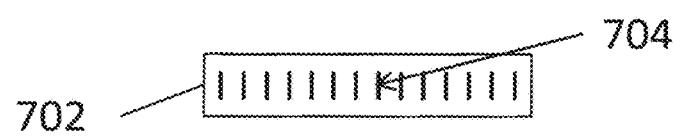
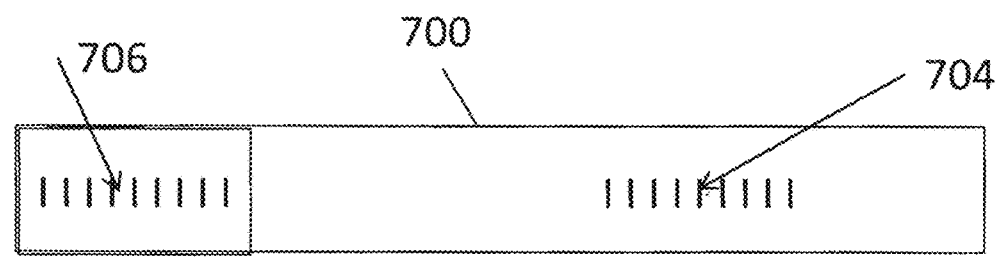
Fig. 50B
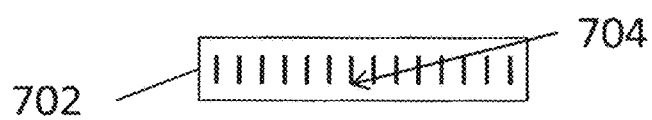
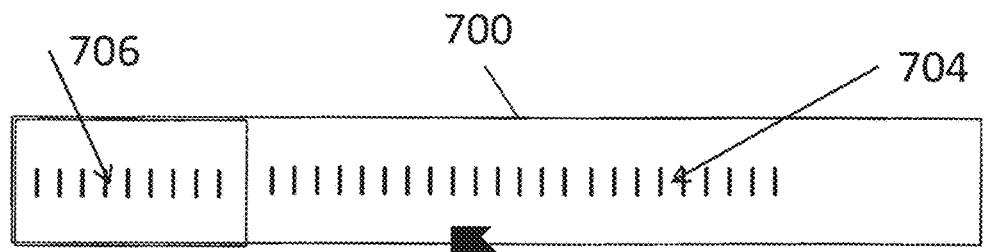
Fig. 50C
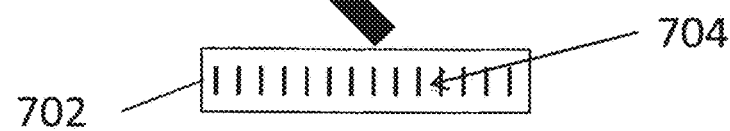

SPORTS BALL ATHLETIC ACTIVITY MONITORING METHODS AND SYSTEMS

CROSS-REFERENCE TO RELATED APPLICATIONS

The present application is a continuation of U.S. patent application Ser. No. 14/120,272, filed May 14, 2014, which is incorporated herein by reference in its entirety.

FIELD OF THE INVENTION

Embodiments of the present invention generally relate to methods and systems for monitoring the motion of a piece of athletic equipment during an athletic activity. More particularly, embodiments of the present invention relate to methods and systems for monitoring the motion of a sport ball used by an individual during an athletic activity.

BACKGROUND OF THE INVENTION

Athletic activity is important to maintaining a healthy lifestyle and is a source of entertainment for many people. Some individuals prefer to engage in team athletic activities such as, for example, soccer or basketball, while other individuals prefer to engage in individual athletic activities such as, for example, running or skiing. Regardless of whether the activity is a team or individual activity, it is common for individuals to participate in both competitive sessions, such as a soccer match or a running race, and more informal training sessions such as conducting soccer drills or running interval sprints.

Technology has resulted in the development of athletic monitoring devices that are capable of recording information about an individual's performance during an athletic activity using sensors, and in some cases providing feedback about the individual's performance. Some portable athletic monitoring devices employ sensors attached to a piece of athletic equipment. Such sensors may be capable of measuring various parameters associated with the individual's physical activity, such as motion parameters.

Many existing athletic equipment monitoring devices are not portable and thus are not suitable for monitoring in many real world competitive or training sessions. Even those that are portable are often too heavy or lack sufficient battery and/or processing power to be used for extended periods under rigorous competitive or training conditions. In addition, while some existing athletic equipment monitoring devices are capable of making relatively simple motion or other performance determinations, more advanced determinations are often not possible or suffer from accuracy issues. Finally, the performance feedback provided by existing devices to individuals often fails to provide these individuals with quick, accurate, insightful information that would enable them to easily compare past performances, develop strategies for improving future performances, visualize performances, or select new training regimens or athletic equipment.

BRIEF SUMMARY OF THE INVENTION

What is needed are new athletic equipment monitoring methods and systems having improved capabilities, thus offering individuals engaged in athletic activities better tools to assess their activities. At least some of the embodiments of the present invention satisfy the above needs and provide further related advantages as will be made apparent by the description that follows.

Embodiments of the present invention relate to a method for monitoring the motion of a sport ball that has been impacted by an individual during the course of an athletic activity includes the steps of a portable electronic device wirelessly receiving motion data from the sport ball, and the portable electronic device determining a point of impact based on the motion data, wherein the point of impact includes the location on a surface of the sport ball where the impact occurred.

Embodiments of the present invention also relate to a computer program product including a non-transitory computer readable medium having computer program logic recorded thereon, for use in monitoring the motion of a sport ball that has been impacted by an individual during the course of an athletic activity, that, when executed by one or more processors of a portable electronic device, is capable of causing the portable electronic device to wirelessly receive motion data from the sport ball, and determine a point of impact based on the motion data, wherein the point of impact includes the location on a surface of the sport ball where the impact occurred.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

FIG. 44 is a graphical user interface for a sport ball motion monitoring application according to an embodiment of the present invention.

FIG. 46 is a graphical user interface for a sport ball motion monitoring application according to an embodiment of the present invention.

Figure 1:
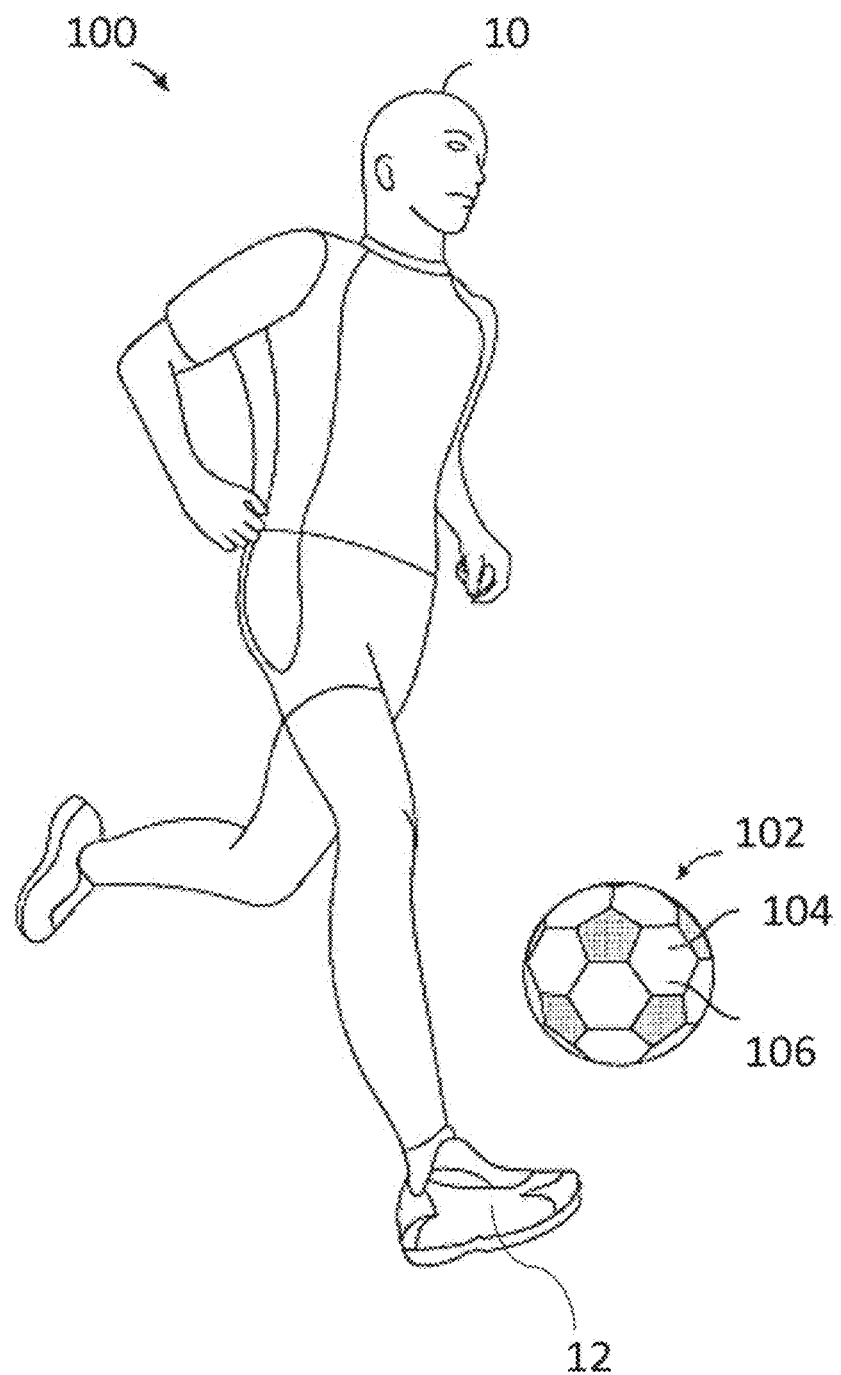
FIG. 1 is an illustration of an individual using a motion monitoring system according to an embodiment of the present invention.

FIGS. 50A though 50C are illustrations of a compression algorithm functionality according to an embodiment of the present invention.

DETAILED DESCRIPTION OF THE INVENTION

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The present invention generally relates to methods and systems for monitoring the motion of a piece of athletic equipment during an athletic activity. More particularly, embodiments of the present invention relate to methods and systems for monitoring the motion of a sport ball used by an individual during an athletic activity. An individual engaged in an athletic activity (or another interested person such as a coach, teammate, or spectator) may desire to obtain information about the motion of a piece of the individual's athletic equipment during the course of the athletic activity. Some embodiments of the present invention further relate to a sport ball motion monitoring system portable electronic device software application.

For example, if the individual is participating in an activity that involves the use of a sport ball, such as playing in a soccer (i.e., football) match, it may be desirable, for example, to be able to determine the various launch angles at which the soccer ball (i.e., football) was kicked by the individual, to be able to determine the rate of rotation of the soccer ball after it was kicked by the individual, to be able to determine the peak speeds that the soccer ball was traveling at after being kicked by the individual, or to be able to determine the specific locations on the surface of the ball where the individual's foot struck the ball when kicking the ball.

In an embodiment, the movement of a plurality of pieces of athletic equipment used by a plurality of individuals engaged in an athletic activity (e.g., teammates or opponents in a team sport) may be monitored. In some embodiments, real-time monitoring and/or feedback may be provided, while in other embodiments post-activity feedback may be provided. In some embodiments, feedback may be provided by an athletic equipment motion monitoring system portable electronic device software application.

By using an athletic activity monitoring system including one or more portable sensors, embodiments of the present invention described below may advantageously enable an individual (or their coach, teammate, or a spectator) to obtain this or other information about the motion of a piece of the individual's athletic equipment during the course of the athletic activity. Data obtained by sensors may be processed in a variety of ways to yield useful information about the motion of an object of interest during the activity. In some embodiments, sensor data may be processed to monitor changes in the spatial orientation (i.e., changes in the position and/or rotation, relative to a specific location on the Earth or other point of reference) of a piece of the individual's athletic equipment. In other embodiment, sensor data may be processed to by reference to a predetermined correlation between movement data and an activity metric stored in a data structure.

In one embodiment, information about the motion of a piece of the individual's athletic equipment may be used, for example, to provide coaching to the individual about how their movements could be improved, or as a check on the accuracy of a referee, umpire, or other athletic competition judge's judgment related to the movement of the athletic equipment.

I. Exemplary Embodiments of Components of Motion Monitoring Systems

FIG. 1 is an illustration of an individual 10 using a motion monitoring system 100 according to an embodiment of the present invention. The individual 10 may desire to obtain information about the motion of a piece of the individual's 10 athletic equipment 104 during the course of the athletic activity using motion monitoring systems 100 according to the present invention.

Motion monitoring systems 100 according to embodiments of the present invention may be suitable for use by individuals 10 for team or individual athletic activities and for competitive and informal training sessions. For example, motion monitoring systems 100 according to embodiments of the present invention may be suitable for use by individuals 10 engaged in athletic activities such as baseball, basketball, bowling, boxing, cricket, cycling, football (i.e., American football), golf, hockey, lacrosse, rowing, rugby, running, skateboarding, skiing, soccer (i.e., football), surfing, swimming, table tennis, tennis, or volleyball, or during training sessions related thereto.

Motion monitoring systems 100 according to embodiments of the present invention may include a sensor module 102. The sensor module 102 may include one or more sensors, and may be physically coupled to a piece of athletic equipment 104 during an athletic activity conducted by an individual 10. As explained in further detail below, the sensor module 102 may be used to monitor changes in the spatial orientation of a piece of athletic equipment 104 in some embodiments, while the sensor module 102 may be used in combination with predetermined correlation data stored in a data structure to determine a correlation between equipment 104 movement data and an activity metric in other embodiments.

In some embodiments, as illustrated in FIG. 1, the sensor module 102 may be physically coupled to the piece of athletic equipment 104. In the illustrated embodiment, the sensor module 102 is physically coupled to a piece of athletic equipment 104 that is a soccer ball 106 that the individual 10 is kicking with their foot 12. In other embodiments, the sensor module 102 may be configured to be physically coupled to other pieces of athletic equipment 104 such as, for example, any type of sport ball 106, any type of sport "stick" (e.g., a baseball bat, hockey stick, golf club, table tennis paddle, or tennis racquet), a sport glove, a bicycle, an oar, a shoe, a boot, a ski, a hat or cap, a skateboard, a surfboard, or a pair of glasses or goggles. In some embodiments, multiple sensor modules 102 can be coupled to the same piece of athletic equipment 104, or multiple separate pieces of hardware may perform the function of a single sensor module 102 to achieve the functions specified herein.

A sport ball 106 may include an outer layer enclosing a hollow void of the sport ball 106. The outer layer may be stitched, bonded, and/or glued together from panels of leather or plastic and laced to allow access to an internal air bladder, if necessary. In other embodiments, the sport ball 106 may be a non-hollow sport ball 106 (e.g., a baseball, bowling ball, or golf ball) including a single, solid layer or multiple different layers.

The sensor module 102 may be physically coupled to the piece of athletic equipment 104 by a variety of coupling means depending on the nature of the piece of athletic equipment 104 and the athletic activity. For example, the sensor module 102 may be physically coupled to a sport ball 106 by being attached to the exterior of the sport ball 106, by being attached to an interior surface of a hollow sport ball 106, by being suspended by a suspension system in the interior of a hollow sport ball 106, or by being integrated into the outer layer or other layer of a multi-layer sport ball 106.

Figure 2:
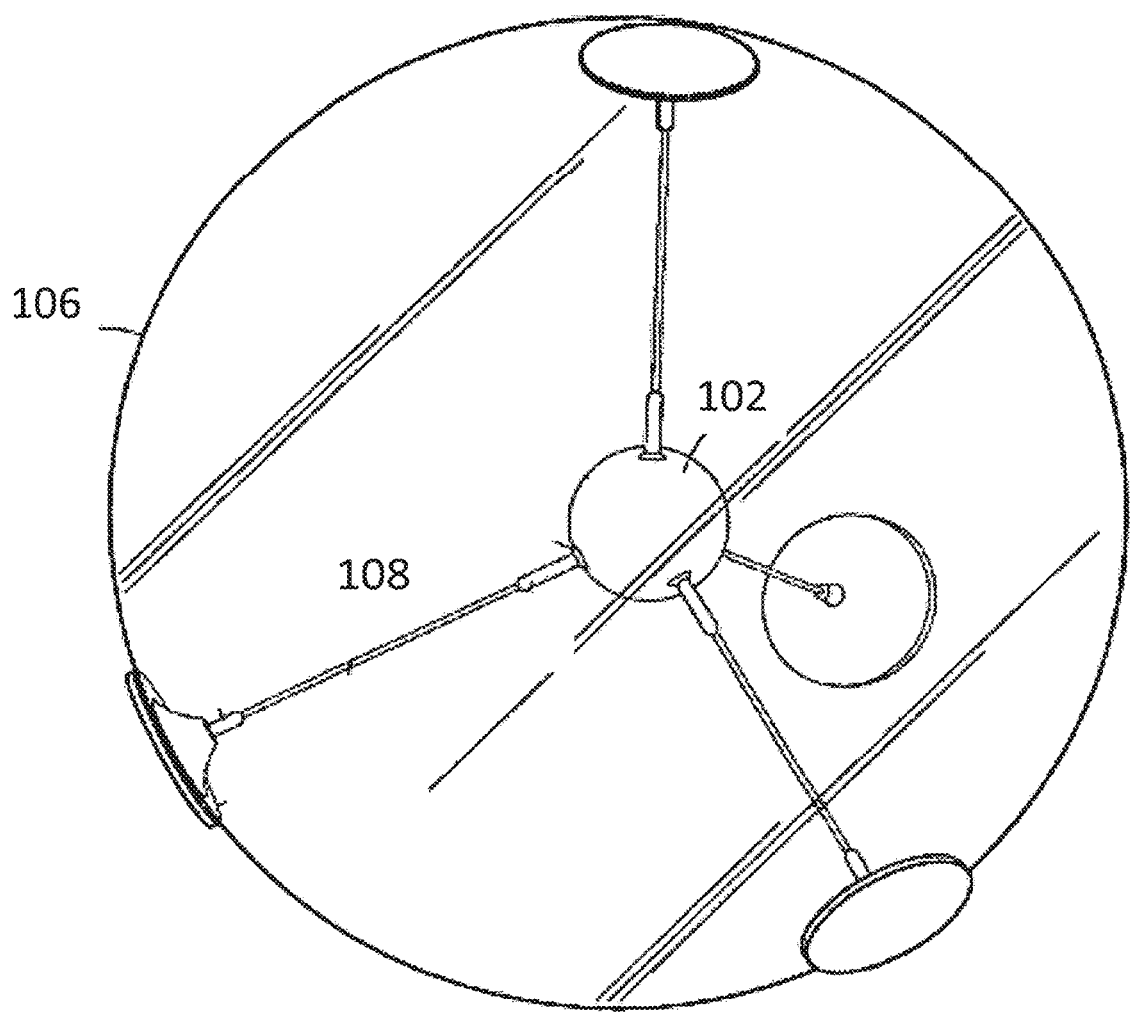
FIG. 2 is an illustration of a sport ball according to an embodiment of the present invention.

For example, FIG. 2 illustrates a sensor module 102 suspended by several cables 108 in the interior of a hollow soccer ball 106. This arrangement allows for the sensor module to be which is shock-mounted and protected at the center of the sport ball 106. Also, the sensor module 102 may be physically coupled to a non-hollow sport ball 106 (e.g., a baseball, bowling ball, or golf ball) by, for example, being attached to the exterior of the sport ball 106, being integrated between layers of a multi-layer sport ball 106, by being embedded in a solid portion of the sport ball 106. Exemplary techniques that can be employed to mount sensor module 102 to sport ball 106 are disclosed in commonly owned U.S. Pat. No. 7,740,551, filed Nov. 18, 2009, and commonly owned U.S. Pat. No. 8,517,869, also filed Nov. 18, 2009, the entireties of which are incorporated herein by reference thereto.

In some embodiments, the sensor module 102 may be attached to or incorporated into a sport ball 106 prior to sale to an individual 10, while in other embodiments the individual 10 may later insert the sensor module 102 after purchasing the sport ball 106.

As further examples, the sensor module 102 may be releasably or non-releasably physically coupled to a sport "stick" by being wrapped around a portion of the sport stick, by being clipped to a portion of the sport stick, by being attached to an exterior surface of the sport stick, by being attached to an interior surface of a hollow or non-hollow sport stick, by being suspended by a suspension system in the interior of a hollow sport stick, or by being integrated into the wall or other layer of a multi-layer or composite sport stick. The sensor module 102 may be physically coupled to the piece of athletic equipment 104 by a variety of coupling means such as, for example, straps, adhesives, or by being integrated into the piece of athletic equipment 104. In one embodiment, the sensor module 102 may be releasably or non-releasably physically coupled to a piece of athletic equipment 104, such as a sport stick, be being incorporated into a sleeve that is secured about the outside of a piece of athletic equipment 104, such as a sport stick or a handle thereof.

Figure 3:
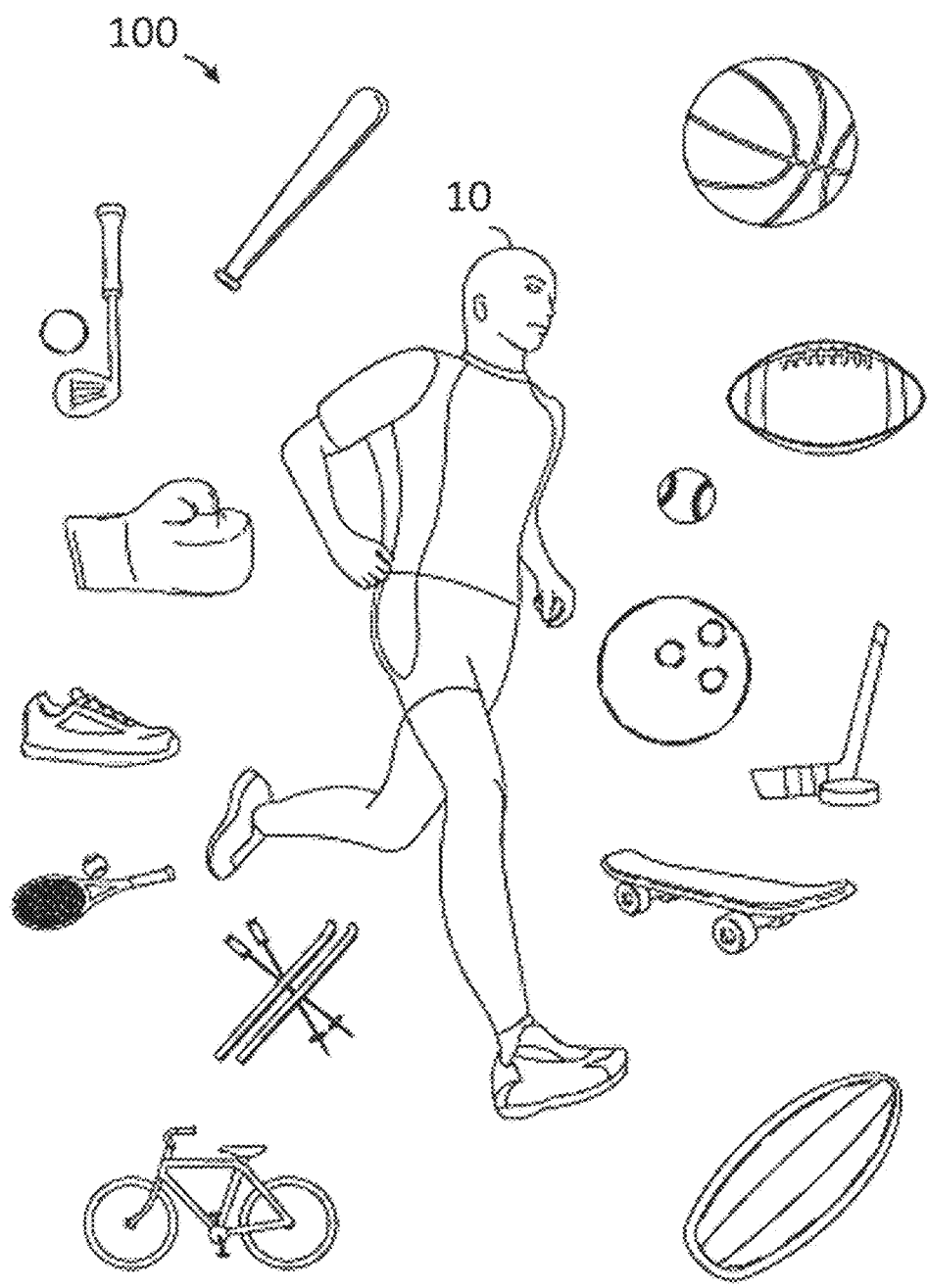
FIG. 3 is an illustration of various different pieces of athletic equipment according to embodiments of the present invention.

FIG. 3 is an illustration of various different pieces of athletic equipment 104, including but not limited to sport balls 106 and sport sticks, that could be used according to embodiments of the monitoring system 100 of the present invention. As illustrated, the monitoring system 100 of the present invention may be used with a variety of different pieces of athletic equipment 104, such as, for example, a basketball, a football, a baseball bat, a baseball, a bowling ball, a hockey stick, a hockey puck, a skateboard, a surfboard, a bicycle, a pair of skis, ski poles, a tennis racquet, a tennis ball, an article of footwear, a boxing glove, a golf club, or a golf ball.

In some embodiments of the present invention, the piece of athletic equipment 104 could be wearable by the individual 10 such as an article of clothing, an article of footwear, or athletic protective equipment. In these embodiments, the sensor module 102 may be physically coupled to the portion of the individual's 10 body by a variety of releasable or non-releasable coupling means such as, for example, straps, adhesives, pockets, clips, or by being integrated into an article of clothing (e.g., shirt, pants, sock, glove, or hat), footwear, or athletic protective equipment worn by the individual 10.

In other embodiments, the sensor module 102 may be integrated within an existing piece of athletic performance monitoring equipment such as, for example, a heart rate monitoring device, a pedometer, and accelerometer-based monitoring device, or other portable fitness monitoring device.

Figure 4:
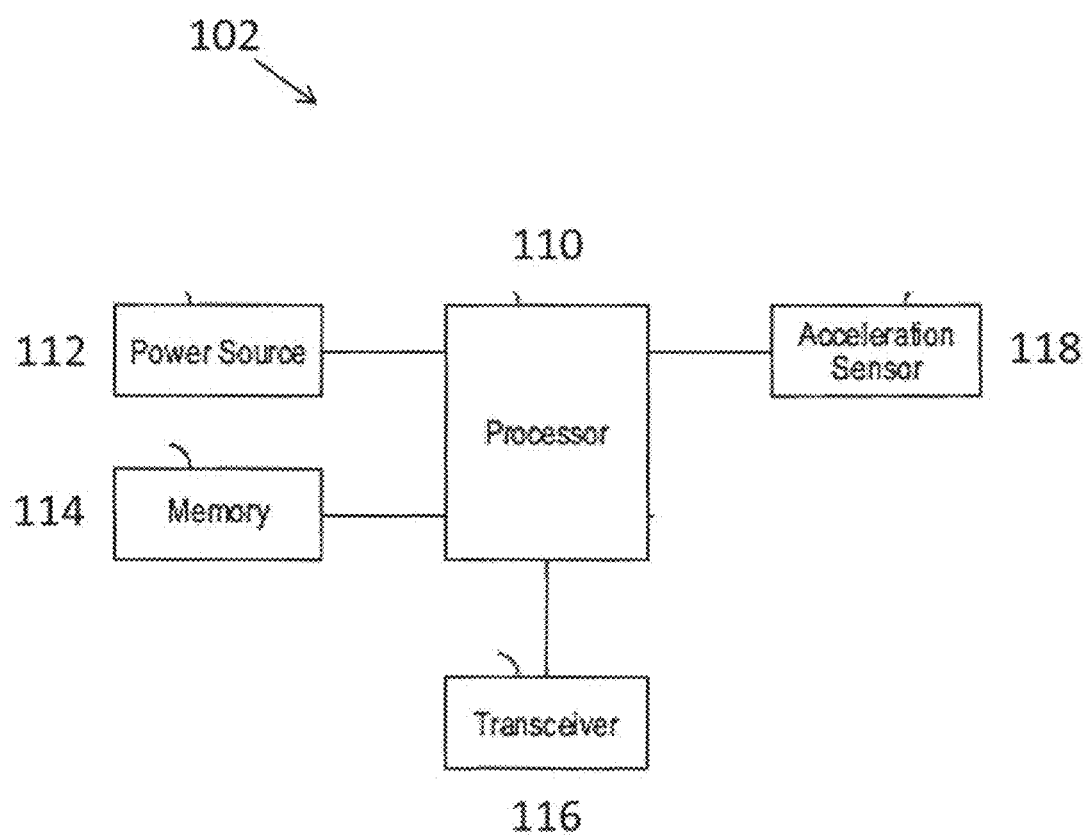
FIG. 4 is a block diagram of components of a sensor module according to an embodiment of the present invention.

FIG. 4 is a block diagram of components of a sensor module 102 according to an embodiment of the present invention. In the illustrated embodiment, the sensor module 102 includes a processor 110, a power source 112, a memory 114, a transceiver 116, and an acceleration sensor 118 operatively connected to one another to carry out the functionality of the sensor module 102. In other embodiments, one or more of these sensor module 102 components may be omitted, or one or more additional components may be added. Exemplary sensor modules 102 for use with sport balls 106 are disclosed in commonly owned U.S. patent application Ser. No. 13/446,982, filed Apr. 13, 2012 (which published as U.S. Patent App. Pub. No. 2013/0274040), the entirety of which is incorporated herein by reference thereto.

The processor 110 may be adapted to implement application programs stored in the memory 114 of the sensor module 102. The processor 110 may also be capable of implementing analog or digital signal processing algorithms such as raw data reduction and filtering. For example, processor 110 may be configured to receive raw data from sensors and process such data at the sensor module 102. The processor 110 may be operatively connected to the power source 112, the memory 114, the transceiver 116, and the acceleration sensor 118.

The power source 112 may be adapted to provide power to the sensor module 102. In one embodiment, the power source 112 may be a battery. The power source may be built into the sensor module 102 or removable from the sensor module 102, and may be rechargeable or non-rechargeable. In one embodiment, the sensor module 102 may be repowered by replacing one power source 112 with another power source 112. In another embodiment, the power source 112 may be recharged by a cable attached to a charging source, such as a universal serial bus ("USB") FireWire, Ethernet, Thunderbolt, or headphone cable, attached to a personal computer. In yet another embodiment, the power source 112 may be recharged by inductive charging, wherein an electromagnetic field is used to transfer energy from an inductive charger to the power source 112 when the two are brought in close proximity, but need not be plugged into one another via a cable. In some embodiment, a docking station may be used to facilitate charging.

Figure 5:
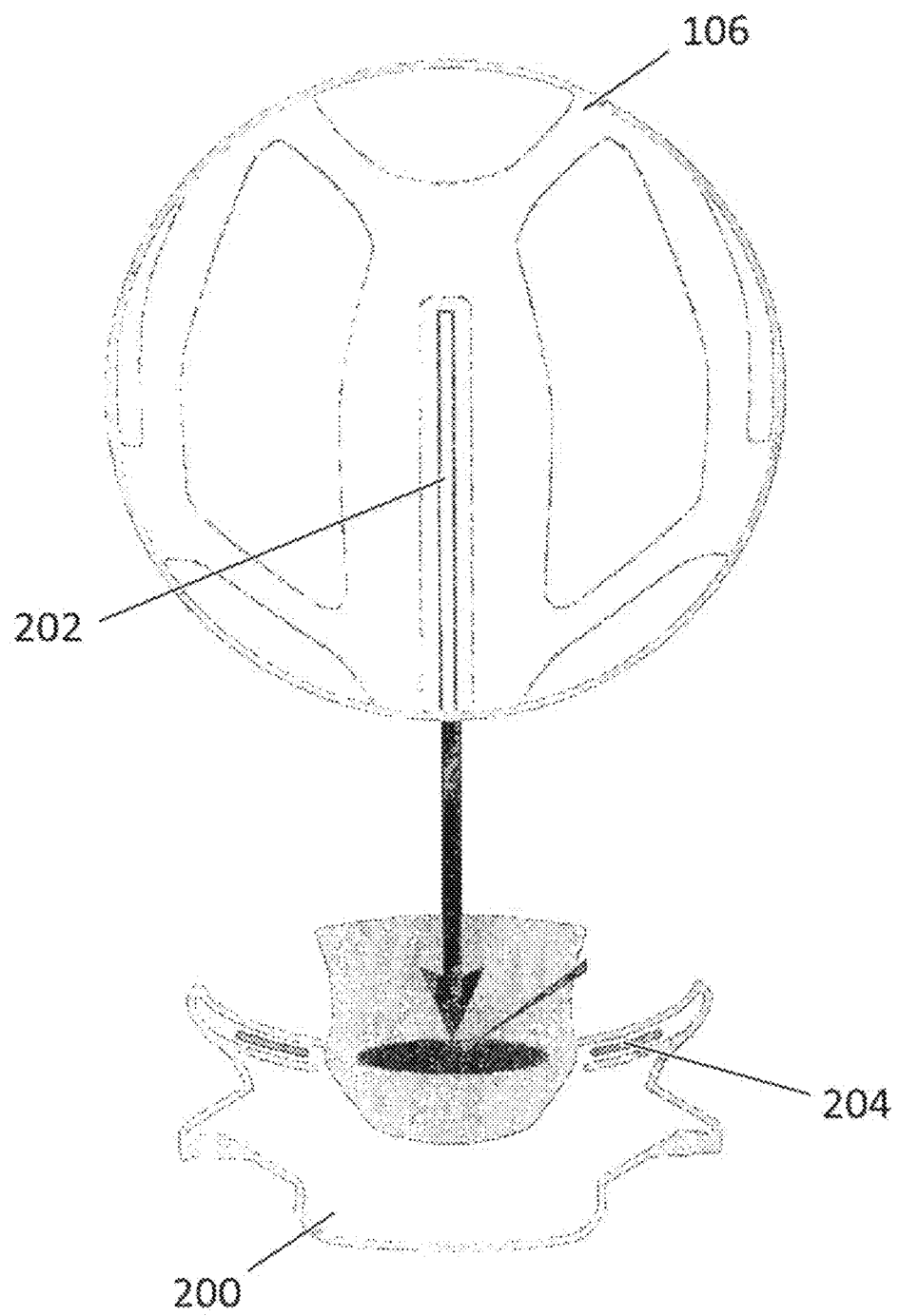
FIG. 5 is an illustration of a sport ball and a charging base, according to an embodiment of the present invention.

For example, as illustrated in FIG. 5, sensor module 102 of a piece of athletic equipment 104 in accordance with embodiments of the present invention, such as a soccer ball 106, can be powered by charging via a charging base 200. For example, power source 112 of soccer ball 106 sensor module 102 may be powered by inductive charging, in which case an inductive coil may be mounted in soccer ball 106 and coupled to power source 112 of sensor module 102.

In some embodiments the inductive coil may receive power from an inductive charging device, such as charging base 200, when soccer ball 106 is placed so that the inductive coil is sufficiently close to an inductive coil charging device.

In some embodiments, soccer ball 106 has exterior markings 202 to indicate the location of the inductive coil or to otherwise facilitate optimum orientation of soccer ball 106 for charging. For example, in the embodiment of FIG. 5, the vertical line exterior marking 202 on the front of the soccer ball 106 could be aligned with a corresponding line (not illustrated) of the charging base 200 when the soccer ball 106 is properly positioned for charging. In another embodiment, exterior markings 202 in the form of a charging icon, such as a lightning bolt icon or a series of concentric circles, could be present on a bottom surface of the soccer ball 106, and matching or complementary exterior markings 202 could be present on the charging base 200 so that the individual 10 could know that these exterior markings 202 should be aligned for optimal charging. An alignment for optimal charging may be, for example, an orientation having the inductive coil of the soccer ball 106 closest to the inductive coil charging device of the charging base 200.

In some embodiments, as illustrated in FIG. 5, the charging base 200 may include one or more visual indicators 204, such as, for example, one or more externally-visible light emitting diodes ("LEDs") that give an indication of the strength of charge being received through the inductive coil, to facilitate optimum orientation of the soccer ball 106. For example, the LEDs may emit or not emit light, the light emitted by the LEDs may change color, or the speed of the LEDs blinking may change to indicate the strength of charge being received. In other embodiments, similar LEDs with similar functionality may part of the soccer ball 106 instead of or in addition to part of the charging base 200.

Returning to FIG. 4, the memory 114 of an exemplary sensor module 102 may be adapted to store application program instructions and to store athletic activity data, such as motion data. In an embodiment, the memory 114 may store application programs used to implement aspects of the functionality of the motion monitoring system 100 described herein. In one embodiment, the memory 114 may store raw data, recorded data, and/or calculated data. In some embodiments, as explained in further detail below, the memory 114 may act as a data storage buffer. The memory 114 may include both read only memory and random access memory, and may further include memory cards or other removable storage devices.

In some embodiments of the present invention, the memory 114 may store raw data, recorded data, and/or calculated data permanently, while in other embodiments the memory 114 may only store all or some data temporarily, such as in a buffer. In one embodiment of the present invention, the memory 114, and/or a buffer related thereto, may store data in memory locations of predetermined size such that only a certain quantity of data may be saved for a particular application of the present invention.

The transceiver 116 depicted in FIG. 4 may enable the sensor module 102 to wirelessly communicate with other components of the motion monitoring system 100, such as those described in further detail below. In one embodiment, the sensor module 102 and the other local components of the motion monitoring system 100 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for an motion monitoring system 100 may also be used.

In one embodiment, the transceiver 116 is a low-power transceiver. In some embodiments, the transceiver 116 may be a two-way communication transceiver 116, while in other embodiments the transceiver 116 may be a one-way transmitter or a one-way receiver. Wireless communication between the sensor module 102 and other components of the motion monitoring system 100 is described in further detail below. In particular, wireless communication between the sensor module 102 and a portable electronic device running a sport ball motion monitoring system portable electronic device software application is described in further detail below. In other embodiments, the sensor module 102 may be in wired communication with other components of the motion monitoring system 100 that do not rely on transceiver 116.

The acceleration sensor 118 may be adapted to measure the acceleration of the sensor module 102. Accordingly, when the sensor module 102 is physically coupled to a piece of athletic equipment 104, the acceleration sensor 118 may be capable of measuring the acceleration of the piece of athletic equipment 104, including the acceleration due to the Earth's gravitational field. In one embodiment, the acceleration sensor 118 may include a tri-axial accelerometer that is capable of measuring acceleration in three orthogonal directions. In other embodiments one, two, three, or more separate accelerometers may be used.

In some embodiments of the present invention, a sensor module 102 having components such as those depicted in FIG. 4 may be physically coupled to piece of athletic equipment 104 during an athletic activity conducted by an individual 10 to monitor changes in the spatial orientation of the piece of the individual's 10 athletic equipment 104, or to determine a correlation between equipment 104 movement data and an activity metric. In these embodiments, the acceleration sensor 118 may be responsible for collecting the data necessary to carry out the various monitoring calculations.

In some other embodiments, however, it may be desirable to have additional sensors included within the sensor module 102, or to have additional sensors in communication with the sensor module 102. In further embodiments, the sensor module 102 may be integrated within an existing piece of athletic activity monitoring equipment possibly having additional or different sensors such as, for example, a heart rate monitoring device, a pedometer, and accelerometer-based monitoring device, or other portable fitness monitoring device.

In one embodiment of the present invention, the sensor module 102 may further include a magnetic field sensor 120 that may be adapted to measure the strength and direction of magnetic fields in the vicinity of the sensor module 102. Accordingly, when the sensor module 102 is physically coupled to a piece of athletic equipment 104, the magnetic field sensor 120 may be capable of measuring the strength and direction of magnetic fields in the vicinity of the equipment 104, including the Earth's magnetic field. In one embodiment, the magnetic field sensor 120 may be a vector magnetometer. In other embodiments, the magnetic field sensor 120 may be a tri-axial magnetometer that is capable of measuring the magnitude and direction of a resultant magnetic vector for the total local magnetic field in three dimensions. In other embodiments one, two, three, or more separate magnetometers may be used.

In one embodiment, the acceleration sensor 118 and the magnetic field sensor 120 may be contained within a single accelerometer-magnetometer module bearing model number LSM303DLHC made by STMicroelectronics of Geneva, Switzerland. In other embodiments, the sensor module 102 may include only one of the acceleration sensor 118 and the magnetic field sensor 120, and may omit the other if desired.

In addition to the acceleration sensor 118 and the magnetic field sensor 120, other sensors that may be part of the sensor module 102 or separate from but in communication with the sensor module 102 may include sensors capable of measuring a variety of athletic performance parameters. The term "performance parameters" may include physical parameters and/or physiological parameters associated with the individual's 10 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

Actual sensors that may be capable of measuring these parameters may include, but are not limited to, a pedometer, a pulsimeter, a thermometer, an altimeter, a pressure sensor, a strain gage, a bicycle power meter, a bicycle crank or wheel position sensor, a magnetic sensor, an angular momentum sensor (e.g., a gyroscope), a resistance sensor, or a force sensor.

Figure 6:
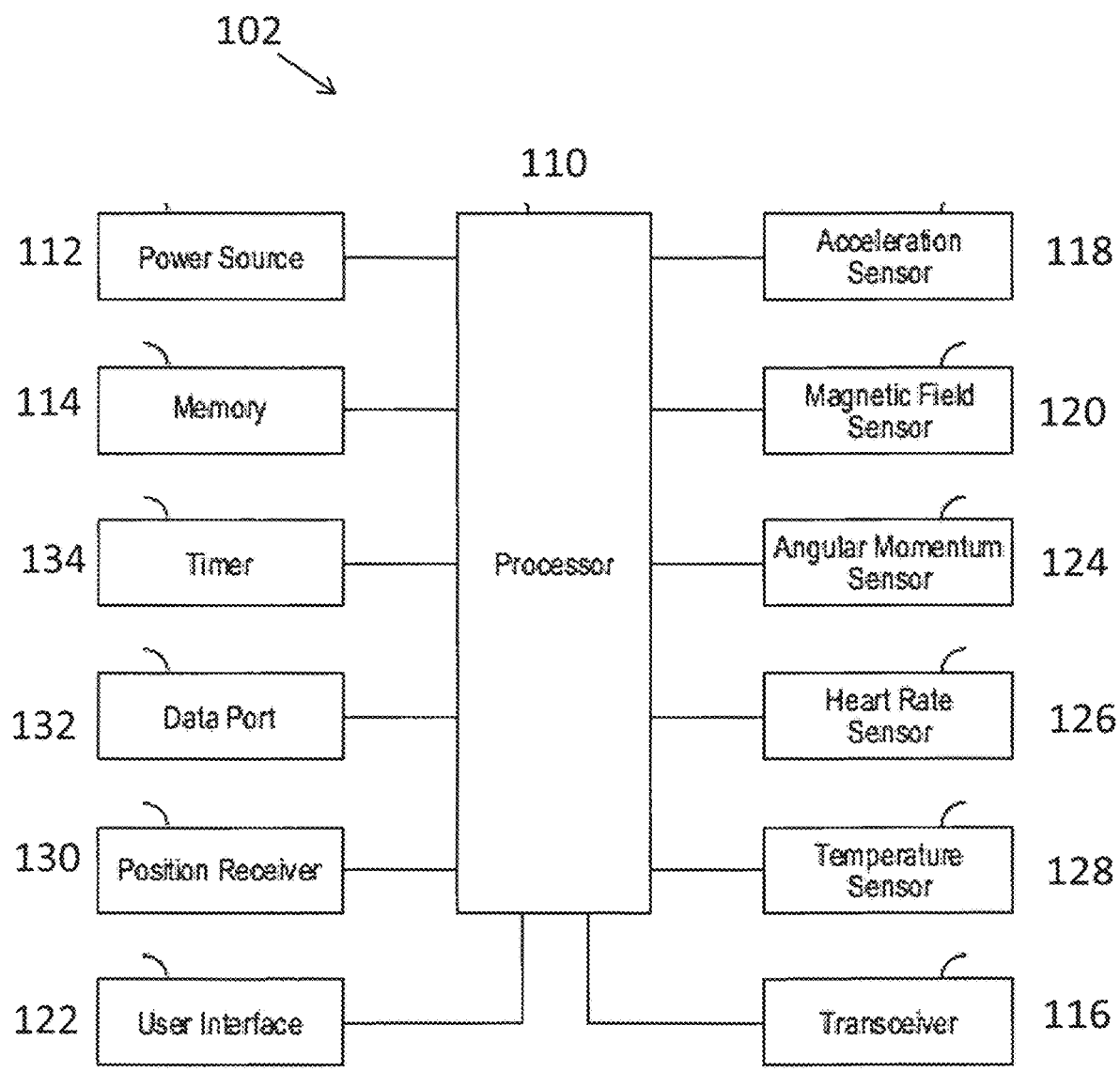
FIG. 6 is a block diagram of components of a sensor module according to an embodiment of the present invention.

FIG. 6 is a block diagram of components of a sensor module 102 according to another embodiment of the present invention that may incorporate some of the additional sensors mentioned above, as well as other additional components. In the illustrated embodiment, the sensor module 102 includes a processor 110, a power source 112, a memory 114, a transceiver 116, an acceleration sensor 118, a magnetic field sensor 120, a user interface 122, an angular momentum sensor 124, a heart rate sensor 126, a temperature sensor 128, a position receiver 130, a data port 132, and a timer 134 operatively connected to one another to carry out the functionality of the sensor module 102. In other embodiments, one or more of these sensor module 102 components may be omitted, or one or more additional components may be added.

The processor 110, the power source 112, the memory 114, the transceiver 116, and the acceleration sensor 118 of the embodiment of FIG. 6 may have structures and functions similar to those described above with respect to analogous components in FIG. 4. In some embodiments, the transceiver 116 may be a two-way communication transceiver 116, while in other embodiments the transceiver 116 may be a one-way transmitter or a one-way receiver.

The user interface 122 of the sensor module 102 may be used by the individual 10 to interact with the sensor module 102. In an embodiment, the user interface 122 may include one or more input buttons, switches, or keys, including virtual buttons, switches, or keys of a graphical user interface touch screen surface. The function of each of these buttons, switches, or keys may be determined based on an operating mode of the sensor module 102. In one embodiment, the user interface 122 may include a touch pad, scroll pad and/or touch screen. In another embodiment, the user interface 122 may include capacitance switches. In a further embodiment, the user interface 122 may include audio or voice-activated controls. In one embodiment, audio controls may be capable of conveying the status or battery life of the sensor module 102 to an individual 10. In another embodiment, the audio controls may be capable of outputting or receiving performance parameter information, feedback, or other information to and from the individual 10. In one embodiment, the audio controls may be capable of accepting voice commands from the individual 10. In another embodiment, the sensor module 102 may be capable of relaying audio information to an individual 10 wirelessly via another device, such as a pair of headphones.

In some embodiments, however, the sensor module 102 may not include a user interface 122. In these embodiments, the sensor module 102 may be capable of communicating with other components of the motion monitoring system 100 which may themselves include user interfaces.

The angular momentum sensor 124, which may be, for example, a gyroscope, may be adapted to measure the angular momentum or orientation of the sensor module 102. Accordingly, when the sensor module 102 is physically coupled to a piece of athletic equipment 104, the angular momentum sensor 124 may be capable of measuring the angular momentum or orientation of the piece of athletic equipment 104. In one embodiment, the angular momentum sensor 124 may be a tri-axial gyroscope that is capable of measuring angular rotation about three orthogonal axis. In other embodiments one, two, three, or more separate gyroscopes may be used. In an embodiment, the angular momentum sensor 124 may be used to calibrate measurements made by one or more of an acceleration sensor 118 and a magnetic field sensor 120.

The heart rate sensor 126 may be adapted to measure an individual's 10 heart rate. The heart rate sensor 126 may be placed in contact with the individual's 10 skin, such as the skin of the individual's 10 chest or hand. The heart rate sensor 126 may be capable of reading the electrical activity the individual's 10 heart.

The temperature sensor 128 may be, for example, a thermometer, a thermistor, or a thermocouple that measures changes in the temperature. In some embodiments, the temperature sensor 128 may primarily be used for calibration other sensors of the motion monitoring system 100, such as, for example, the acceleration sensor 118 and the magnetic field sensor 120.

In one embodiment, the positioning system receiver 130 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the positioning system receiver 130 may be an antennae that is capable of communicating with local or remote base stations or radio transmission transceivers such that the location of the sensor module 102 may be determined using radio signal triangulation or other similar principles. In some embodiments, positioning system receiver 130 data may allow the sensor module 102 to detect information that may be used to measure and/or calculate position waypoints, time, location, distance traveled, speed, pace, or altitude.

The data port 132 may facilitate information transfer to and from the sensor module 102 and may be, for example, a USB port. In some exemplary embodiments, data port 132 can additionally or alternatively facilitate power transfer to power source 112, in order to charge power source 112.

The timer 134 may be a clock that is capable of tracking absolute time and/or determining elapsed time. In some embodiments, the timer 134 may be used to timestamp certain data records, such that the time that certain data was measured or recorded may be determined and various timestamps of various pieces of data may be correlated with one another.

In some embodiments of the present invention, a sensor module 102 having components such as those depicted in FIG. 6 may be physically coupled to a piece of athletic equipment 104 during an athletic activity conducted by an individual 10 to monitor changes in the spatial orientation of the piece of athletic equipment 104, or to determine a correlation between equipment 104 movement data and an activity metric. In these embodiments, the acceleration sensor 118, the magnetic field sensor 120, and/or other included sensors may be responsible for collecting the data necessary to carry out the various monitoring calculations. In some other embodiments, however, it may be desirable to have additional sensors included within the sensor module 102, to have additional sensors in communication with the sensor module 102, or to have fewer sensors with the sensor module 102.

In some embodiments, the sensor module 102 may include a housing. The housing may contain and protect the various electronic components of the exemplary sensor modules 102 described above with reference to FIG. 4 or FIG. 6. The housing may take on any suitable size and shape that is able to accommodate the necessary components of the sensor module 102 and to physically couple to the desired part of the piece of athletic equipment 104. In one embodiment, the housing may be made of plastic, such as, for example, TPU, or other suitably durable material.

In some embodiments of the present invention, the sensor module 102 may communicate with other components of the motion monitoring system 100 via wired or wireless technologies. Communication between the sensor module 102 and other components of the motion monitoring system 100 may be desirable for a variety of reasons. For example, to the extent that the sensor module 102 records and stores athletic activity information, it may be useful to transmit this information to another electronic device for additional data processing, data visualization, sharing with others, comparison to previously recorded athletic activity information, or a variety of other purposes. As a further example, to the extent that the sensor module 102 has insufficient processing power, wide area network transmission capabilities, sensor capabilities, or other capabilities, these capabilities can be provided by other components of the motion monitoring system 100. With this in mind, possible communications means are described briefly below.

Wired communication between the sensor module 102 and a personal computer 304 may be achieved, for example, by placing the sensor module 102—or a piece of athletic equipment 104 including the sensor module 102—in a docking unit that is attached to the personal computer 304 using a communications wire plugged into a communications port of the personal computer 304. In another embodiment, wired communication between the sensor module 102 and the personal computer 304 may be achieved, for example, by connecting a cable between the sensor module 102—or a piece of athletic equipment 104 including the sensor module 102—and the computer 304. The data port 132 of the sensor module 102 and a communications port of the computer 304 may include USB ports. The cable connecting the sensor module 102 and the computer 304 may be a USB cable with suitable USB plugs including, but not limited to, USB-A or USB-B regular, mini, or micro plugs, or other suitable cable such as, for example, a FireWire, Ethernet or Thunderbolt cable. As previously explained above, in some embodiments, such cables could be used to facilitate power transfer to a power source 112 of the sensor module 102, in order to charge the power source 112. Alternatively, the power source 112 may be recharged by inductive charging, or by using a docking station with a charging base 200.

Wired connection to a personal computer 304 may be useful, for example, to upload athletic activity information from the sensor module 102 to the personal computer 304, or to download application software updates or settings from the personal computer 304 to the sensor module 102.

Wireless communication between the sensor module 102—or a piece of athletic equipment 104 including the sensor module 102—and the personal computer 304 may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the sensor module 102 and the various elements of the motion monitoring system 100 of the present invention.

In one embodiment, the sensor module 102—or a piece of athletic equipment 104 including the sensor module 102—may communicate with a wireless wide area network communications system such as that employed by mobile telephones. For example, a wireless wide area network communication system may include a plurality of geographically distributed communication towers and base station systems. Communication towers may include one or more antennae supporting long-range two-way radio frequency communication wireless devices, such as sensor module 102. The radio frequency communication between antennae and the sensor module 102 may utilize radio frequency signals conforming to any known or future developed wireless protocol, for example, CDMA, GSM, EDGE, 3G, 4G, IEEE 802.x (e.g., IEEE 802.16 (WiMAX)), etc. The information transmitted over-the-air by the base station systems and the cellular communication towers to the sensor module 102 may be further transmitted to or received from one or more additional circuit-switched or packet-switched communication networks, including, for example, the Internet.

Figure 7:
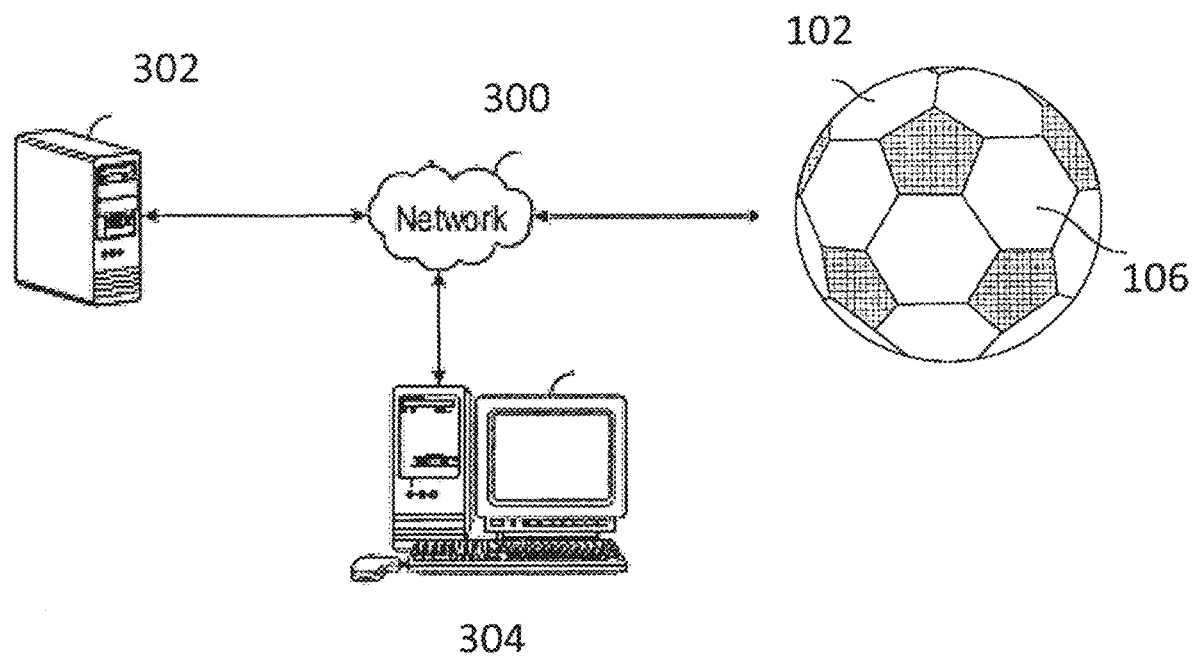
FIG. 7 is an illustration of various components of an athletic activity monitoring system communicating according to an embodiment of the present invention.

As shown in FIG. 7, communication may also occur between the sensor module 102, a personal computer 304, and/or a remote server 302 via a network 300. In an embodiment, the network 300 is the Internet. The Internet is a worldwide collection of servers, routers, switches and transmission lines that employ the Internet Protocol (TCP/IP) to communicate data. The network 300 may also be employed for communication between any two or more of the sensor module 102, the personal computer 304, the server 302, and a docking unit. In an embodiment of the present invention, information is directly communicated between the sensor module 102 and the server 302 via the network 300, thus bypassing the personal computer 304.

A variety of information may be communicated between any of the sensor module 102, the personal computer 304, the network 300, the server 302, or other electronic components such as, for example, another sensor module 102, a mobile phone, a tablet computer, or other portable electronic devices. Such information may include, for example, performance parameter data, device settings (including sensor module 102 settings), software, and firmware.

Communication among the various elements of the present invention may occur after the athletic activity has been completed or in real-time during the athletic activity. In addition, the interaction between, for example, the sensor module 102 and the personal computer 304, and the interaction between the personal computer 304 and the server 302 may occur at different times.

In some embodiments of the present invention, an individual 10 using the motion monitoring system 100 may participate in the activity with the sensor module 102 physically coupled to a piece of athletic equipment 104, but with no other portable electronic devices making up part of the motion monitoring system 100 in the individual's 10 immediate vicinity. In such an embodiment, the sensor module 102 would monitor the athletic activity using its sensors. The sensor module 102 may also perform calculations necessary to monitor changes in the spatial orientation of the piece of athletic equipment 104, or perform calculations necessary to determine a correlation between equipment 104 movement data and an activity metric.

Alternatively, in this scenario, other components of the motion monitoring system 100 that are remotely located from the individual 10 during the activity could be relied upon to perform calculations necessary to monitor changes in the spatial orientation of the piece of athletic equipment 104, or perform calculations necessary to determine a correlation between equipment 104 movement data and an activity metric. This could occur, for example after wireless transmission of athletic performance information directly from the sensor module 102 to a personal computer 304 or a server 302 during or after the activity, or after a wired transmission of athletic performance information directly from the sensor module 102 to a personal computer 304 after the activity.

Figure 8:
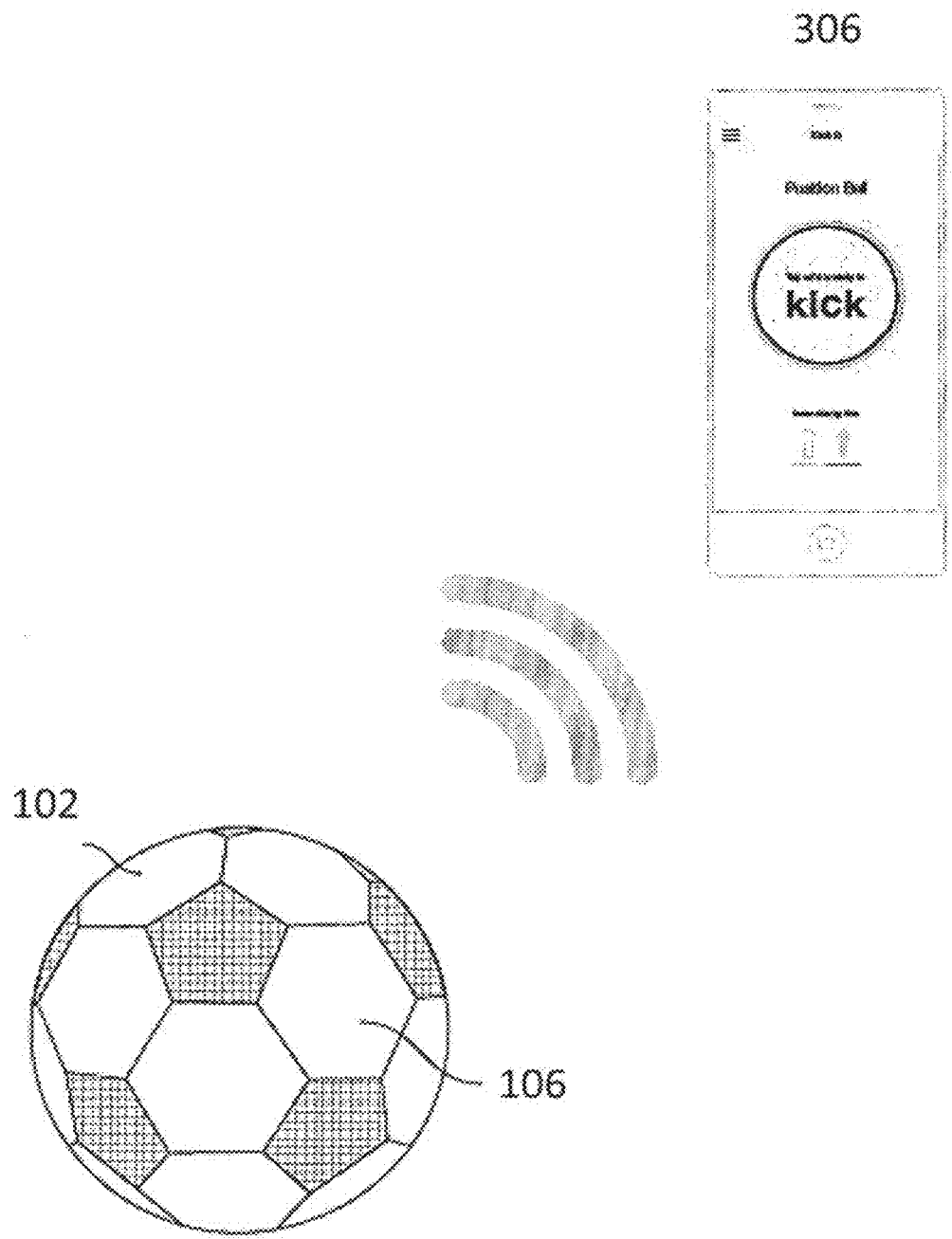
FIG. 8 is an illustration of various components of an athletic activity monitoring system communicating according to an embodiment of the present invention.

However, in other embodiments of the present invention, as illustrated in FIG. 8, the sensor module 102 may communicate with a portable electronic device 306 of the motion monitoring system 100 that is also carried by the individual 10 during the athletic activity. In some embodiments, the portable electronic device 306 may be carried by another person besides the individual 10, or not carried by any person. In some embodiments, the portable electronic device 306 may be a watch, a mobile phone, a tablet computer, or other portable electronic device. In one embodiment of the present invention, as described in further detail below, in particular with respect to FIGS. 22-49, the sensor module 102 may communicate with a portable electronic device 306 running a sport ball 106 motion monitoring system 100 portable electronic device 306 software application.

The portable electronic device 306 may serve a variety of purposes including, for example, providing additional data processing, providing additional data storage, providing data visualization, providing additional sensor capabilities, relaying information to a network 300, or providing for the playback of music or videos.

In one embodiment of the present invention, the portable electronic device 306 may be a dedicated portable electronic device 306. The term "dedicated portable electronic device" indicates that the portable electronic device 306 is not capable of serving another purpose outside of the motion monitoring system 100 of the present invention. For example, a mobile phone, a personal digital assistant, or a digital music file player (e.g., an MP3 player) may not be considered to be "dedicated portable electronic monitoring devices" as the term is used herein. In this manner, the dedicated portable electronic monitoring device 306 may in some embodiments provide a simpler and/or more efficient device.

The portable electronic device 306 illustrated in FIG. 8 is not a dedicated portable electronic monitoring device; the portable electronic device 306 illustrated in FIG. 8 is a mobile phone. In alternate embodiments, it may be possible for the sensor module 102 itself to be embodied by a mobile phone. Including a portable electronic device 306 in the motion monitoring system 100, such as a mobile phone, may be desirable as mobile phones are commonly carried by individuals 10, even when engaging in athletic activities, and they are capable of providing significant additional computing and communication power at no additional cost to the individual 10.

In view of the above discussion, it is apparent that various processing steps or other calculations recited herein may be capable of being performed by various embodiments of the motion monitoring system 100 disclosed herein, and are not necessarily limited to being performed by the sensor module 102, depending on the configuration of a particular embodiment of the present invention. For example, any of the processing steps or other calculations recited herein may be performed, in various embodiments, by the sensor module 102, by a server computer 302, by a personal computer 304, by a portable electronic device 306, and/or any other network component, or by more than one component.

Embodiments of the present invention may involve the use of so-called "cloud computing." Cloud computing may include the delivery of computing as a service rather than a product, whereby shared resources, software, and information are provided to computers and other devices as a utility over a network (typically the Internet). Cloud computing may entrust services (typically centralized) with an individual's 10 data, software and computation on a published application programming interface over a network. End users may access cloud-based applications through a web browser or a light weight desktop or mobile app while the business software and data are stored on servers at a remote location. Cloud application providers often strive to give the same or better service and performance than if the software programs were installed locally on end-user computers.

Embodiments of the present invention may incorporate features of group athletic activity monitoring systems. Exemplary of group athletic activity monitoring systems are disclosed in commonly owned U.S. patent application Ser. No. 13/077,494, filed Mar. 31, 2011 (which published as U.S. Patent App. Pub. No. 2012/0254934), the entirety of which is incorporated herein by reference thereto.

An overview of exemplary embodiments of components of the athletic equipment motion monitoring system 100 of the present invention, including exemplary sensor modules 102, has been provided above.

II. Exemplary Methods of Using Motion Monitoring Systems

A description of various exemplary methods of using the motion monitoring system 100 of the present invention to monitor changes in the spatial orientation or movement of a piece of athletic equipment 104, or to determine a correlation between equipment 104 movement data and an activity metric is now provided below.

An individual 10 engaged in an athletic activity (or another interested person such as a coach, teammate, or spectator) may desire to obtain information about the motion of a piece of the individual's 10 athletic equipment 104 during the course of the athletic activity.

For example, if the individual 10 is participating in an activity that involves the use of a sport ball 106, such as playing in a soccer match, it may be desirable, for example, to be able to determine the various launch angles at which the soccer ball 106 (i.e., football) was kicked by the individual's 10 foot 12, to be able to determine the rate of rotation of the soccer ball 106 after it was kicked by the individual 10, to be able to determine the peak speeds that the soccer ball 106 was traveling at after being kicked by the individual 10, or to be able to determine the specific locations on the surface of the soccer ball 106 where the individual's 10 foot 12 struck the ball when kicking the soccer ball 106.

By using the motion monitoring system 100 including the sensor module 102 described above, embodiments of the present invention may advantageously enable the individual 10 (or their coach, teammate, or a spectator) to obtain this or other information about the motion of the piece of athletic equipment 104 during or after the course of the athletic activity.

While various embodiments of the present invention are described in the context of the sports of soccer (i.e., football), the present invention is not so limited and may be applied in a variety of different sports or athletic activities including, for example, baseball, basketball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

Data obtained by the sensor module 102 may be processed in a variety of ways to yield useful information about the motion of a piece of athletic equipment 104 during the activity. In some embodiments, sensor module 102 data may be processed to monitor changes in the spatial orientation of a piece of athletic equipment 104. In other embodiment, sensor module 102 data may be processed to by reference to a predetermined correlation between movement data and an activity metric stored in a data structure.

Figure 9:
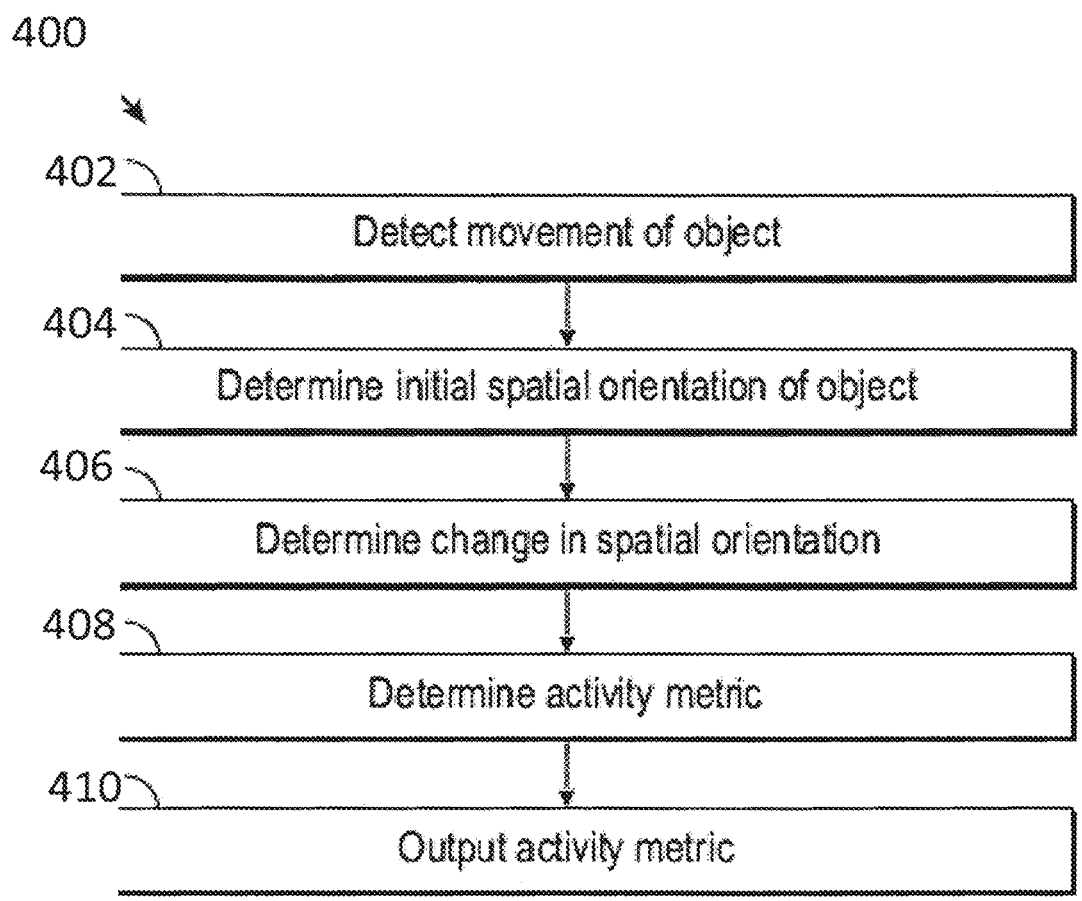
FIG. 9 is flow chart illustrating a method for determining an activity metric according to an embodiment of the present invention.

With reference to FIG. 9, in one embodiment of the present invention, an individual 10 may use the sensor module 102 in the motion monitoring system 100 to determine a change in spatial orientation of the piece of athletic equipment 104 according to spatial orientation process 400 as follows.

First, at step 402, the sensor module 102 may detect movement of the piece of athletic equipment 104. In one embodiment, movement of the piece of athletic equipment 104 is detected based on acceleration data captured by the acceleration sensor 118 of the sensor module 102. In another embodiment, movement of the piece of athletic equipment 104 is detected based on magnetic field data captured by the magnetic field sensor 120 of the sensor module 102. In yet another embodiment, movement of the piece of athletic equipment 104 is detected based on both acceleration data and magnetic field data.

In one embodiment, the magnetic field sensor 120 may be adapted to measure the strength and direction of magnetic fields in the vicinity of the sensor module 102. In another embodiment, the magnetic field sensor 120 may be adapted to measure the strength and direction of the Earth's magnetic field in the vicinity of the sensor module 102. In some embodiments, the magnetic field sensor 120 may be capable of measuring the magnitude and direction of a resultant magnetic vector for the total local magnetic field and/or for the local Earth's magnetic field.

If the monitored piece of athletic equipment 104 is a soccer ball 106, the detected movement may consist of the soccer ball 106 rolling on the ground as a result of being dribbled by the individual 10.

In some embodiments, the sensor module 102 may then determine that the movement of the piece of athletic equipment 104 indicates the occurrence of a movement to track. In one embodiment, the determination that the movement of the piece of athletic equipment 104 indicates the occurrence of a movement to track occurs when a threshold data value is met for a predetermined period of time. For example, the sensor module 102 may determine that a movement of the piece of athletic equipment 104 has resulted in a threshold acceleration and/or magnetic field change occurring for a predetermined period of time.

In some embodiments, the determination of the occurrence of a movement to track is an indication that the movement to track had already begun prior to the determination. In this case, it is still possible to capture all of the relevant data relating to the movement as the sensor module 102 may temporarily record a stream of data in a buffer in the event that data that had recently been recorded may need to be examined or more permanently recorded in response to a determination that an occurrence of a movement to track is found. In other embodiments, the determination of the occurrence of a movement to track is an indication that the movement to track is about to begin in the near future. In some embodiments, the sensor module 102 is adapted to store data permanently or temporarily, and may further be adapted to store data for predefined periods of time in certain circumstances, such as when populating a data buffer.

If the monitored piece of athletic equipment 104 is a soccer ball 106, the movement of the soccer ball 106 as a result of the individual 10 swiftly kicking the soccer ball 106 with their foot 12 in an attempt to make a goal may result in a determination that the motion of the soccer ball 106 in response to the kick—which could include motion of the soccer ball 106 before, during, and/or after the determination was made—should be tracked.

Next, as step 404, in response to the determination of the occurrence of a movement to track, an initial spatial orientation of the piece of athletic equipment 104 may be determined. In some embodiments, the determination of an initial spatial orientation of the piece of athletic equipment 104 may be made by reference to a coordinate axis system.

Figure 10:
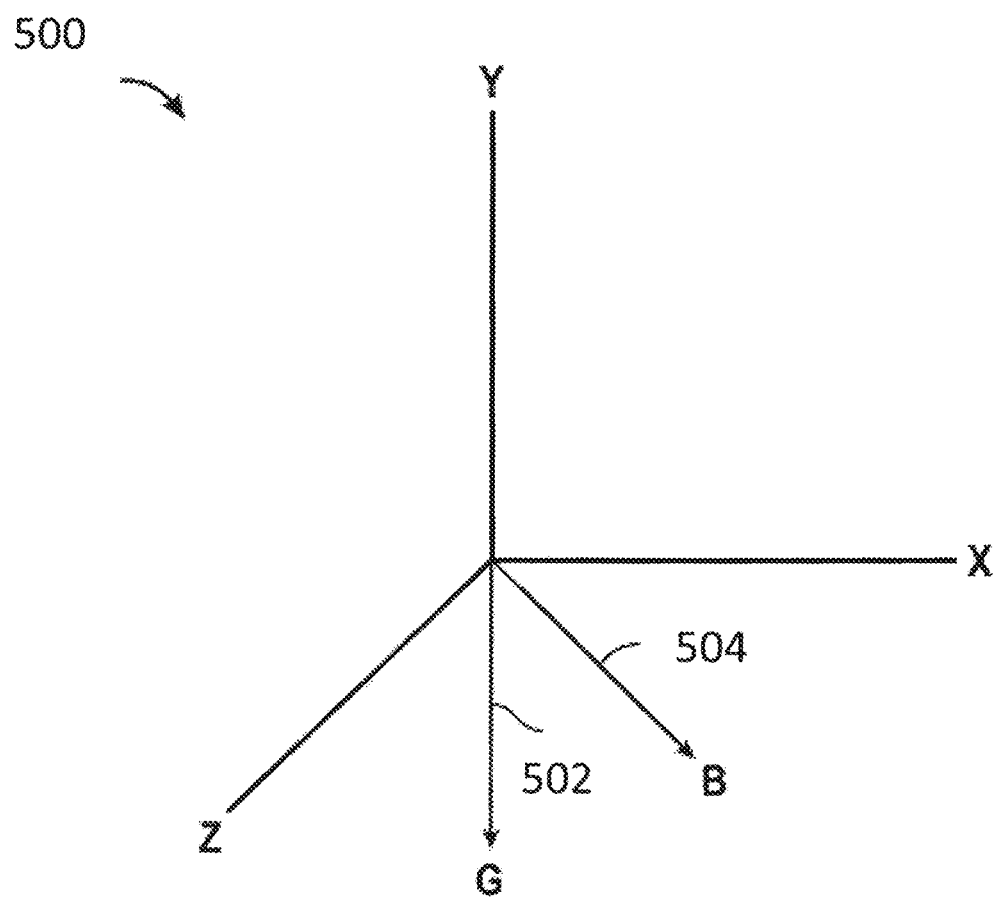
FIG. 10 is an illustration of an exemplary coordinate system according to an embodiment of the present invention.

A coordinate axis system is a useful analytical tool for monitoring changes in the spatial orientation of an object, such as piece of athletic equipment 104. FIG. 10 illustrates an exemplary three-dimensional Cartesian coordinate axis system 500 having three axes—an X axis, a Y axis, and a Z axis. Two vectors, "G" and "B," are superimposed on the coordinate axis system 500 illustrated in FIG. 10. The G-vector 502 pointing in the −Y direction represents a gravity vector. The B-vector 504 represents a resultant magnetic field vector.

Figure 11:
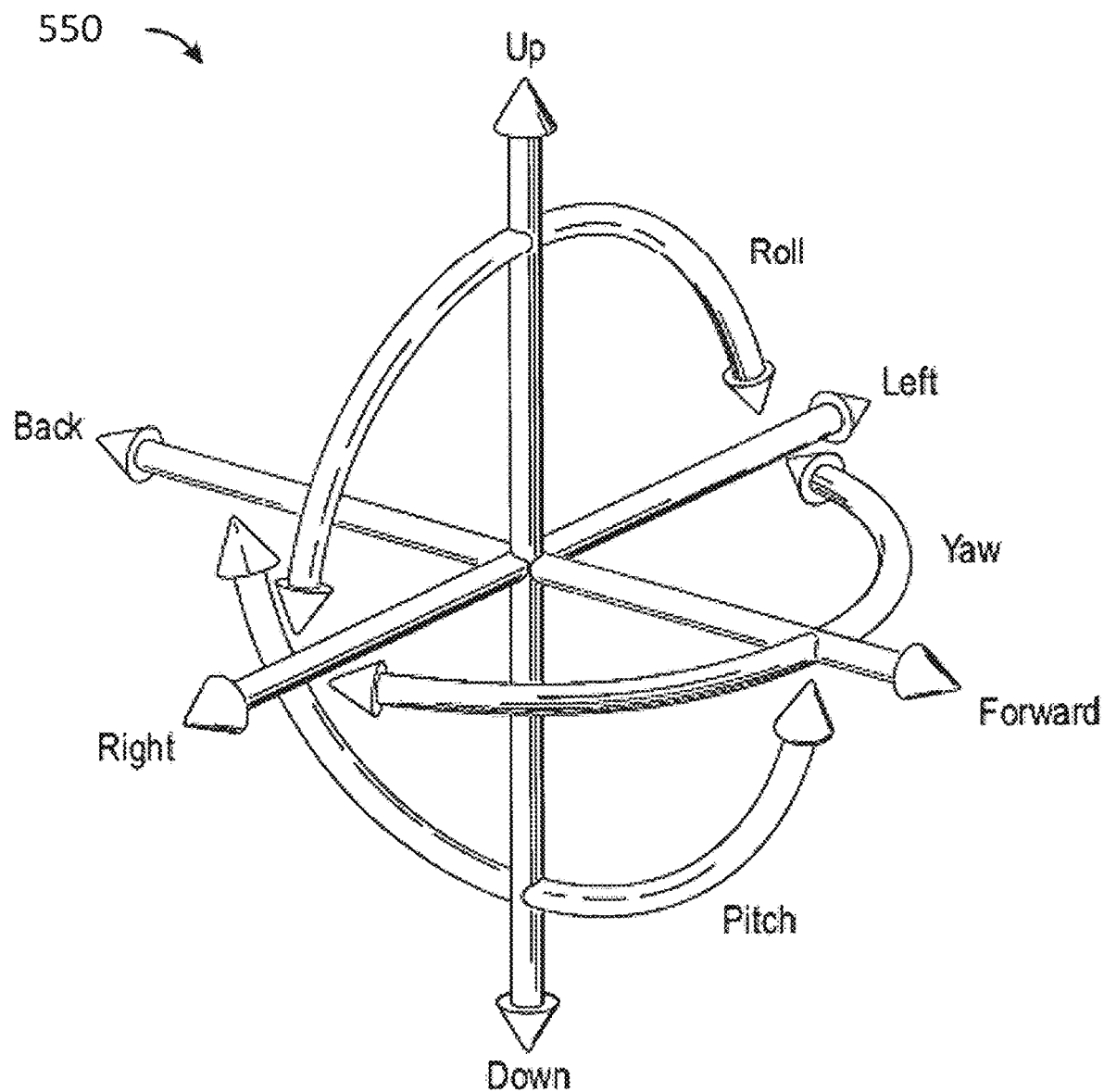
FIG. 11 is an illustration of an exemplary coordinate system according to an embodiment of the present invention.

FIG. 11 illustrates another exemplary three-dimensional Cartesian coordinate axis system 550. This system 550 defines six degrees of freedom for a rigid body, such as the piece of athletic equipment 104. Six degrees of freedom refers to motion of a rigid body in three-dimensional space, namely the ability to move forward/backward, up/down, left/right (translation in three perpendicular axes) combined with rotation about three perpendicular axes (pitch, yaw, roll), as illustrated in FIG. 11.

Returning to the discussion of step 404 in FIG. 9, in one embodiment, the determination of the initial spatial orientation of the piece of athletic equipment 104 may be made with respect to a gravity vector 502, such as that illustrated in FIG. 10. In another embodiment, the determination of the initial spatial orientation of the piece of athletic equipment 104 may be made with respect to an Earth magnetic field vector 504, such as that illustrated in FIG. 10. In other embodiments, the determination of the initial spatial orientation of the piece of athletic equipment 104 may be made with respect to characterizations of the way that the piece of athletic equipment translated and rotated in three-dimensional space with six degrees of freedom, as explained with reference to FIG. 11.

If the monitored piece of athletic equipment 104 is a soccer ball 106, the determination of the initial spatial orientation of the soccer ball 106 relative to the specific movement to be tracked (i.e., movement of the soccer ball 106 resulting from the kick by a foot 12) may be defined, for example, as the spatial orientation of the soccer ball 106 just before, at the moment of, or just after the soccer ball 106 was swiftly kicked by the individual's 10 foot 12, depending on the particular application and algorithms used.

At step 406, after the determination of the initial orientation of the piece of athletic equipment 104 at a first time has been made, a change in the spatial orientation of the piece of athletic equipment 104 may be determined. In an embodiment, the determination of the change in the spatial orientation of the piece of athletic equipment 104 at step 406 may be made similarly to the determination of the initial orientation of the piece of athletic equipment 104 at step 404, except that additional information about changes in the orientation of the gravity vector 502 and/or the magnetic field vector 504 as the object moves may be additionally factored in.

If the monitored piece of athletic equipment 104 is a soccer ball 106, the determination of the change in the spatial orientation of the soccer ball 106 relative to the specific movement to be tracked (i.e., movement of the soccer ball 106 resulting from the kick) may be defined, for example, as the change in spatial orientation of the soccer ball 106 from the time that the initial orientation of the soccer ball 106 was identified to a later point in time when the soccer ball 106 is still moving or has ceased moving, depending on the particular application and algorithms used.

At step 408, an activity metric is determined based on the change in the spatial orientation of the piece of athletic equipment 104 determined in step 406. The nature of the activity metric may change based on the athletic activity that the individual 10 is participating in, as well as particular piece of athletic equipment 104 that is being monitored. In one embodiment, the activity metric may relate to, for example, a launch angle, a rate of rotation, a ball trajectory, a speed, a jump height, a jump force, a jump distance, a jump trajectory, a kick force, a kick distance, an impact force, an impact location, a characterization of a specific type of athletic movement, or a reaction time measurement. In other embodiments, the activity metric may be, for example, the rate of rotation, the plane of rotation, the jump force, force profile (force acting upon the body of the athlete or the ground or the object), stroke information in tennis, swing profile in golf, baseball, hockey stick, kick profile of a leg or foot 12, angle position of a bike pedal, power output of a cyclist, fatigue (tremors starting to occur in repeated motion, i.e., running, lifting swimming, rowing etc.), posture, throwing or arm swing technique, and shooting technique.

If the monitored piece of athletic equipment 104 is a soccer ball 106, the change in the spatial orientation of the soccer ball 106 resulting from the kick may be used to determine, for example, a launch angle of the soccer ball 106, a rate of rotation of the soccer ball 106, launch speed, estimated speed, foot 12 impact location on the soccer ball 106, or similar metrics.

Finally, at step 410, an output is provided that conveys the activity metric to the individual 10, a coach, a teammate, a spectator, or any other interested person. In one embodiment, the output may be an audible, visual, and/or haptic output.

Figure 12:
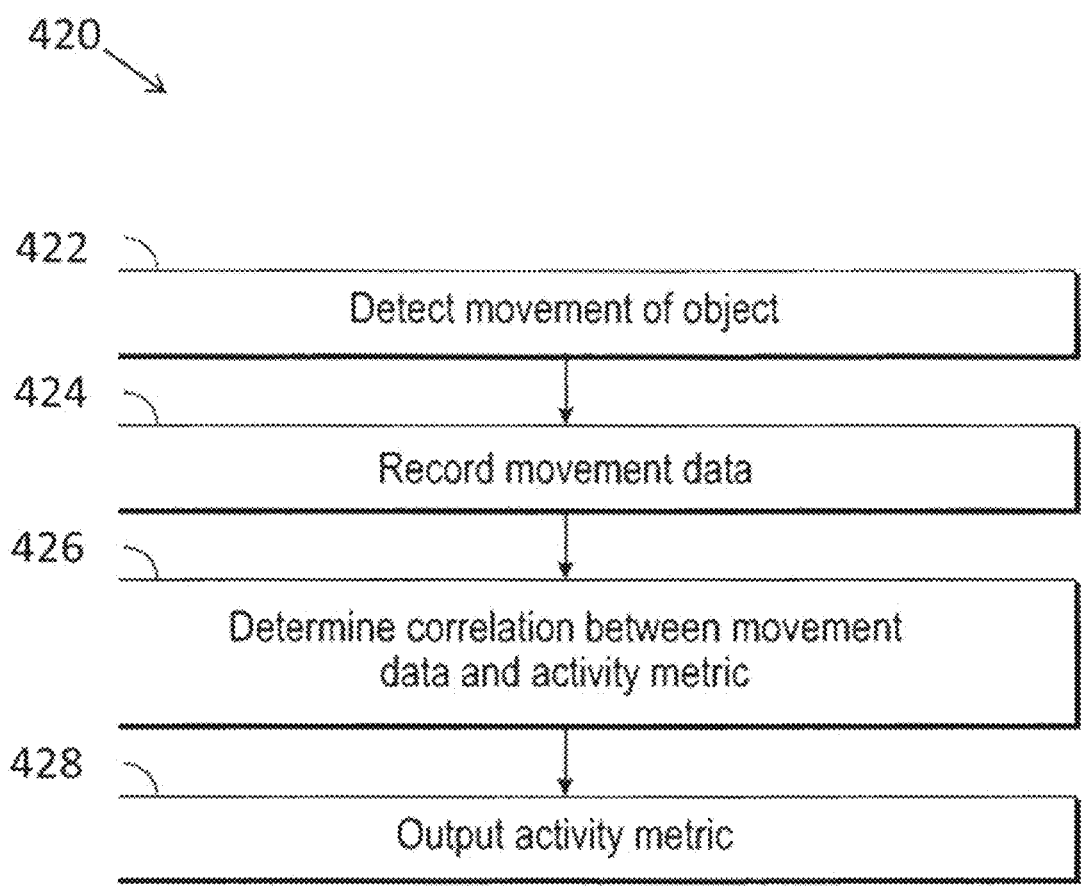
FIG. 12 is flow chart illustrating a method for determining an activity metric according to an embodiment of the present invention.

In some embodiments of the present invention, instead of a desire to monitor changes in the spatial orientation of a piece of athletic equipment 104 of interest, there may be a desire to correlate movements of pieces of athletic equipment 104 to activity metrics based on a predetermined correlation stored in a data structure. With reference to FIG. 12, in such an embodiment, the individual 10 may use the sensor module 102 in the motion monitoring system 100 to determine such correlations to athletic equipment 104 movement according to movement correlation process 420 as follows.

First, at step 422, the sensor module 102 may detect movement of the piece of athletic equipment 104. This step may be carried out in a similar fashion to step 402 of the spatial orientation process 400, as described above.

If the monitored object 104 is a soccer ball 106, the detected movement may consist of the soccer ball 106 rolling on the ground as a result of being dribbled by the individual 10.

In some embodiments, the sensor module 102 may then determine that the movement of the piece of athletic equipment 104 indicates the occurrence of a movement to track. If the monitored piece of athletic equipment 104 is a soccer ball 106, the movement of the soccer ball 106 as a result of the individual 10 swiftly kicking the soccer ball 106 with their foot 12 in an attempt to make a goal may result in a determination that the motion of the soccer ball 106 in response to the kick—which could include motion of the soccer ball 106 before, during, and/or after the determination was made—should be tracked.

Next, at step 424, the sensor module 102 may record movement data in response to identifying a movement to track. In one embodiment, movement of the piece of athletic equipment 104 is recorded based on acceleration data captured by the acceleration sensor 118 of the sensor module 102. In another embodiment, movement of the piece of athletic equipment 104 is recorded based on magnetic field data captured by the magnetic field sensor 120 of the sensor module 102. In yet another embodiment, movement of the piece of athletic equipment 104 is recorded based on both acceleration data and magnetic field data.

If the monitored piece of athletic equipment 104 is a soccer ball 106, the movement of the soccer ball 106 as a result of the individual 10 swiftly kicking the soccer ball 106 may be recorded.

Next, at step 426, the sensor module 102 may determine a correlation between the recorded movement data and an activity metric. In one embodiment, this determination may be based on correlation information stored in a data structure, such as a lookup table.

A lookup table is a data structure, usually an array or associative array, often used to replace a runtime computation with a simpler array indexing operation. The savings in terms of processing time can be significant, since retrieving a value from memory is often faster than undergoing relatively processing-expensive computation or input/output operation. Lookup table figures may be pre-calculated and stored in static program storage or pre-fetched as part of a program initialization phase.

The nature of the correlation may depend on the particular application and algorithms used to establish the correlation. Also, the nature of the activity metric may change based on the athletic activity that the individual 10 is participating in, as well as particular piece of athletic equipment 104 that is being monitored. In one embodiment, the activity metric may relate to, for example, a launch angle, a rate of rotation, a ball trajectory, a speed, a jump height, a jump force, a jump distance, a jump trajectory, a kick force, a kick distance, an impact force, an impact location, a characterization of a specific type of athletic movement, or a reaction time measurement. In other embodiments, the activity metric may be, for example, the rate of rotation, the plane of rotation, the jump force, force profile (force acting upon the body of the athlete or the ground or the object), stroke information in tennis, swing profile in golf, baseball, hockey stick, kick profile of a leg or foot 12, angle position of a bike pedal, power output of a cyclist, fatigue (tremors starting to occur in repeated motion, i.e., running, lifting swimming, rowing etc.), posture, throwing or arm swing technique, and shooting technique.

If the monitored piece of athletic equipment 104 is a soccer ball 106, the correlation between the recorded movement data and an activity metric may rely on correlation data stored in a data structure that was derived from a function that expresses a relationship between soccer ball 106 acceleration data and soccer ball 106 launch speed metrics. In some embodiments, the function underlying the relationship between soccer ball 106 acceleration data and soccer ball 106 launch speed may be based on empirical data for the specific model soccer ball 106.

Finally, at step 428, an output is provided that conveys the activity metric to the individual 10, a coach, a teammate, a spectator, or any other interested person. This step may be carried out in a similar fashion to step 410 of the spatial orientation process 400, as described above.

The analytical frameworks outlined with respect to FIG. 9 and FIG. 12 detailing the basic spatial orientation process 400 and the basic movement correlation process 420, respectively may be used in embodiments of the present invention to monitor a piece of athletic equipment 104 using a sensor module 102. However, in some embodiments of the present invention, these basic analytical frameworks may include additional steps that may provide improved capabilities, thus offering the individual 10 engaged in athletic activities better tools to assess their activities.

Figure 13:
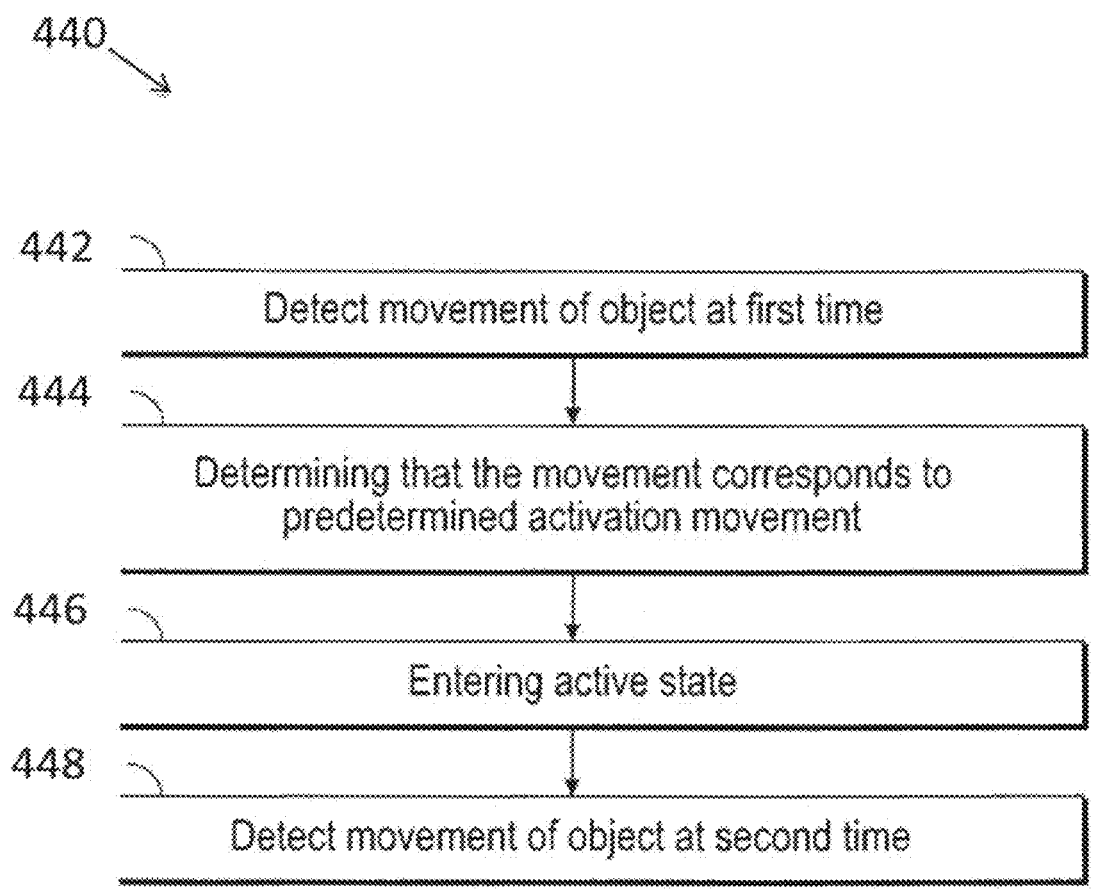
FIG. 13 is flow chart illustrating a method for determining an activity metric according to an embodiment of the present invention.

FIG. 13 illustrates an active state process 440 that may be used to augment the basic spatial orientation process 400 or the basic movement correlation process 420 outlined above. The active state process 400 may enable a sensor module 102 to run in a plurality of states, one of which may be considered an active state. In one embodiment, the active state may be characterized by the sensor module 102 consuming more power during the active state than prior to the active state. In another embodiment, the active state may be characterized by the sensor module 102 sampling data from the acceleration sensor 118 at a higher rate during the active state than prior to the active state. In yet another embodiment, the active state may be characterized by the sensor module 102 permanently saving data in the active state, as opposed to only temporarily recorded data prior to the active state. In this way, enabling various states may allow the sensor module 102 to operate with reduced battery power, reduced processing power, or otherwise be more efficient.

With reference to FIG. 13, the active state process 440 begins as step 442. In one embodiment, the steps of the active state process 440 may occur just prior to the steps of the basic spatial orientation process 400 or the basic movement correlation process 420 so that these processes may be carried out with more efficient sensor module 102 function.

At step 442, the sensor module 102 may detect movement of the piece of athletic equipment 104 at a first time. This step may be carried out in a similar fashion to step 402 of the spatial orientation process 400 or step 422 of the movement correlation process 420, as described above.

If the monitored piece of athletic equipment 104 is a soccer ball 106, the detected movement may consist of the soccer ball 106 rolling on the ground as a result of being dribbled by the individual 10.

Next, at step 444, the sensor module 102 may determine that the movement of the piece of athletic equipment 104 corresponds to a predetermined activation movement. In some embodiments, the predetermined activation movement may include a series of discrete movements such as, for example, a ball being bounced three times in series, the ball being thrown a predetermined height, the ball being kicked with a certain level of force, or a movement that results in the acceleration of the sensor module 102 exceeding and/or falling below a predetermined threshold in absolute terms or for a predetermined period of time. In one embodiment, movement of the piece of athletic equipment 104 is detected based on acceleration data captured by the acceleration sensor 118 of the sensor module 102. In another embodiment, movement of the object 104 is detected based on magnetic field data captured by the magnetic field sensor 120 of the sensor module 102. In yet another embodiment, movement of the object 104 is detected based on both acceleration data and magnetic field data.

The step of determining that the movement of the piece of athletic equipment corresponds to a predetermined activation movement may include comparing acceleration data associated with the predetermined activation movement to acceleration data detected in association with the movement of the piece of athletic equipment. Alternatively, the step of determining that the movement of the piece of athletic equipment corresponds to a predetermined activation movement may include comparing timing data associated with the predetermined activation movement to timing data detected in association with the movement of the piece of athletic equipment.

If the monitored piece of athletic equipment 104 is a soccer ball 106, the predetermined activation movement could be, for example, movement of the soccer ball 106 after it had been stationary for a predetermined period of time, the soccer ball 106 being bounced three times, the soccer ball 106 being thrown into the air a certain height of period of time, or a variety of other possible activation movements.

In some embodiments, the monitored piece of athletic equipment 104 can be considered stationary when the sensor module 102 of the monitored piece of athletic equipment 104 senses resultant acceleration of about 1 G (i.e., resultant acceleration within a threshold tolerance of 1 G, for example, within 5% of 1 G). In some embodiments the monitored piece of athletic equipment 104 can be considered stationary at times while being handled by an individual 10. For example, a basketball can be stationary for a period of time in which a basketball player takes a jump shot with ball (e.g., before release of ball from the hands of the individual 10, the ball can be considered stationary, where resultant acceleration sensed by sensor module 102 is about 1 G). Also for example, the ball can be stationary for a period of time in which a baseball player performs a throw of ball (e.g., a period of time spanning the transition from rearward motion to forward motion of the individual's 10 throwing motion, where resultant acceleration sensed by sensor module 102 is about 1 G).

Next, at step 446, after determining that an activation movement has occurred, the sensor module 102 may enter the active state. As previously described, the active state may be characterized, for example, by the sensor module 102 consuming more power or sampling data at a higher rate during the active state than prior to the active state.

Finally, at step 448, upon the sensor module 102 entering the active state, detection of movement of the piece of athletic equipment at a second time, as detailed at step 402 of the basic spatial orientation process 400 or at step 422 of the basic movement correlation process 420. In this way, enabling various states may allow the sensor module 102 to operate with reduced battery power, reduced processing power, or otherwise be more efficient.

Figure 14:
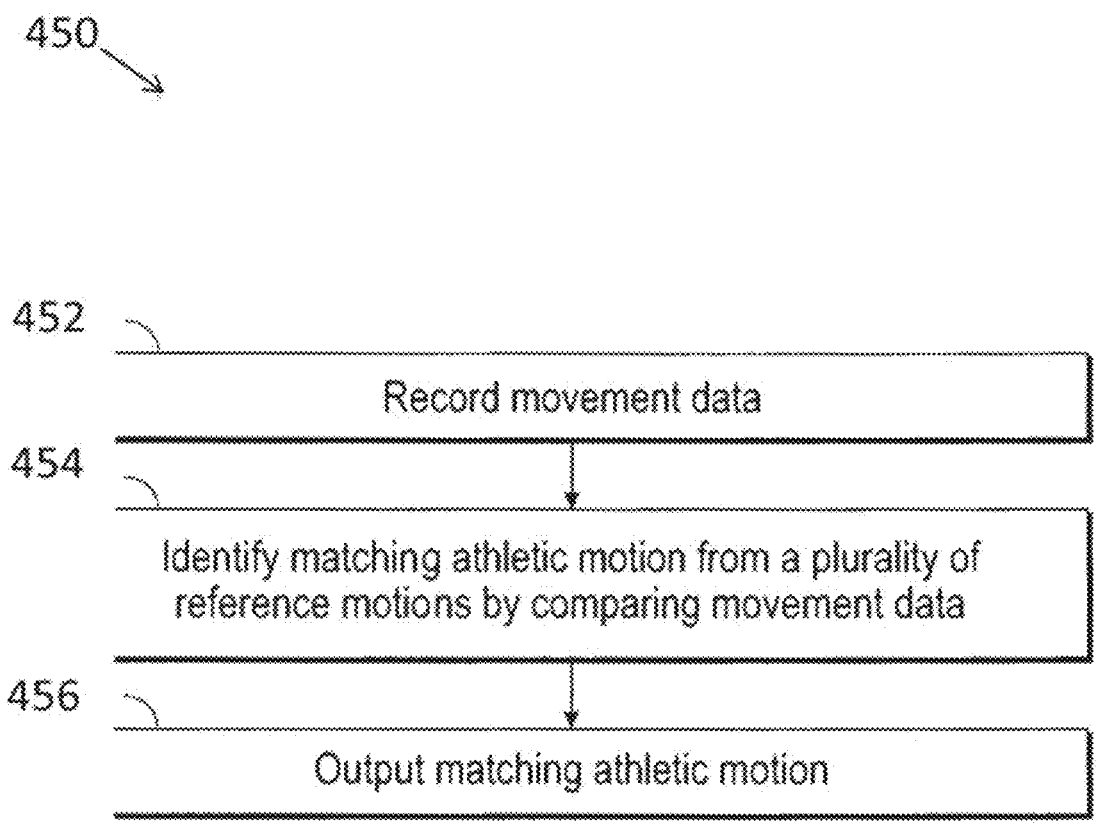
FIG. 14 is flow chart illustrating a method for identifying a matching athletic motion according to an embodiment of the present invention.

FIG. 14 illustrates a reference motion process 450 that may be used to augment the basic movement correlation process 420 outlined above. The reference motion process 450 may enable a sensor module 102 to identify a matching athletic motion from a plurality of reference motions by comparing movement data, where the plurality of reference motions may be diverse in nature. In this way, the athletic motion identification capabilities of the movement correlation process 420 may be enhanced by enabling identification and tracking of diverse types of motions executed during an activity.

With reference to FIG. 14, the reference motion process 450 begins as step 452. In one embodiment, the steps of the reference motion process 450 may effectively be substituted for step 426, 428, and 430 of the basic movement correlation process 420 outlined above so that the correlation and identification capabilities are enhanced.

At step 452, the sensor module 102 may record movement data (possibly in response to identifying a movement to track in a previous step, as outlined above). In one embodiment, movement of the piece of athletic equipment 104 is recorded based on acceleration data captured by the acceleration sensor 118 of the sensor module 102. In another embodiment, movement of the piece of athletic equipment 104 is recorded based on magnetic field data captured by the magnetic field sensor 120 of the sensor module 102. In yet another embodiment, movement of the piece of athletic equipment 104 is recorded based on both acceleration data and magnetic field data.

If the monitored piece of athletic equipment 104 is a soccer ball 106, the movement of the soccer ball 106 as a result of the individual 10 swiftly kicking the soccer ball 106 with their foot 12 may be recorded.

Next, at step 454, the sensor module 102 may identify a matching athletic motion from a plurality of reference motions by comparing the movement data to data associated with the plurality of reference motions. In one embodiment, as with step 428 of the basic movement correlation process 420, the identification may be made at least in part based on correlation information stored in a data structure, such as a lookup table.

Particular to step 454, identification of the matching athletic motion may be by reference to a plurality of reference motions. In other words, at step 454, the system is not limited to looking for a motion that matches a single motion (e.g., kicking a soccer ball 106 in an effort to score a goal). In some embodiments, the system is not limited to looking for a motion that matches a single class of motions (e.g., offensive soccer motions). In other embodiments, the system is not limited to looking for a motion that matches motions in a single sport (e.g., soccer motions). Alternatively, when the activity is a team sport, the matching athletic motion may be a motion commonly executed by a person during that team sport.

In one embodiment, one or more of the reference motions may include a series of discrete movements. In some embodiments, data associated with the plurality of reference motions may include acceleration data, magnetic field data, and/or timing data. Of course, the nature of the identifying matching athletic motion may depend on the particular application and algorithms used to establish the match. Also, the nature of the matching athletic motion may change based on the athletic activity that the individual 10 is participating in, as well as particular piece of athletic equipment 104 that is being monitored. In one embodiment related to basketball, the matching athletic motion may be, for example, a pass motion, an shot motion, an jump-shot motion, a dunk motion, a post-up motion, a cross-over dribble motion, a shot blocking motion, a steal motion, or a rebound motion.

Finally, at step 456, an output is provided that conveys the matching athletic motion to the individual 10, a coach, a teammate, a spectator, or any other interested person. This step may be carried out in a similar fashion to step 428 of the movement correlation process 420, as described above. In this way, the athletic motion identification capabilities of the movement correlation process 420 may be enhanced by enabling identification and tracking of diverse types of motions executed during an activity.

In other embodiments of the present invention, these above-described analytical frameworks may include additional steps that may provide additional capabilities, thus offering the individual 10 engaged in athletic activities additional tools to assess their activities. Exemplary additional analytical frameworks are disclosed in commonly owned U.S. patent application Ser. No. 13/446,982, filed Apr. 13, 2012 (which published as U.S. Patent App. Pub. No. 2013/0274040), the entirety of which is incorporated herein by reference thereto.

By using the motion monitoring system 100 including the sensor module 102 described above, embodiments of the present invention may advantageously enable the individual 10 (or their coach, teammate, or a spectator) to obtain this or other information about the motion of a piece of athletic equipment 104 during or after the course of the athletic activity.

While various embodiments of the present invention are described in the context of the sports of soccer (i.e., football), the present invention is not so limited and may be applied in a variety of different sports or athletic activities including, for example, baseball, basketball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

For baseball, sensor module 102 embodiments such as those described above may enable an individual 10, coach, teammate, or a spectator to determine, for example, characteristics of a pitcher's pitch, a batter's swing, or the ball's movement after it is thrown or before it is hit. For example, a sensor module 102 could be used to determine the type of pitch thrown (fastball, curveball, slider, change-up, etc.), the speed of a pitch, the trajectory of the pitch, or the total pitch count. A sensor module 102 could also be used to determine the type of swing (e.g., regular swing, bunt, swing that connects with the ball, swing that misses the ball, etc.), the speed of the swing, the swing count, the type of hit (grounder, line-drive, fly ball, homerun, etc.), the trajectory of the ball after it was hit, the distance that the ball was hit, or the location of the impact between the ball and the bat. In some embodiments the sensor module 102 may be mounted, for example, on a pitcher's torso, arm, hand, or finger, on a batter's torso, arm, hand, or finger, on or in the ball, or on or in a bat.

For bowling, sensor module 102 embodiments such as those described above may enable an individual 10, coach, teammate, or a spectator to determine, for example, characteristics of a bowler's release or the ball's path. For example, a sensor module 102 could be used to determine the type of spin applied to the roll, the speed of a roll, the total roll count, the force applied to the pins at the moment of impact, the location or occurrence of divots of slick spots on the lane, or the location of the impact between the ball and a pin. A sensor module 102 could also be used to determine the path of the ball after a release. In some embodiments the sensor module 102 may be mounted, for example, on a bowler's torso, arm, hand, or finger, or on or in the ball.

For boxing, sensor module 102 embodiments such as those described above may enable an individual 10, coach, teammate, or a spectator to determine, for example, characteristics of a boxer's offensive or defensive moves. For example, a sensor module 102 could be used to determine the type of punch thrown by a boxer (jab, hook, upper-cut, etc.), whether the boxer's left or right hand was used, the speed of the punch, whether the punch connected, the location of the impact between a boxer's glove and his opponent's body, and/or the total punch count. A sensor module 102 could also be used to determine whether a boxer dogged left, right or down, blocked a punch, was knocked down, or how many punches the boxer took. In some embodiments the sensor module 102 may be mounted, for example, on a boxer's torso, arm, hand, or finger, or on or in their boxing glove.

For cycling, sensor module 102 embodiments such as those described above may enable an individual 10, coach, teammate, or a spectator to determine, for example, characteristics of a biker's or bike's motion. For example, a sensor module 102 could be used to determine the speed of the bike, the nature of the turns, the nature of the elevation changes during a route, or jump characteristics such as airtime, the type of trick performed, or whether a trick was successfully performed. In some embodiments the sensor module 102 may be mounted, for example, on a biker's torso, arm, hand, leg, foot 12, or head, or on or in their bike at a location such as, for example, the handlebars, frame, or pedals.

For football (i.e., American football), sensor module 102 embodiments such as those described above may enable an individual 10, coach, teammate, or a spectator to determine, for example, characteristics of an offensive, defensive, or special teams player's movements, or the movement of the ball itself. For example, a sensor module 102 could be used to determine the type of run, pass, kick, or tackle, the number or runs, passes, kicks, or tackles, the force or a run, pass, kick, or tackle, the type of move used by a running back (e.g., spin move, stiff arm, hurdle, dive, sprint, etc.), or the distance, hang time, or rotational characteristics of a pass or kick. In some embodiments the sensor module 102 may be mounted, for example, on a player's torso, arm, or leg, or on or in the ball.

For golf, sensor module 102 embodiments such as those described above may enable an individual 10, coach, teammate, or a spectator to determine, for example, characteristics of a golfer's swing or the motion of the ball after it is hit. For example, a sensor module 102 could be used to determine the type of swing (drive, fairway shot, approach shot, putt) the swing speed, the swing quality, or a swing count, which could in turn be used to coach a golfer on how to improve their swing or game play. A sensor module 102 could also be used to determine the path of the ball (straight, slice, hook, low, high, breaking left, breaking right), the distance of a shot, or the location of the impact between the ball and a club head. In some embodiments the sensor module 102 may be mounted, for example, on a golfer's torso, arm, hand, leg, foot 12, or head, or on or in the ball, or on or in a club.

For hockey, sensor module 102 embodiments such as those described above may enable an individual 10, coach, teammate, or a spectator to determine, for example, characteristics of a player's shot or pass or the motion of the puck after it is contacted. For example, a sensor module 102 could be used to determine the type of shot (e.g., slap shot, backhand shot), the shot speed, the shot quality, or a shot or pass count. A sensor module 102 could also be used to determine the path of the puck toward the goal (straight, left, right, low, high,) or the location of the impact between the puck and the stick head. In some embodiments the sensor module 102 may be mounted, for example, on a hockey player's torso, arm, hand, leg, foot 12, or head, or on or in the puck, or on or in a stick.

For running, sensor module 102 embodiments such as those described above may enable an individual 10, coach, teammate, or a spectator to determine, for example, characteristics of a runner's motion. For example, a sensor module 102 could be used to determine the speed, pace, distance traversed, locations traversed, or to discriminate between different surfaces (e.g., grass, street, or trail) and inclinations (e.g., uphill, flat, or downhill). In some embodiments the sensor module 102 may be mounted, for example, on a runner's torso, arm, hand, leg, foot 12, or head, or on or in their article of footwear.

For skiing, sensor module 102 embodiments such as those described above may enable an individual 10, coach, teammate, or a spectator to determine, for example, racecourse statistics or information on when certain tricks are successfully performed. For example, a sensor module 102 could be used to determine how many gates a skier successfully traverse on a race course, the skier's speed, or the angles of their turns. Also, a sensor module 102 could be used to determine maneuvers such as jumps, flips, rotations, or the degree of the actions that makeup the maneuvers (e.g., height of jump, degrees of rotation, hang-time, type of trick performed, etc.). In one embodiment, sensor module 102 may be mounted on a top or bottom surface of a ski, contained within a ski, or placed in a void in the ski, in a releasable or non-releasable manner, or mounted to the skier's boot, body, or in or on other clothing. In other embodiments, sensor modules 102 could similarly be used for snowboarding or other similar winter sports activities involving similar winter sports equipment.

For tennis, sensor module 102 embodiments such as those described above may enable an individual 10, coach, teammate, or a spectator to determine, for example, characteristics of a player's swing or the motion of the ball after it is hit. For example, a sensor module 102 could be used to determine the type of swing (forehand, backhand, serve, return, lob) the swing speed, the swing quality, or a swing count. A sensor module 102 could also be used to determine the motion of the ball (straight, topspin, backspin, left spin, or right spin), the distance of a shot, or the location of the impact between the ball and the racquet head. In some embodiments the sensor module 102 may be mounted, for example, on a player's torso, arm, hand, leg, foot 12, or head, or on the tennis ball, or on a racquet.

For skateboarding, sensor module 102 embodiments such as those described above may enable an individual 10, coach, teammate, or a spectator to determine, for example, when certain tricks are successfully performed, such as ollies, aerials, flip tricks (e.g., kickslips), slides, or grinds, or the degree of the actions that makeup the tricks (e.g., height of jump, rate of rotation, length of time of slide, etc.). In one embodiment, the sensor module 102 may be mounted on the underside of the skateboard, in a void between a skateboard wheel axle (i.e., truck) and the skateboard itself. In other embodiments, the sensor module 102 may be coupled to a top or bottom surface of the board, contained within the board, or coupled to a wheel axle (i.e., truck) in a releasable or non-releasable manner.

For surfing, sensor module 102 embodiments such as those described above may enable an individual 10, coach, teammate, or a spectator to determine, for example, when certain maneuvers are successfully performed, such as, for example, riding waves, executing turns or cutbacks, carving, floating, or tube riding. In one embodiment, the sensor module 102 may be mounted on a top or bottom surface of the surfboard, contained within the surfboard, or placed in a void in the surfboard, in a releasable or non-releasable manner.

In various embodiments of the present invention described above, an individual 10 (or another interested person such as a coach, teammate, or spectator) may obtain information about the motion of a piece of athletic equipment 104 during the course of the athletic activity. Once an activity metric or specific athletic movement has been identified by the monitoring system 100, to the extent that the activity metric or specific athletic movement was not entirely optimal/correct, the system 10 may further be employed to train or coach the individual 10 to improve their activity metric or specific athletic movement in the future. Determinations of what activity metric value or specific athletic movement characteristic is optimal/correct may be made automatically by the system 10 based on predetermined values, algorithms, or other data stored in a database, look-up table, or the like, or the determination may be made by a live trainer, coach, the individual 10 themselves, or another interested person with access to the activity metric value or specific athletic movement data.

For example, in embodiments where the monitored piece of athletic equipment 104 is a soccer ball 106, where the change in the spatial orientation of the soccer ball 106 resulting from a kick is used to determine, for example, a launch angle of the soccer ball 106, a rate of rotation of the soccer ball 106, launch speed, estimated speed, the location of the foot's 12 impact on the soccer ball 106, or similar metrics, these determinations may be used by the system 10 to help the individual 10 improve their foot-ball impact, launch angle, rate of rotation, or launch speed in future kicks. Methods used to achieve improvements may be, for example, providing cross-training workouts or drills to the individual 10, providing soccer-specific workouts or drills to the individual 10, or prescribing a number of other training regimens.

Exemplary systems for calibrating data sensed by a sensor module 102 are disclosed in commonly owned U.S. patent application Ser. No. 13/446,982, filed Apr. 13, 2012 (which published as U.S. Patent App. Pub. No. 2013/0274040), the entirety of which is incorporated herein by reference thereto.

Individual 10 or another person may desire to know activity metrics of a sport ball 106, for example, to learn the effects that actions of individual 10 have on sport ball 106, such as a kick or throw of the sport ball 106 by the individual 10. Motion monitoring system 100 may determine activity metrics such as trajectory of sport ball 106, launch angle of sport ball 106, rotation rate of sport ball 106, orientation of rotation plane of sport ball 106, orientation of rotation axis of sport ball 106, travel speed of sport ball 106, launch speed of sport ball 106, force of a kick or other impact on sport ball 106, distance of travel of sport ball 106, and maximum acceleration of sport ball 106. Sensor module 102 may output data representative of such activity metrics, such as to a display device of personal computer 304 or portable electronic device 306. Such data may be outputted from sensor module 102 in raw form (e.g., unprocessed signals from acceleration sensor 118 and/or magnetic field sensor 120) or in representative form (e.g., data that results from processing signals from acceleration sensor 118 and/or magnetic field sensor 120). In some embodiments, monitoring system 100 outputs a representation of one or more activity metrics in a manner perceivable by individual 10 and/or another person.

As noted herein, in some embodiments motion monitoring system 100 can determine and/or output a representation of instantaneous trajectory of a sport ball 106 over a period of time or at a particular point in time, the instantaneous trajectory being a representation of the direction of motion of sport ball 106 in motion.

In some embodiments, motion monitoring system 100 can determine and/or output a representation of launch angle of sport ball 106. In some embodiments, launch angle can be determined to correspond to instantaneous trajectory of sport ball 106 at a point in time sufficiently close to initiation of motion of sport ball 106, such as shortly after sport ball 106 has been kicked or hit. In some embodiments, initiation of motion of sport ball 106 is determined based on a sensed impulse acceleration exceeding a threshold. In some embodiments, launch angle can be determined to correspond to instantaneous trajectory of sport ball 106 less than 150 ms (e.g., 100 ms to 150 ms) after initiation of motion of sport ball 106. In some embodiments, launch angle can be determined to correspond to instantaneous trajectory of sport ball 106 at the earliest time after initiation of motion of sport ball 106 at which acceleration magnitude can be sensed.

In some embodiments, this time may immediately follow a period of less reliable data output by acceleration sensor 118, where such data output is less reliable than data output by acceleration sensor 118 at other times. Such less reliable data output may be the result of, for example, a disturbance (e.g., railing) in sensed acceleration data (e.g., due to sudden change in acceleration, for example, upon an impact) or gain saturation of the acceleration sensor signal (e.g., a period during which the acceleration sensor outputs its maximum acceleration signal, because acceleration is higher than the maximum acceleration it can sense), which may result from, for example, the high initial acceleration of sport ball 106 in reaction to an impact (e.g., a kick, a throw, a shot). In some embodiments, such less reliable acceleration data output may be experienced for a time (e.g., 100-150 ms) after impact of a kick (e.g., about 10 ms for the duration of kick impact, and about 90 ms to 140 ms after impact).

Launch angle can correspond to instantaneous trajectory as the angle of the vertical component of the direction of travel of a sport ball 106 in free flight sufficiently close to initiation of motion of sport ball 106. In some embodiments, free flight is determined based on acceleration data. Immediately upon entering free flight (e.g., upon sport ball 106 being thrown or kicked), acceleration data sensed by acceleration sensor 118 shows resultant acceleration of less than 1 G (i.e., less than the acceleration due to gravity). For example, resultant acceleration may drop from 1 G (e.g., in a stationary or non-free flight state) to 0.5 G (e.g., in free flight). The time at which this drop takes place can be determined as the initiation of free flight. Continued free flight can be determined while resultant acceleration remains below 1 G. In some embodiments, the magnitude of acceleration due to gravity can be predefined, or can be determined based on acceleration data sensed while sport ball 106 is stationary.

The closer to initiation of motion that the angle of the vertical component of the direction of travel of sport ball 106 in free flight is determined, the more representative of launch angle it may be. Beyond initiation of motion, the angle of the vertical component of the direction of travel of sport ball 106 in free flight may change (e.g., decrease). In some embodiments, this change can be compensated for using a formula based on the instantaneous trajectory, speed, and time (after initiation of motion), to increase the accuracy of the launch angle determination. In some embodiments, the path of sport ball 106 during a period of gain saturation (i.e., while the acceleration sensor is railed) can be determined based on magnetic field data sensed during that time. In some embodiments the launch angle at the moment of impact can be determined based on this path.

In some embodiments, instantaneous trajectory and/or launch angle of sport ball 106 can be determined based on one or more of acceleration data and magnetic field data (e.g., sensed by acceleration sensor 118 and/or magnetic field sensor 120) at a first, earlier time, and one or more of acceleration data and magnetic field data (e.g., sensed by acceleration sensor 118 and magnetic field sensor 120) at a second, later time. In some embodiments, at the first time sport ball 106 is stationary, and at the second time sport ball 106 is in motion (e.g., motion of sport ball 106 is initiated between the first time and the second time).

Exemplary systems for determining instantaneous trajectory and launch angle of a sport ball 106 are disclosed in commonly owned U.S. patent application Ser. No. 13/446,982, filed Apr. 13, 2012 (which published as U.S. Patent App. Pub. No. 2013/0274040), the entirety of which is incorporated herein by reference thereto.

It is known that the direction of motion of a moving body is opposite to the direction of drag force applied to the moving body. In some embodiments monitoring system 100 determines the relative (i.e., with respect to sensor module 102) direction of motion of sport ball 106 to be opposite to the direction of resultant acceleration vector.

In some embodiments, to determine the absolute (i.e., with respect to the external coordinate system) direction of motion of sport ball 106 (e.g., instantaneous trajectory), monitoring system 100 subtracts the angle of rotation of sport ball 106 between the first time and the second time from the relative direction of motion of sport ball 106.

In some embodiments, to determine launch angle of sport ball 106, monitoring system 100 determines the angle of the vertical component of the absolute direction of motion of sport ball 106, which is determined to correspond to launch angle of sport ball 106.

As noted herein, in some embodiments monitoring system 100 can determine and/or output a representation of rotation rate of sport ball 106. Rotation rate is a measure of the angular velocity ($\omega$) at which sport ball 106 rotates, and can be expressed, for example, as the number of revolutions of sport ball 106 per unit time, or the angular change of sport ball 106 per unit time.

In some embodiments, to determine rotation rate of sport ball 106, sensor module 102 of rotating sport ball 106 can sense acceleration data via acceleration sensor 118 at a first time and at a second time. Between the first time and the second time, sport ball 106 (including sensor module 102) rotates. Acceleration data sensed at the first time and the second time is a resultant acceleration vector created due to drag forces acting on sport ball 106. In some embodiments, monitoring system 100 normalizes the resultant acceleration vector at each of the first time and the second time (e.g., so that the resultant acceleration vector is between −1 and 1). Such normalization can provide a true orientation in space of the resultant acceleration vector. This normalization is performed on data from all (e.g., all three) axes of acceleration sensor 118 (such that the sum of the squares of the normalized values will always be 1). In some embodiments, monitoring system 100 determines the angle of each axis at the first time and at the second time by denormalizing the magnitude of the normalized value (e.g., calculating the cosine or arccosine of the value). In some embodiments, monitoring system 100 determines the change in each angle between the first time and the second time. In some embodiments, monitoring system 100 determines the rate of rotation based on the change in angle between the first time and the second time and the elapsed time between the first time and the second time.

In some embodiments, to determine rotation rate of sport ball 106, sensor module 102 of rotating sport ball 106 can sense acceleration data via acceleration sensor 118 for a period of time. In some embodiments, monitoring system 100 can identify a repeating portion of the sensed acceleration data (e.g., the orientation of acceleration with respect to sensor module 102). In some embodiments, monitoring system 100 can identify a repeating portion of the sensed acceleration data by identifying successive similar orientations of such acceleration data (e.g., repeating peaks in data output representative of the orientation of acceleration) with respect to sensor module 102. In some embodiments, monitoring system 100 can determine the time period of a repeating portion of sensed acceleration data (e.g., the elapsed time between successive similar orientations of such acceleration data), which can represent the time period for a single revolution of sport ball 106. In some embodiments, monitoring system 100 can calculate the inverse of the time period for a single revolution of sport ball 106 and can determine this value to be the rotation rate of sport ball 106.

As noted herein, in some embodiments motion monitoring system 100 can determine and/or output a representation of the orientation of rotation of sport ball 106, which may be represented the angle of the axis of rotation of sport ball 106 and/or the angle of the plane of rotation of sport ball 106. Axis of rotation is an axis through sport ball 106 about which sport ball 106 rotates. Plane of rotation is a plane orthogonal to axis of rotation. In some embodiments, angles can be determined based on acceleration data sensed by acceleration sensor 118 and magnetic field data sensed by magnetic field sensor 120.

In some embodiments, monitoring system 100 can determine one or both of angles by sensing orientation of resultant acceleration vector with respect to sensor module 102 at a first time (e.g., $t_1$) and at a second time (e.g., $t_2$, where the second time may be 20-30 ms after the first time). In some embodiments, monitoring system 100 can determine the orientation (with respect to sensor module 102) of the plane defined between the orientation of resultant acceleration vector with respect to sport ball 106 at the first time and the orientation of resultant acceleration vector with respect to sport ball 106 at the second time. In some embodiments, monitoring system 100 can define this plane to be the plane of rotation of sport ball 106. In some embodiments, monitoring system 100 can determine the angle between plane of rotation and the orientation of gravity vector with respect to sensor module 102. In some embodiments, monitoring system 100 can calculate angles based on the angle between plane of rotation and the orientation of gravity vector using, for example, trigonometric calculations.

As noted herein, in some embodiments monitoring system 100 can determine and/or output a representation of travel speed of sport ball 106. Speed is a measure of the rate of change of the position of sport ball 106, and can be expressed as the magnitude of a velocity vector of sport ball 106. Speed of sport ball 106 can be determined based on acceleration data sensed by acceleration sensor 118 while sport ball 106 is in motion. Speed of sport ball 106 can be determined for any time sport ball 106 is in free flight. In some embodiments, speed is calculated shortly after initiation of motion (e.g., 50 ms after being kicked) in order to determine a near-maximum speed of sport ball 106 in response to the initiation of motion.

In some embodiments, sport ball 106 is determined to be in free flight at a given time. While in free flight, acceleration sensor 118 of sensor module 102 may sense magnitude of acceleration of sensor module 102, and thus sport ball 106, with respect to sensor module 102. The magnitude of acceleration can be expressed as the magnitude of a resultant acceleration vector. In some embodiments, the acceleration sensed by sensor module 102 is substantially entirely due to the effects of drag (i.e., deceleration due to a drag force) on sport ball 106.

It is known that the direction of motion of a moving body is opposite to the direction of drag force applied to the moving body. Thus, in some embodiments the magnitude of acceleration sensed by acceleration sensor 118 of sensor module 102 is the magnitude of acceleration in the direction of motion of sport ball 106. In some embodiments the magnitude of acceleration sensed by acceleration sensor 118 of sensor module 102 is determined to be the magnitude of acceleration in the direction of motion of sport ball 106.

Speed of sport ball 106 in motion can be expressed as a function of the magnitude of acceleration of sport ball 106. This functional relationship can be influenced by physical characteristics of sport ball 106 (e.g., mass, size, surface area, surface texture, material, shape, panel shape, moment of inertia), and thus may vary for sport balls 106 of different construction. This functional relationship can also be influenced by environmental conditions (e.g., ambient temperature, local pressure), indications of which may be received by monitoring system 100 from suitable environmental sensors (e.g., coupled to sport ball 106, incorporated into sensor module 102, coupled to a remote device) or input by an individual 10 via an interface of monitoring system 100 (e.g., an input of personal computer 304 or portable electronic device 306, such as, for example, a keyboard, microphone, or touchscreen). This functional relationship can also be influenced by dynamic characteristics of sport ball 106 such as, for example, rotation of sport ball 106 (e.g., rotation rate and/or rotation angle), which can impart a Magnus effect on sport ball 106, influencing its speed. A Magnus effect can cause a curve or bend in the trajectory of sport ball 106.

For a given sport ball 106 (and balls of the same or sufficiently similar construction), this functional relationship may be established by calculation (e.g., the relation between drag force and speed of a spherical object in free flight is speed=constant*log(drag)+constant), experimentation, or both, and may be expressed and/or stored as a data structure within monitoring system 100, for example, as an algorithm, as a graphical curve, or as a lookup table.

In some embodiments, the functional relationship can be established (or augmented) by an individual 10 of sport ball 106. For example, individual 10 may set sport ball 106 on the ground a distance from a wall or other object or structure. Individual 10 may input the distance into monitoring system 100 via an interface thereof. Individual 10 may then kick sport ball 106 at the wall with their foot 12. Sensor module 102 may sense the time of initiation of free flight of sport ball 106 as sport ball 106 is impacted by individual's 10 foot 12. Sensor module 102 may then sense the time sport ball 106 makes contact with the wall (e.g., by an abrupt change in resultant acceleration, such as a drop to about zero). The distance traveled divided by the time of travel can be used to determine a representation of the speed of sport ball 106 for the measured kick. Resultant acceleration (i.e., drag) can be sensed for the measured kick. Individual 10 may perform such operations multiple times, at the same or different distances, to establish an experimental data set, which can be used to derive a representation of the functional relationship between drag force and speed of the sport ball 106 in free flight. This representation of the functional relationship can be stored as a data structure within monitoring system 100 and subsequently referred to in order to determine speed of sport ball 106 based on measured acceleration data, as described above.

Once the magnitude of acceleration of sport ball 106 is sensed by acceleration sensor 118 of sensor module 102, monitoring system 100 compares the magnitude of acceleration of sport ball 106 to a data structure expressing the functional relationship between magnitude of acceleration and speed for the given sport ball 106, to determine speed of sport ball 106 (i.e., the speed that corresponds to the sensed acceleration magnitude in the data structure expressing the functional relationship).

A graphical curve and/or table can each be relied upon by monitoring system 100 to determine speed of sport ball 106, given the magnitude of acceleration of sport ball 106. For example, given a magnitude of acceleration of A, both graphical curve and table could show a speed of B, and given a magnitude of acceleration of C, both graphical curve and table could show a speed of D. In some embodiments, if a given value for magnitude of acceleration does not have a corresponding magnitude of acceleration in the expression of the functional relationship (e.g., graphical curve or table), the speed may be determined by known techniques of mathematical approximation, such as, for example, rounding or interpolation.

In some embodiments, monitoring system 100 can determine and/or output a representation of a flight time of sport ball 106. In some embodiments, flight time can be determined based on acceleration data. For example, flight time can correspond to a period during which acceleration data sensed by acceleration sensor 118 shows resultant acceleration of less than 1 G. For example, sensor module 102 may determine the time at which sport ball 106 enters free flight (e.g., monitoring system 100 may determine a flight initiation time corresponding to the time at which resultant acceleration drops below 1 G), may determine a flight termination time corresponding to the time at which resultant acceleration returns to 1 G, may calculate the elapsed time between the flight initiation time and the flight termination time, and may determine the elapsed time to be a flight time of sport ball 106.

In some embodiments, monitoring system 100 can determine and/or output a representation of distance of travel of sport ball 106. In some embodiments, monitoring system 100 can determine distance of travel of sport ball 106 for a flight of sport ball 106 based on acceleration data. In some embodiments, monitoring system 100 can determine distance of travel based on flight time of sport ball 106 (which can be determined as described above) and travel speed of sport ball 106 (which can be determined as described above) during the flight time (e.g., monitoring system 100 can determine the average speed of sport ball 106 during flight). For example, monitoring system 100 can determine distance of travel for a flight of sport ball 106 by multiplying average velocity during the flight by the flight time.

In some embodiments, monitoring system 100 can determine a trajectory model (i.e., path of flight) for an instance of free flight of sport ball 106, and may calculate the distance traversed by sport ball 106. In some embodiments, monitoring system 100 can determine the trajectory model based on conditions (e.g., activity metrics) of sport ball 106 (e.g., conditions at initiation of flight of sport ball 106, and/or at a point in time thereafter). In some embodiments, monitoring system 100 can determine the trajectory model based on speed of sport ball 106, launch angle of sport ball 106, rotation plane of sport ball 106, and rotation rate of sport ball 106, each of which can be determined, for example, as described herein. Monitoring system 100 can calculate the distance traveled by sport ball 106 based on the trajectory model (e.g., by calculating the distance between beginning and end points of the trajectory model along the ground, or a plane representing the ground). In some embodiments, because the trajectory model can be determined based on conditions before completion of a flight of sport ball 106, monitoring system 100 can determine a trajectory model for an instance of flight even in the event that free flight of sport ball 106 is interrupted (e.g., by striking an object). In such a case, monitoring system 100 can determine an estimated distance traveled by sport ball 106, which can correspond to a distance sport ball 106 would have traveled had its flight not been interrupted.

In some embodiments, monitoring system 100 can determine and/or output a representation of maximum acceleration of sport ball 106. In some embodiments, monitoring system 100 can determine maximum acceleration of sport ball 106 based on acceleration data. For example, monitoring system 100 can determine maximum acceleration of sport ball 106 in flight using acceleration data sensed by acceleration sensor 118 of sensor module 102. For example, monitoring system 100 can compare the magnitude of acceleration of sport ball 106 for a time period at all times during the period (or a subset thereof) for which data is available, to identify the greatest magnitude of acceleration, which can be determined to be the maximum acceleration of sport ball 106 during the time period. The time period for which maximum acceleration is determined can be any time period, for example, a single period of free flight, a selected time period, or the duration of an athletic contest. In some embodiments, monitoring system 100 is may filter out sensed magnitudes of acceleration of, around, or in excess of 1 G, as such magnitudes may be due to gravity (e.g., in the event sport ball 106 is not in free flight).

Monitoring system 100 can output representations of activity metrics, including, for example, trajectory of sport ball 106, launch angle of sport ball 106, rotation rate of sport ball 106, orientation of rotation plane of sport ball 106, orientation of rotation axis of sport ball 106, travel speed of sport ball 106, launch speed of sport ball 106, force of a kick or other impact on sport ball 106, impact location on the sport ball 106, distance of travel of sport ball 106, and maximum acceleration of sport ball 106, in a manner perceivable by individual 10 or other person (e.g., a coach, trainer, or spectator). Data generated within or received by any component of monitoring system 100 can be transmitted, processed, and output in any suitable manner, including those described herein.

For example, in some embodiments, representations of activity metrics can be output to a display of a portable electronic device (e.g., portable electronic device 306) or personal computer (e.g., personal computer 304). In some embodiments, monitoring system 100 can determine and output, for example, representations of activity metrics in real time, representations of past activity metrics, representations of predicted activity metrics, representations of comparisons of a current (or most recent) value for an activity metric to a past value for that activity metric, representations of comparisons of one activity metric to a different activity metric, representations of comparisons of a value for an activity metric to a target value for the activity metric, representations of comparisons of a value for an activity metric of sport ball 106 or individual 10 to a value for the same (or a different) activity metric for a different sport ball 106 or individual 10.

In some embodiments, representations of activity metrics can be presented (e.g., displayed on a display screen of any of the devices described herein) as functions of one another, or of other variables. For example, travel distance of sport ball 106 can be presented as a function of launch angle. Also for example, activity metrics can be presented as a function of location (e.g., location on a playing field, proximity to a player, proximity to a goal), as a function of an event (e.g., scoring of a field goal, committing a foul), as a function of an environmental condition (e.g., ambient temperature, precipitation), or as a function of a physiological condition of an individual 10 (e.g., heart rate, body temperature). Information relating to such variables (e.g., location information, event information, environmental condition information, and physiological condition information) may be provided to monitoring system 10 from appropriate sensors incorporated therein, or from elements outside of monitoring system 100 that are in communication with monitoring system 100.

In some embodiments, monitoring system 100 can determine and output representations in any perceivable way, for example, numerically (e.g., by outputting a value indicative of the activity metric or comparison), textually (e.g., by outputting a word or phrase indicative of the activity metric or comparison), graphically (e.g., by outputting a graph or other image indicative of the activity metric or comparison), or tabularly (e.g., by outputting a table indicative of the activity metric or comparison).

In some embodiments, activity metrics can be output in a game-like manner.

Points or other positive or negative feedback may be determined and output based on values for activity metrics for sport ball 106 and/or individual 10. Comparisons based on such values or feedback can influence progress in the game. For example, such values or feedback may be compared to past values or feedback for the same individual 10 or sport ball 106, and improvement may result in positive progress being made in the game (e.g., a higher "level" being designated to a game account of individual 10 or sport ball 106). Also for example, such values or feedback may be compared to values or feedback of a different individual 10 or sport ball 106 (including data of, or purported to be of, a professional athlete or other well-known person), and progress in the game may be determined based on that comparison. Also for example, such values or feedback may be compared to target values or feedback, and progress in the game may be determined based on that comparison. Also for example, in some embodiments, such activity metrics can govern capabilities of a virtual player in a virtual game, by being uploaded to or otherwise accessed by the game (e.g., the maximum ball speed of an individual's 10 kick of sport ball 106 may limit the maximum virtual ball speed of a virtual avatar of the individual in a virtual game).

In some embodiments, a plurality of monitored individuals 10 may interact with one or more of sport balls 106 (e.g., during a soccer game). Activity metrics derived from each of the plurality of individuals 10 and activity metrics derived from ball(s) can be similarly compared, combined, and/or represented as described above. Such comparison, combination, and/or representations can be made based on each individual 10 considered separately, on a subset of individuals 10 grouped together (e.g., a team, midfielders of a team), or on all monitored individuals 10. In a game setting, such comparison, combination, and/or representations can be correlated to game events, such as a goal, a sport ball 106 traveling out-of-bounds, a penalty kick, or a jump ball, which can be output in relation to contemporaneous activity metrics of individuals 10 as described.

Such comparing, combining, and/or representing data derived from monitoring sport ball 106 and from monitoring individuals 10 interacting with sport ball 106 can provide benefits to, for example, the individuals 10 participating in an athletic activity, coaches, spectators, physicians, and game officials. Such persons may interact or work together during a session of athletic activity for a variety of reasons.

For example, it may be desired that a coach monitors the performance of the individuals 10 and makes recommendations or otherwise influences their performance in order to maximize the individuals' 10 fitness level. Alternatively or additionally, it may be desired that the coach monitors and influences the individuals 10 to help maximize the effectiveness of the individuals 10 in the athletic activity. Further, it may be desired that the coach monitors and influences the individuals 10 to help maximize the probability of success in the athletic activity (where success may be, for example, defeating an opposing team in a game, such as, for example, soccer, or achieving/maintaining a desired level of fitness for one or more individuals 10 participating in the athletic activity). A session of athletic activity may include, for example, a training session (e.g., a field session, a gym session, a track session) or a competitive session (e.g., a soccer match or a basketball game).

In some embodiments, the coach may monitor the individuals 10 and sport ball 106 and may provide feedback to the individuals 10 in order to track and maintain or improve the individuals' 10 health, safety, and/or performance.

In some embodiments, monitoring system 100 can be applied as described herein to a standalone sensor that can be affixed to any implement, including, for example, the objects described herein (e.g., as an aftermarket upgrade).

III. Exemplary Point-of-Impact Determination Embodiments

Building on the above description, a description of various exemplary methods of using the motion monitoring system 100 of the present invention to monitor changes in the spatial orientation or movement of a piece of athletic equipment 104, or to determine a correlation between soccer ball 106 movement data and point of impact 150 on a soccer ball 106, is now provided below.

Figure 15:
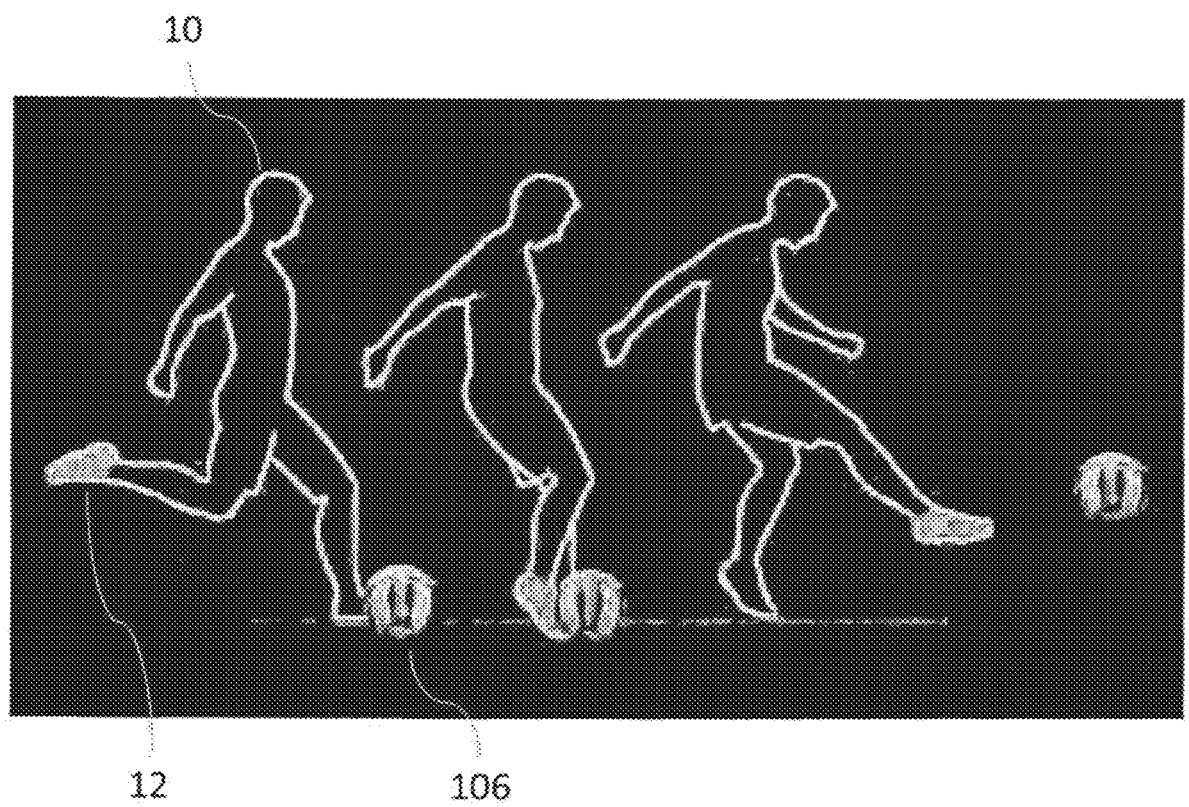
FIG. 15 is an illustration of an individual interacting with a sport ball according to an embodiment of the present invention.

As illustrated in FIG. 15, a soccer kick can involve a series of complex motions by an individual 10 leading up to the striking of the soccer ball 106 by the individual's 10 foot 12. Generally speaking, under ideal conditions when an individual 10 is attempting to kick a goal, the individual 10 may approach the soccer ball 106 by taking several steps toward the soccer ball 106. Depending on the nature of the kick, the individual 10 may approach the soccer ball 106 straight on with respect to the intended flight path of soccer ball 106, or may approach the soccer ball 106 at an angle with respect to the intended flight path of the soccer ball 106. Next, as illustrated in FIG. 15, it is often desirable for the individual 10 to land their "plant foot" (i.e. the foot 12 not kicking the soccer ball 106) to the side of and directly in the middle of the soccer ball 106, with the plant foot 12 pointing toward the intended target. The individual 10 then ideally keeps their head down and leans their body into the kick, swing their kicking foot 12 into the soccer ball 106 and continuing to follow through, as shown in FIG. 15.

Figure 16:
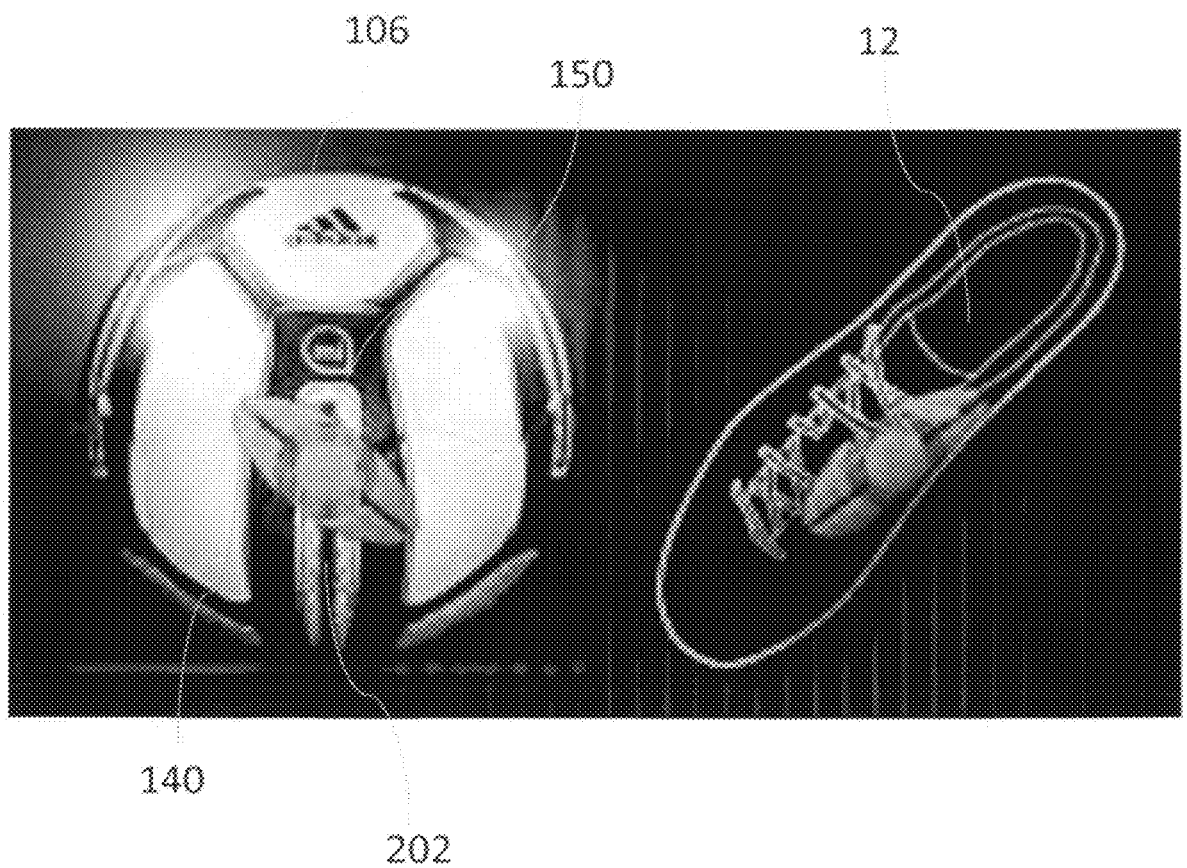
FIG. 16 is an illustration of a sport ball according to an embodiment of the present invention.

Depending on the intended flight path and other motion characteristics of the soccer ball 106, the individual 10 may need to utilize a particular approach and ball-striking mechanics. Soccer players know from experience that a relationship exists between the location of the point of impact between their foot 12 and a soccer ball 106 and motion characteristics of the soccer ball 106 during and after it is kicked. FIG. 16 illustrates an exemplary strike zone 140 and point of impact 150 on a soccer ball 106 resulting from a kick by an individual's 10 foot 12. When an individual 10 kicks a soccer ball 106, the impact typically results in deformation of both the individual's 10 foot 12 (or rather, the footwear covering their foot 12) and of the soccer ball 106. Deformation of the soccer ball 106 is more significant and visually apparent—a surface of the soccer ball 106 typically becomes indented or flattened in response to a sufficiently swift kick.

The strike zone 140 shown in FIG. 16 represents an area of the surface of the soccer ball 106 where contact with a portion of the individual's 10 foot 12 and/or deformation of the soccer ball 106 may occur during a kick. The point of impact 150 shown in FIG. 16 occurs within the bounds of the strike zone 140, and represents the location on the surface of the soccer ball 106 that approximately coincides with the center of the area of the foot 12 in contact with the soccer ball 106. Note that the point of impact 150 is in alignment with an exterior marking 202 of the soccer ball 106, as first described in connection with FIG. 5. Corresponding markings are illustrated on the foot 12 (encased in a soccer boot) in FIG. 16 to show an exemplary position on the foot 12 where the foot 12 may impact the soccer ball 106.

Embodiments of the present invention provide an analytical framework for analyzing motion characteristics of sport balls 106, such as a soccer ball 106, including analyzing the relationship between the location of the point of impact 150 between an individual's 10 foot 12 and a soccer ball 106 and motion characteristics of the soccer ball 106 during and after it is kicked. Examined motion characteristics include ball speed, ball spin rate, ball spin axis, and ball launch angle.

Figure 17:
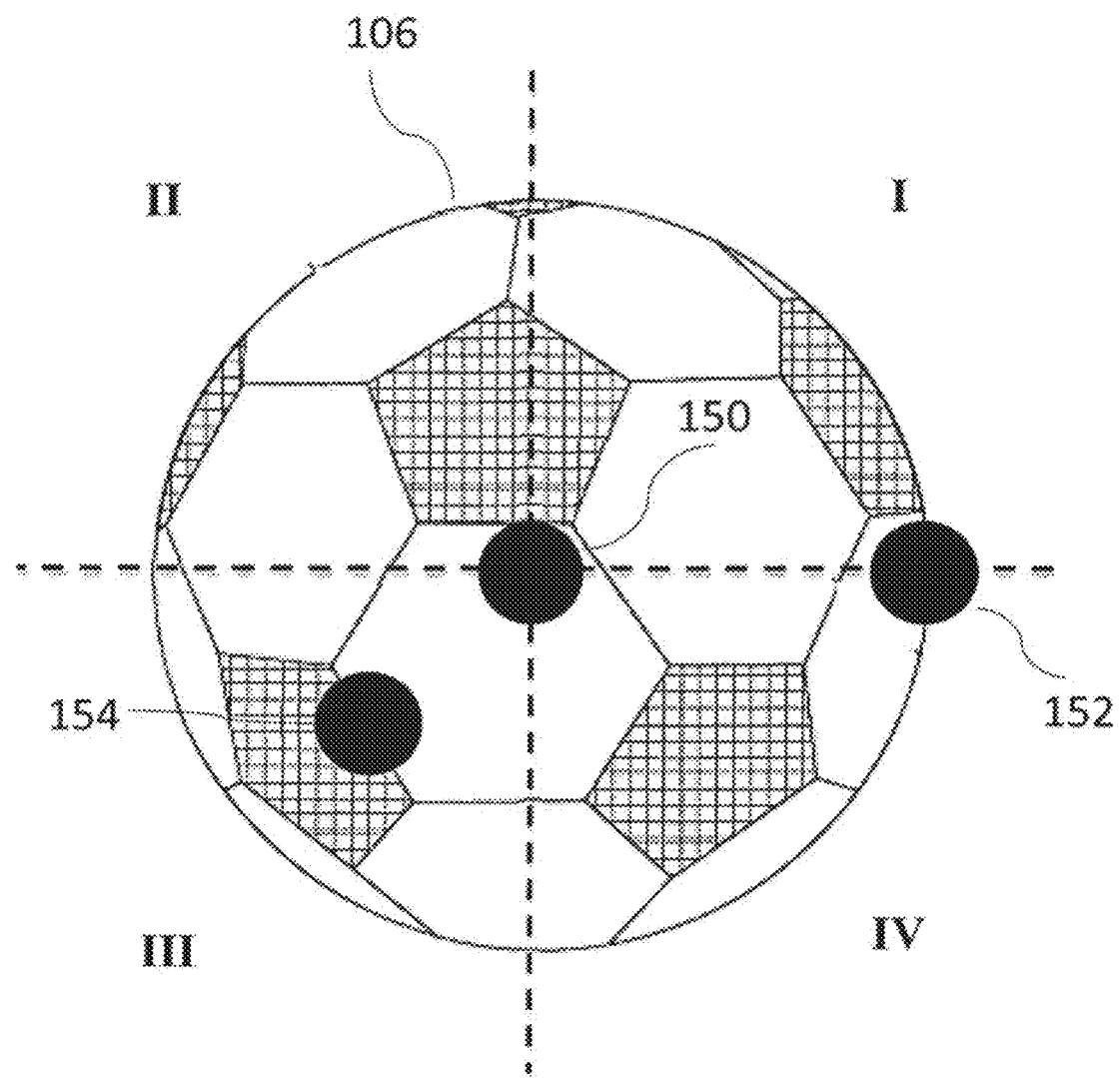
FIG. 17 is an illustration of a sport ball according to an embodiment of the present invention.

FIG. 17 provide a useful diagram for characterizing the locations of points of impact 150 on the surface of a soccer ball 106. In this exemplary figure, a soccer ball 106 viewed from the front has been divided into four quadrants: I, II, III, and IV. A first point of impact 150, a second point of impact 152, and a third point of impact 154 are also illustrated. The precise location of the point of impact 150, 152, or 154 between an individual's 10 foot 12 and a soccer ball 106 is correlated to motion characteristics of the ball 106 including ball speed, ball spin rate, ball spin axis, and ball launch angle.

For example, if the soccer ball 106 is kicked straight on such that the point of impact corresponds to point 150 in FIG. 17—i.e. aligned with the dead center of the soccer ball 106 where quadrants I, II, III, and IV meet—substantially all of the energy from the foot-ball impact will transmitted as a linear displacement. In other words, the soccer ball 106 will be launched at a relatively high speed with little or no spin, a relatively level spin axis, and a relatively flat launch angle.

Alternatively, if the if the soccer ball 106 is kicked far off to one of its sides relative the individual's 10 approach and the intended flight path such that the point of impact corresponds to point 152 in FIG. 17—e.g. aligned with the "equator" of soccer ball 106 but off to the side in the direction of quadrants I and IV—substantially all of the energy that is transmitted will impart spin on the soccer ball 106. In other words, the soccer ball 106 will be launched at a relatively low speed with relatively high spin, and still with a relatively level spin axis and a relatively flat launch angle.

Finally, if the if the soccer ball 106 is kicked somewhat off to one of its sides and somewhat below the level of the "equator" of the soccer ball 106 such that the point of impact corresponds to point 154 in FIG. 17—e.g. off center of the soccer ball 106 but located relatively centrally within quadrant III—the energy that is transmitted will impart both speed and spin on the soccer ball 106. In other words, the soccer ball 106 may be launched at a relatively moderate speed with relatively moderate spin, but this time with a tilted spin axis and a relatively higher launch angle.

Several different empirical methods can be used to identify strike zones 140 and points of impact 150 for soccer balls 106 kicked by individuals 10. In one embodiment, a quadrant grid similar to the one depicted in FIG. 17 could be drawn onto the surface of soccer balls 106 and oriented toward the intended flight path of the soccer ball 106, and a visual identifying substance such as a food-grade dye can be applied to individuals' 10 feet 12 (or footwear). After a suitable sample of kicks is obtained, the locations of strike zones 140 and points of impact 150 for soccer balls 106 kicked by individuals 10 can be identified based on the locations of dye markings on the soccer balls 106 with respect to the applied grids. In the case where the marked soccer balls 106 are outfitted with sensor modules 102 of the present invention, measurements can be taken during the kicks to identify motion characteristics of interest such as ball speed, ball spin rate, ball spin axis, and ball launch angle.

In another embodiment, a substance such as a rapidly evaporating alcohol can be applied to individuals' 10 feet 12 (or footwear), and monitored kicks can be recorded with an infrared camera. In this embodiment, the locations of strike zones 140 and points of impact 150 for the soccer balls 106 kicked by individuals 10 can be identified based on an analysis of the recorded images of the locations of evaporating alcohol on the soccer ball 106, as sensed by local changes in temperature caused by the evaporation.

It is possible to use soccer balls 106 having sensor modules 102 such as those described above to obtain ball speed, ball spin rate, ball spin axis, and ball launch angle data using such methods. Based on these experimental data obtained by these methods, given a suitably large and representative sample and suitably precise measurement techniques, and assuming the energy transfer between the foot 12 and the soccer ball 106 depends solely on the inertial and elastic properties of the soccer ball 106 (which are constant), it is also possible to undertake a multi-variable regression analysis to link ball speed, ball spin rate, ball spin axis, and ball launch angle data to points of impact 150 location data for a soccer ball 106. In other embodiments, other methods such as high speed video analysis can be used as well to obtain the ball movement characteristics, and this information can be used to define the variables for a multi-variable regression analysis.

Regression analysis is a statistical process for estimating the relationships among variables. Regression analysis can be used to fit a predictive model to an observed data set of values. After developing such a model, if additional values of one or more variables (e.g. ball speed, ball spin rate, ball spin axis, ball launch angle, or point of impact 150) can be determined, the fitted model can be used to make a prediction of the values of unknown variables. When building a suitable model, given variables that may be related, regression analysis can be applied to, for example, quantify the strength of the relationships between the various variables, to assess which variables may have no relationship at all, or to identify which subsets of the variables contain redundant information.

Figure 18:
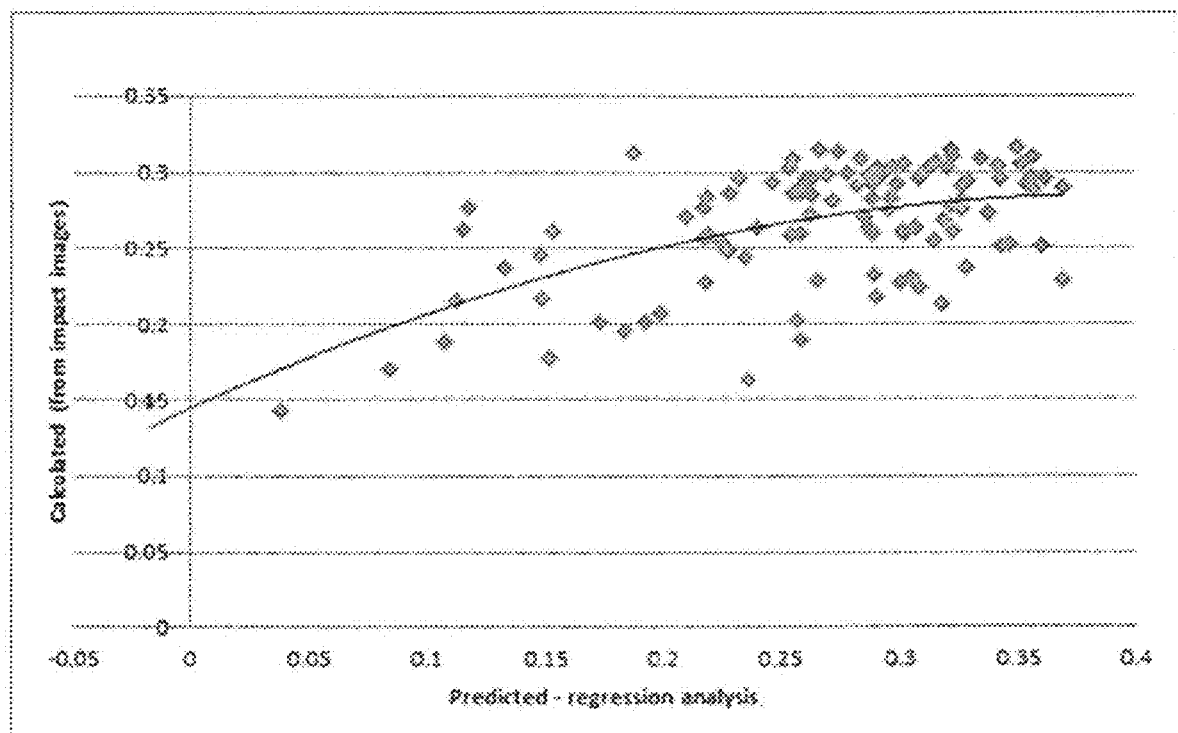
FIG. 18 is an illustration of a regression analysis plot according to an embodiment of the present invention.

In one embodiment of the present invention, a linear regression analysis can be employed to predict the relationship between ball speed, ball spin rate, ball spin axis, ball launch angle, or point of impact 150. In linear regression, data are modeled using linear predictor functions, and unknown model parameters are estimated from the data. Exemplary results of a linear regression analysis correlating points of impact obtained empirically to points of impact determine from applying a linear regression function to sensor module 102 data are illustrate in FIG. 18.

Figure 19:
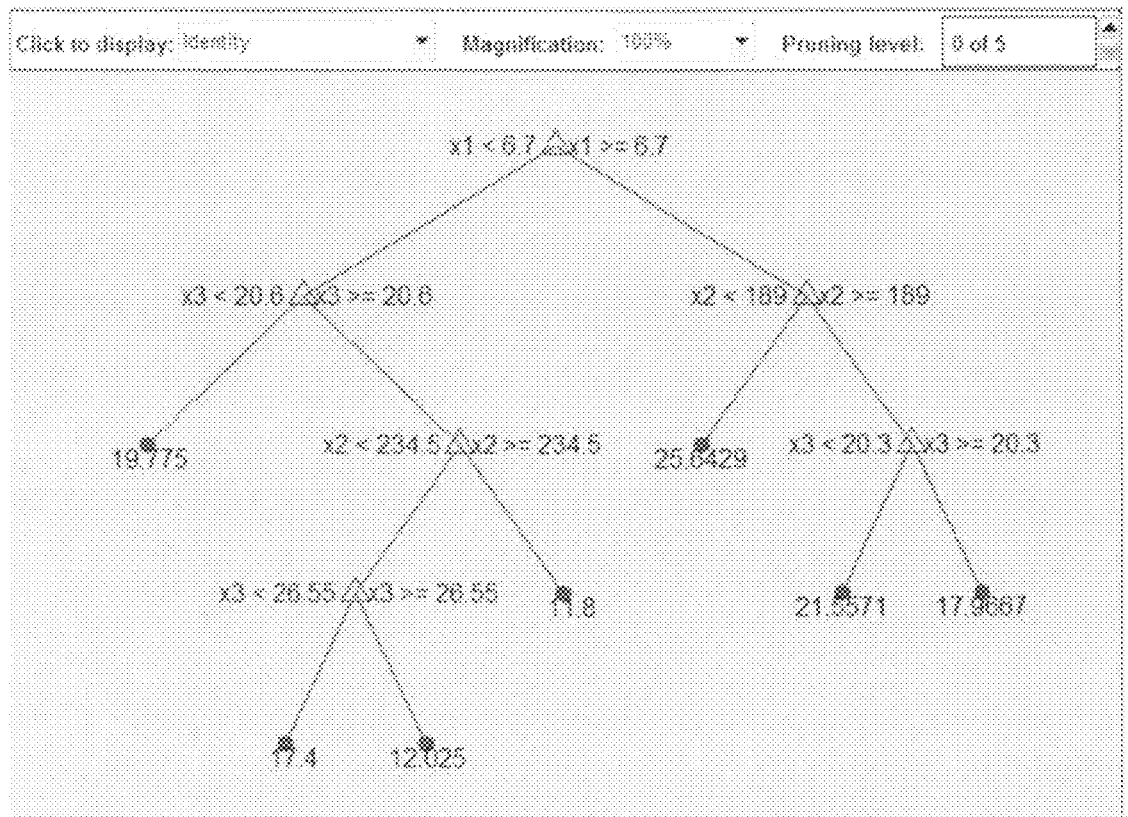
FIG. 19 is an illustration of a regression tree according to an embodiment of the present invention.

In another embodiment of the present invention, the regression analysis can alternatively rely on a tool known as a regression tree. A regression tree is a predictive model that maps observations about an item to conclusions about the item's target value. The goal is to create a model that predicts the value of a target variable based on several input variables. A tree can be derived by splitting the source set into subsets based on an attribute value test. This process is repeated on each derived subset in a recursive manner called recursive partitioning. The recursion is completed when the subset at a node has all the same value of the target variable, or when splitting no longer adds value to the predictions. A portion of an exemplary regression tree for correlating ball speed, ball spin rate, ball spin axis, ball launch angle, and point of impact 150 is shown in FIG. 19. In this figure, each x(n) variable represents one of the soccer ball 106 motion variables, while the leafs of the regression tree represent an outcome variable after applying the regression conditions for a given branch.

Once a regression analysis results in a model that establishes a relationship between ball speed, ball spin rate, ball spin axis, ball launch angle, and point of impact 150, measured or calculated values of some variables can be used to determine others that are unknown. In on embodiment of the present invention, data from a sensor module 102 of a soccer ball 106 may be used to determine ball speed, ball spin rate, ball spin axis, and ball launch angle, for a given kick, and this data may be used to determine a point of impact 150 for the kick.

In one embodiment of the present invention, a regression analysis can be used to determine a point of impact 150 for a kick based on acceleration data obtained for a sport ball 106, such as a soccer ball 106. The acceleration data may be obtained from a sensor module 102 of the sport ball 106, or from another source. In other embodiments, the regression analysis can be used to determine a point of impact 150 for a kick based on other data such as magnetometer data, angular momentum sensor data, or multiple types of data.

Figure 20:
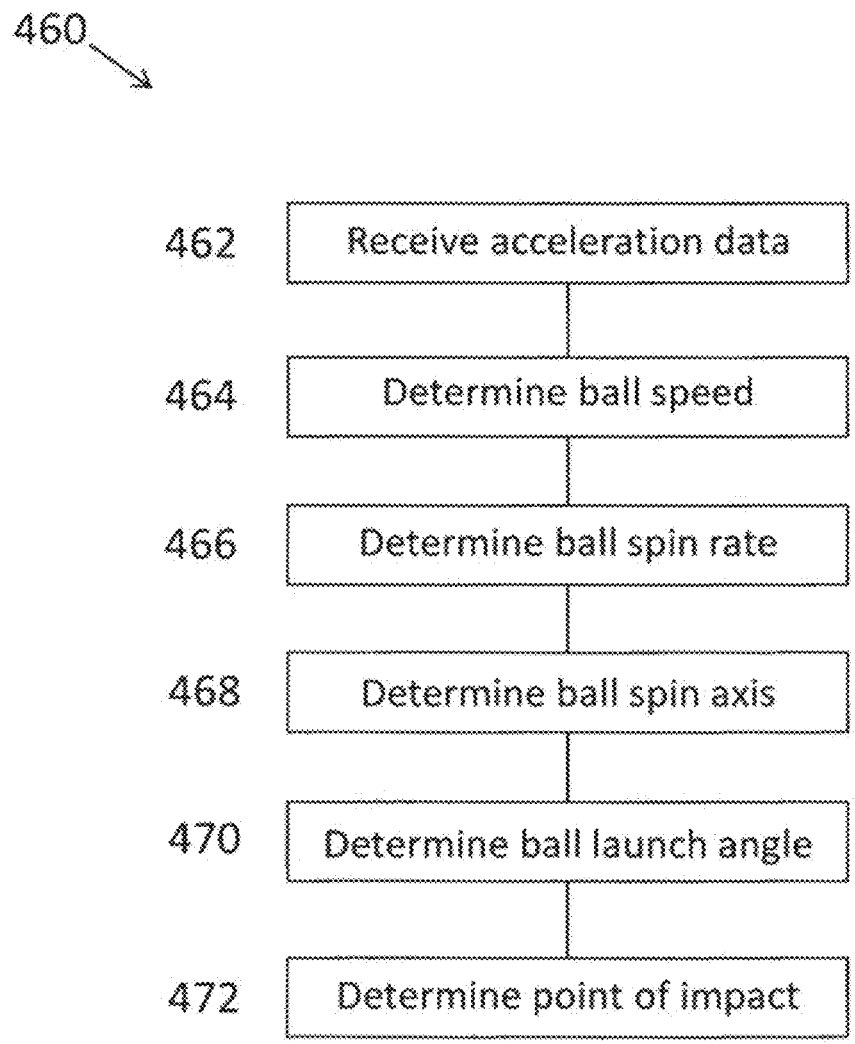
FIG. 20 is a flow chart illustrating a regression analysis according to an embodiment of the present invention.

In an exemplary embodiment, as illustrated in FIG. 20, a regression analysis process 460 begins at step 462 by receiving acceleration data. At step 464, the regression analysis determines soccer ball 106 speed. At step 466, the regression analysis determines soccer ball 106 spin rate. At step 468, the regression analysis determines soccer ball 106 spin axis. At step 470, the regression analysis determines soccer ball 106 launch angle. Each of these parameter determining steps may be conducted in accordance with the discussion provided above regarding obtaining these parameters. Finally, at step 472, the regression analysis determines the location of a point of impact 150 on the soccer ball 106.

As noted above, the regression analysis may rely on a regression tree. A regression tree may be used when linear regression techniques do not yield suitable predictive results. The regression tree is a model that can predict the value of a point of impact 150 based on ball speed, ball spin rate, ball spin axis, and ball launch angle derived, in one embodiment, from acceleration data. In some embodiments, the regression tree can provide local data correlations that are not valid globally. The key is fitting a given set of input data into a particular portion of the regression tree where a good fit among the data can be found. For example, one branch of the regression tree may be a good fit for a kick with a high spin, low speed kick, while another branch of the regression tree may be a good fit for a kick with a low spin and high speed. Additional variables can be added to the analysis in various branches of the tree. But at some point, adding new variables requires significantly more data analysis while giving little added accuracy. In other words, at some point continuing to split new branches of the tree no longer adds value to the predictions.

Figure 21:
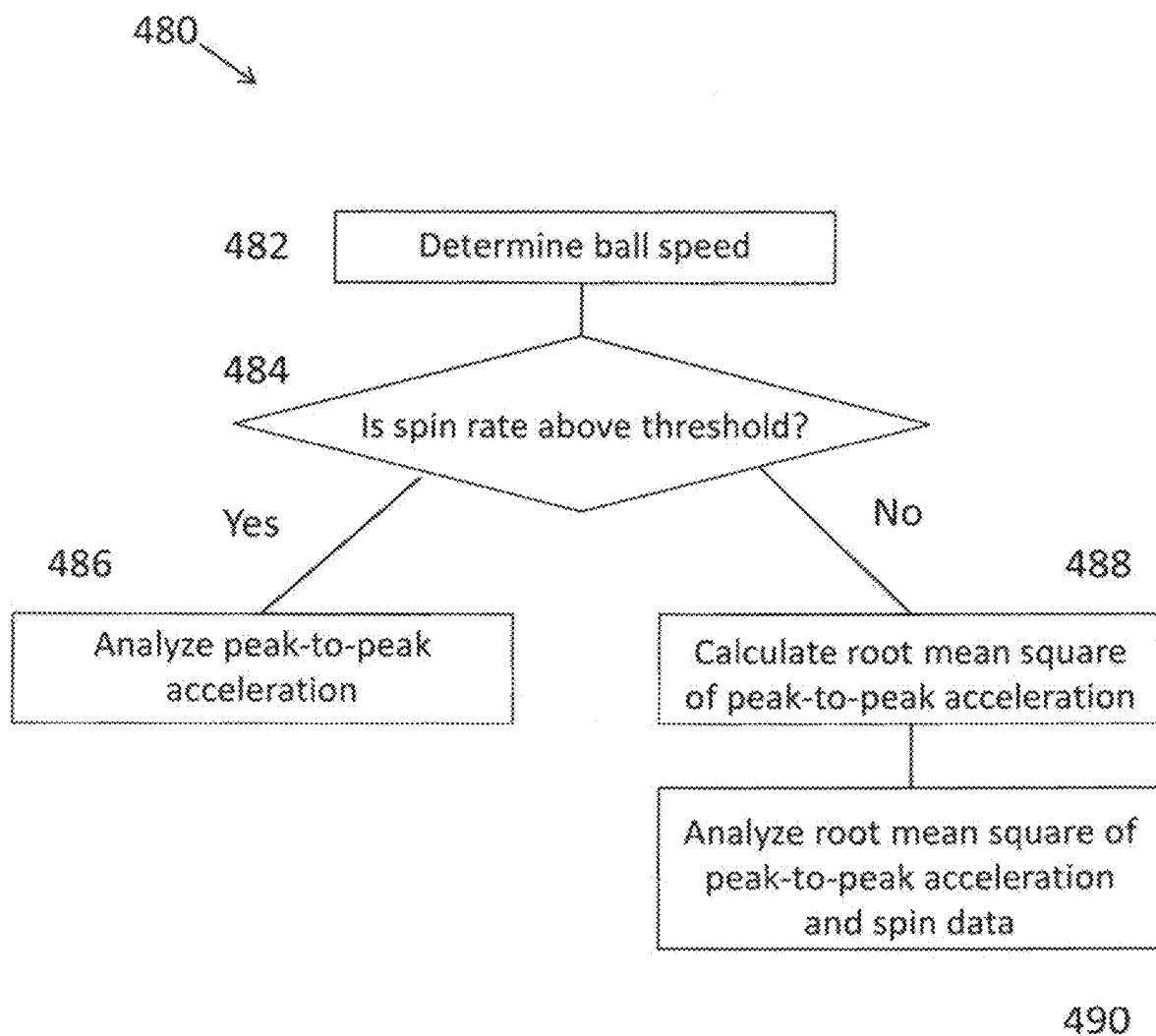
FIG. 21 is a flow chart illustrating a regression analysis according to an embodiment of the present invention.

In one exemplary embodiment of the present invention, as illustrated in FIG. 21, the best method for determining soccer ball 106 speed (as explained with reference to step 464 of FIG. 20), for a given kick may depend on whether an underlying variable is above a given threshold. For example, in an embodiment, a speed determination process 480 begins at step 482 (which may correspond to step 464 of FIG. 20) when speed is to be determined. At step 484, a determination is made as to whether the spin rate of the soccer ball 106 is above a certain threshold. In other embodiments, other variable thresholds may be employed. In one embodiment, a threshold of five revolutions per second may be used. Kicks where the soccer ball 106 is determined to be rotating less than five revolutions per second may be deemed "slow spin" kicks, while kicks where the soccer ball 106 is determined to be rotating more than five revolutions per second may be deemed "high spin" kicks.

In one embodiment, as illustrated in step 486 of FIG. 21, if the spin rate of the soccer ball 106 is above the five revolutions per second threshold, the regression analysis may proceed by analyzing the peak-to-peak acceleration output from an acceleration sensor, such as sensor module 102. The peak-to-peak acceleration may consist of difference between the highest and lowest acceleration readings of resultant acceleration values. In the case of a multi-axis accelerometer (e.g. a triaxial accelerometer), the resultant acceleration values could factor in readings from each axis of the accelerometer.

In another embodiment, however, as illustrated in step 488 of FIG. 21, if the spin rate of the soccer ball 106 is not above the five revolutions per second threshold, the regression analysis may proceed by calculating root mean squares of the peak-to-peak acceleration. A root mean square of a value is a scalar measure of the magnitude of a varying quantity of the value. Root mean squares of the peak-to-peak acceleration values may be calculated for low-spin kicks because acceleration output behaves linearly under such conditions. In addition, at step 490, the regression analysis analyzes both the root mean squares of the peak-to-peak acceleration values and spin data itself to determine soccer ball 106 speed. Factoring in spin data corrects for some of the uncertainty in the speed calculations introduced by virtue of having to apply root mean squares of the peak-to-peak acceleration values.

Regardless of whether the kick was over or under the five revolutions per second spin threshold, the outcome of speed process 480 can be fed into a general regression analysis as specified in regression process 460 of FIG. 20 in order to determine a point of impact 150 for a kick.

In one embodiment of the present invention, the soccer ball 106 must be in a free flight state after being kicked in order for the sensor module 102 to provide accurate data for soccer ball 106 motion characteristic determinations. In other embodiments, the motion monitoring system 100 is able to make accurate data for soccer ball 106 motion characteristic determinations even when the soccer ball 106 in not in a free flight state after being kicked.

One non-free flight state after a soccer ball 106 is kicked is known as a "grounder," which occurs when the soccer ball 106 is kicked and rolls or repeatedly bounces across the ground. Another non-free flight state after a soccer ball 106 is kicked is known as a "toe scoop," which occurs when the soccer ball 106 is not truly kicked but actually scooped relatively slowly by the foot 12 and then released; the soccer ball 106 is not truly impacted, just scooped—in a non-free fall state—and tossed.

In one embodiment, when the motion monitoring system 100 determines that a grounder or toe-scoop has occurred, the individual 10 will be given a general error message. In another embodiment, the motion monitoring system 100 will specifically inform that the individual 10 that a grounder or a toe-scoop has been kicked. A more specific error message may prevent the individual 10 from losing confidence in the system 100 if the individual 10 assumed that any general error resulted from malfunction of the device, and not the individual's 10 improper grounder kick.

IV. Exemplary Portable Electronic Device Software Application Embodiments

As previously noted with respect to FIG. 8, in some embodiments of the present invention, a sport ball 106 having a sensor module 102 may communicate with a portable electronic device 306 of the motion monitoring system 100, such as a smart phone, that is also carried by the individual 10 during the athletic activity. As illustrated by FIGS. 22-49, various software modules of a sport ball 106 motion monitoring portable electronic device 306 software of the present invention may support graphical user interfaces (GUIs) through which an individual 10 can interact with the sport ball 106 motion monitoring system.

In an embodiment of the present invention, the portable electronic device 306 may take the form of a mobile phone and may include at least a processor, a memory, user input controls, a positioning system receiver, a wireless wide area network (WWAN) transceiver, a visual display, and an audio unit. A visual display in the form of a LCD screen, and user input controls in the form of a physical keyboard and a scroll ball may be present.

The memory of the portable electronic device 306 may be adapted to store application programs used to implement aspects of the functionality of the motion monitoring system 100 described herein, such as a sport ball 106 motion monitoring system 100 portable electronic device 306 software application. Thus, the application software may be stored, for example, in the memory of the portable electronic device 306. Alternatively, those of skill in the art will understand that all or part of the software may be stored on the server 302 and accessed over the network 300 and run remotely as a mobile web application.

This sport ball 106 motion monitoring system 100 portable electronic device 306 software application includes a number of different software modules capable of providing sport ball 106 motion monitoring services to individuals 10 using sport balls 106 or other pieces of athletic equipment equipped with sensor modules 102. In one embodiment of the present invention, these modules include a kick it module, a get better module, a challenges module, and a record book module. Each module may support one or more GUIs capable of being presented to an individual 10 using the sport ball 106 motion monitoring system 100.

A GUI may offer, for example, graphical elements, visual indicators, and/or text to represent information and actions available to the individual 10. The individual 10 may use a physical input device, such as keyboard or scroll ball to interact with the GUI of the portable electronic device 306. Alternatively, the individual 10 may use a touch screen to interact directly with what is displayed. Various touch screens such as, for example, resistive or capacitive touch screens, may be employed.

Those skilled in the art will appreciate that alternative or additional software modules and sub-modules may be implemented in order to provide or extend the described or additional functionalities to the individual 10 using the portable electronic device 306. For example, the software configuration of software stored on a portable electronic device 306 may include a portable device operating system, which may be one of the commercially available mobile phone operating systems such as, for example, BlackBerry OS, iPhone OS, Windows Mobile, Symbian, LINUX, WebOS, or Android. The portable device operating system may also have an associated application programming interface through which middleware and application programs may access the services of the operating system.

The various modules of the sport ball 106 motion monitoring system 100 of the present invention may support GUIs through which an individual 10 can interact with the sport ball 106 motion monitoring system 100 using the portable electronic device 306 just prior to and/or during an activity. As will be appreciated by those of skill in the art, in one embodiment the GUIs may be supported by a mobile device application being run on the portable electronic device 306. In another embodiment, the GUIs may appear as web pages provided by the server 302 via a website that may be accessible to the individual 10 over the network 300 using a web browser on their portable electronic device 306.

In order to access the features of embodiments of the present invention just prior to or during a physical activity, the individual 10 using the portable electronic device 306 may power on their portable electronic device 306 if it is not already in a powered up state. In some embodiments, it may be necessary for the individual 10 to manipulate user input controls to enter sport ball 106 motion monitoring system 100 mode to access the application software.

The first time the sport ball 106 motion monitoring system 100 application is launched, a start module may prompt the individual 10 to, for example, select a preferred language, enter a password to proceed, link their portable electronic device 306 to a web account previously set up via the server 302. The individual 10 may also be prompted to enter information such as, for example, preferred unit preferences, personal information such as the individual's 10 age, height, weight, and sex, and/or the individual's 10 desired voice training options.

Figure 22:
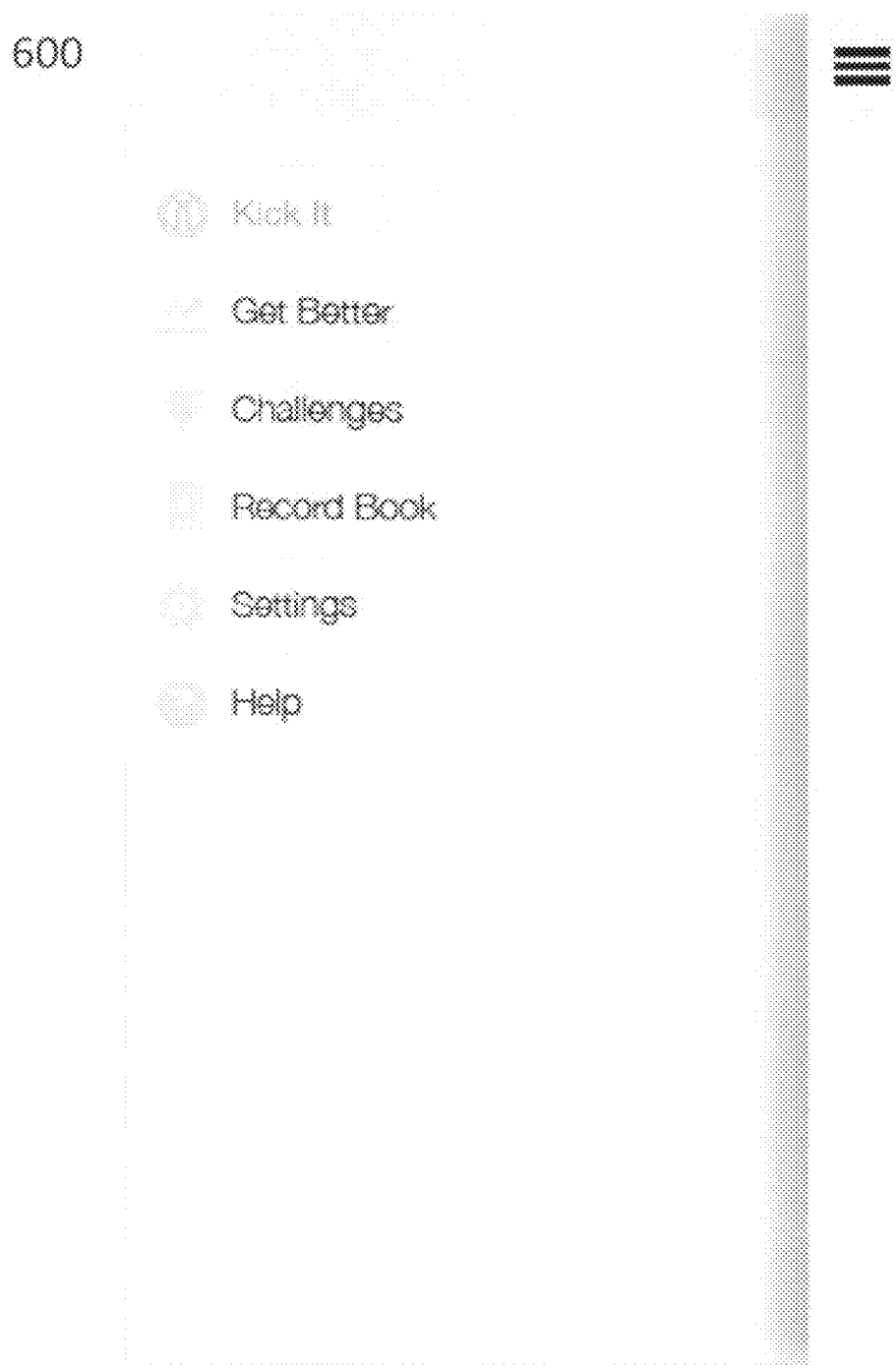
FIG. 22 is a graphical user interface for a sport ball motion monitoring application according to an embodiment of the present invention.

The start module may present a menu 600 GUI, as illustrated in FIG. 22. During subsequent launches of the software application, the menu 600 may be presented to the individual 10 immediately upon launch. The menu 600 may include several icons or indicia corresponding to the kick it, get better, challenges, and record book modules, as well as icons or indicia corresponding to settings or help features, as illustrated in FIG. 22. After launching the application software, the individual 10 may cause different GUI pages to be provided by different modules by selecting their corresponding icons using user input controls. Additional icons corresponding to sub-modules or program wizards associated with a particular module may pop up or otherwise be displayed to the individual 10 if the individual 10 selects, swipes, or hovers over a module icon with a cursor.

Figure 23:
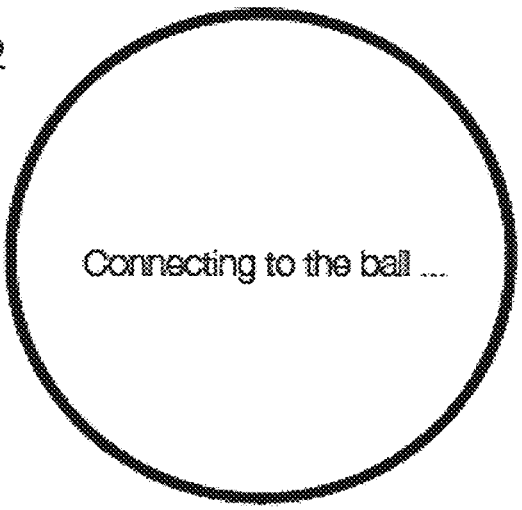
FIG. 23 is a graphical user interface for a sport ball motion monitoring application according to an embodiment of the present invention.

FIG. 23 is an exemplary GUI window that may be provided by the kick it module. This GUI window may display a ball icon 602 that may be used to convey various pieces of information to the individual 10. In addition, the GUI window may display a selection icon 604 for indicating which foot 12 (left or right) the individual 10 is going to be kicking a sport ball 106 with. Before the individual 10 can begin to use the motion monitoring system 100, they must successfully pair the portable electronic device 306 to a sport ball 106, such as a soccer ball 106 having a sensor module 102. Pairing is a process used in computer networking that helps set up an initial linkage between computing devices to allow communications between them. Pairing may occur wirelessly via a personal area network or local area network using, for example, the Bluetooth wireless protocols. The kick it module may prompt the individual 10 to pair their portable electronic device 306 to a soccer ball 106, and may display updates to the individual 10 as to the status of the pairing. Updates may include notifying the individual 10 that the portable electronic device 306 is attempting to connect to the soccer ball 106, that a connection has been made, or that a connection cannot be made. In one embodiment, these prompts or notifications may appear in the ball icon 602.

Once the portable electronic device 306 and the soccer ball 106 have been successfully paired, the individual 10 is ready to monitor a kick using the motion monitoring system 100. Prior to attempting a kick, however, the individual 10 may be presented with one or more tips in using the motion monitoring system 100. In some embodiments the individual 10 is provided with the tips automatically, while in other embodiments the individual 10 must request the tips my indicating a user input. Tips may include, for example, instructions on how to position and orient the soccer ball 106 on the ground such that certain indicia on the surface of the soccer ball 106 are aligned with external elements such as the ground, the individual's 10 desired approach to the soccer ball 106, and/or the individual's 10 intended target or goal. In some embodiments, properly placing and orienting the soccer ball 106 will ensure that the sensor module 102 of the soccer ball 106 is properly aligned and calibrated so that data readings from the soccer ball 106 will be accurate.

Other tips may include instructions on how the soccer ball 106 must be kicked so as to obtain meaningful and accurate monitoring results. For example, in one embodiment, instructions may include kick distance and height limitations, such as that the ball 106 must be kicked at least ten yards and at least two feet off of the ground to successfully track the kick. Still other tips may include turning up the volume on the individual's 10 portable electronic device 306 for an optimal experience.

Figure 24:
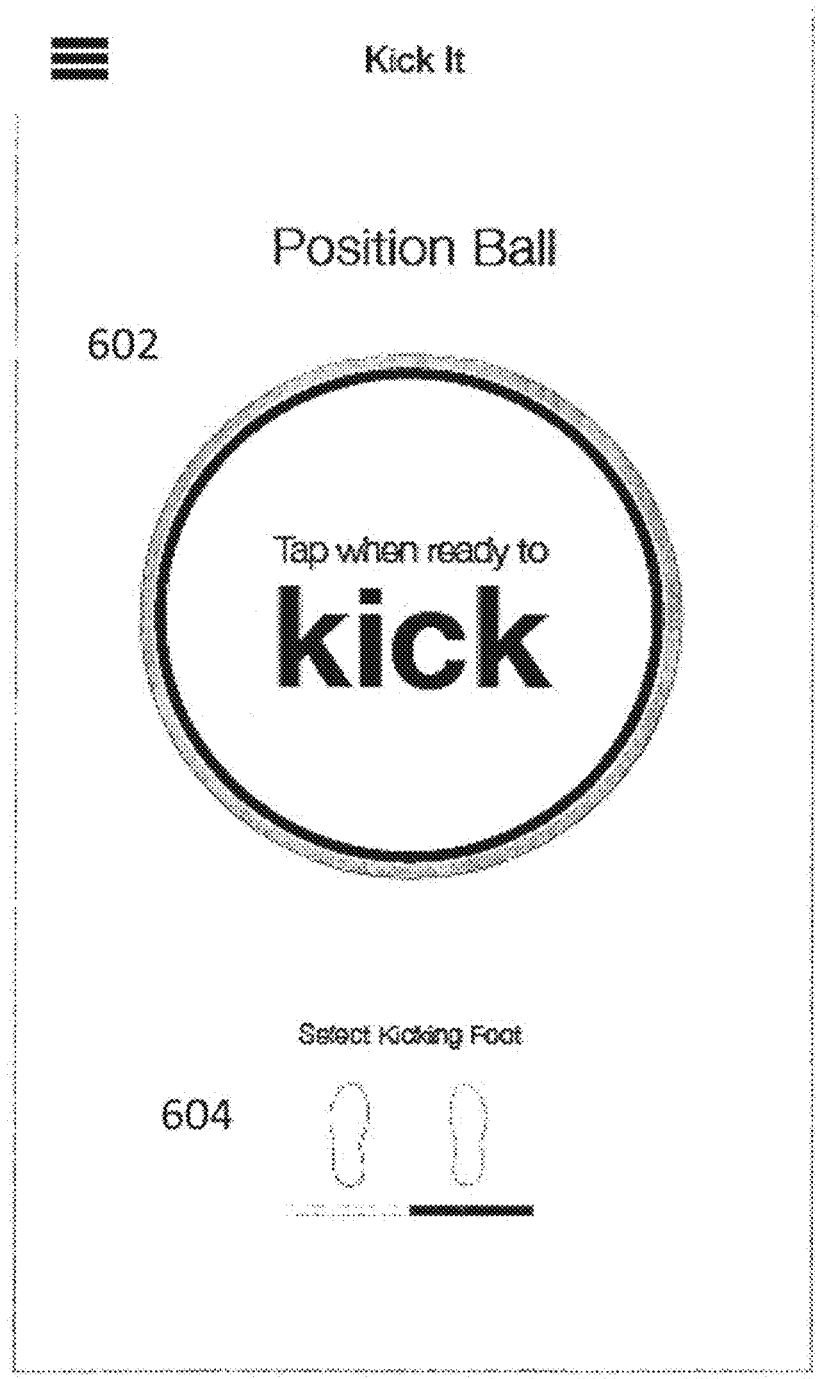
FIG. 24 is a graphical user interface for a sport ball motion monitoring application according to an embodiment of the present invention.

After any tips have been presented, or in the absence of tips, the individual 10 may be presented with a prompt to tap the ball icon 602 when they are ready to monitor a kick using the motion monitoring system 100. For example, FIG. 24 is an exemplary GUI window that may be provided by the kick it module instructing the individual 10 to tap the ball icon 602 when they are ready to monitor a kick. If not previously selected, the individual 10 may activate a selection icon 604 for indicating which foot 12 (left or right) the individual 10 is going to be kicking a soccer ball 106 with.

In response to receiving an indication that the individual 10 is ready to monitor a kick (e.g. the individual 10 taps the ball icon 602), the portable electronic device 306 may communicate with the soccer ball 106 having a sensor module 102 to notify the soccer ball 106 to expect a kick. In one embodiment, the soccer ball 106 may prepare for an upcoming kick by adjusting its power consumption, adapting its processing, begin data recording, calibrate its sensors, or other operation. In another embodiment, the soccer ball 106 may send a return signal to the portable electronic device 306 to indicate that the soccer ball 106 is ready to be kicked.

At this stage, the individual 10 may kick the soccer ball 106. As previously noted with respect to FIG. 17, a soccer kick can involve a series of complex motions by an individual 10 leading up to the striking of the soccer ball 106 by the individual's 10 foot 12. Depending on the intended flight path and other motion characteristics of the soccer ball 106, the individual 10 may need to utilize a particular approach and ball-striking mechanics.

When the soccer ball 106 is kicked, the sensor module 102 is capable of recording movement date associated with the kick, as described above with respect to FIGS. 8-21. The soccer ball 106 having the sensor module 102, alone or in combination with the portable electronic processing device 306, may be capable of determining motion characteristics of the soccer ball 106 including ball speed, ball spin rate, ball spin axis, and ball launch angle.

In an embodiment of the present invention, is response to receiving the indication from the portable electronic device 306 that the individual 10 is ready to monitor a kick, the paired sport ball 106 may begin sampling data from the sensor module 102 at a predetermined rate. For example, in embodiments where the sensor module 102 includes one or more acceleration sensors 118, the sport ball 106 may sample data from the acceleration sensors 118 at a rate of 1 kHz. In one embodiment, the sport ball 106 may continue sampling data from the acceleration sensors 118 at a rate of 1 kHz and saving the acceleration data into a file 700 on a memory device of the sport ball 106 indefinitely, until a predetermined amount of required memory is reached, or until all of the kick monitoring session is complete.

In another embodiment, as illustrated in FIGS. 50A-50C, the sport ball 106 may employ a data sampling system that relies on both a file 700 on a memory device and a separate buffer data structure, such as a circular buffer 702 of fixed size that is significantly smaller than the size of the file 700 on the memory device. In this embodiment, in response to receiving the indication from the portable electronic device 306 that the individual 10 is ready to monitor a kick, the sport ball 106 may sample data from the acceleration sensors 118 at a rate such as 1 kHz and continually save the acceleration data into the circular buffer 702, overwriting previous data as necessary, as shown in FIG. 50A.

In an embodiment, the sport ball 106 may employ a compression algorithm to optimize memory utilization and post kick data analysis. The sport ball periodically analyzes the sampled data in the circular buffer 702 to determine when to alter the rate at which samples are saved into memory based on the variability of the data. If the sport ball 106 determines that the data has a low variability, the sport ball 106 may periodically save low variability values into the file 700 on the memory device of the sport ball 106 at a rate as infrequent as 1 Hz, as shown in FIGS. 50A and 50B. This practice may allow the file 700 on the memory device to take up less memory space than if the sampled data were saved directly to the file 700 on the memory device of the sport ball 106 at a much higher rate such as 1 kHz. In FIGS. 50A-50C, saved data 704 from the accelerometer is identified by reference numeral 704, while low variability values 706 (e.g. a 1 G acceleration due solely to gravity) are identified by reference numeral 706. In one embodiment, the compression algorithm can adjust the data save rate dynamically in a way that correlates with the signal variability.

On the other hand, if the sport ball 106 determines that the acceleration data has become highly variable, the sport ball 106 may begin saving the sampled data directly into the file 700 on the memory device of the sport ball 106 instead of to the circular buffer 702, as shown in FIG. 50B. In addition, at the point in time when the sport ball 106 begins saving the sampled data directly into the file 700, the sport ball 106 may also insert some or all of the data existing at that point in time in the circular buffer 702 into the file 700 just ahead of the new sampled data, as shown in FIG. 50C. In this way, the file 700 on the memory device is able to capture acceleration data at each point in time and only in the highest fidelity necessary at each moment in time for later post kick analysis.

While the above described data processing is occurring at the sport ball 106, in an embodiment of the present invention, after transmitting an indication to the sport ball 106 that the individual 10 is ready to monitor a kick, the portable electronic device 306 may communicate with the sport ball 106 to download saved data from the file 700 on the memory device of the sport ball 106. In another embodiment, the portable electronic device 306 may first seek to determine how much data is presently stored in the file 700 on the memory device of the sport ball 106. In some embodiments, this sort of communication may occur periodically, such as once every 100 or 200 milliseconds. In one embodiment, the communication to determine how much data is presently stored in the file 700 on the memory device may occur every 100 or 200 milliseconds until the portable electronic device 306 receives data indicating that the memory device has reached a certain level of capacity, such as being 2% full, 25% full, 50% full, or 100% full. When the portable electronic device 306 receives data indicating that the memory device has reached a certain level of capacity, such as being totally full, the portable electronic device 306 may begin to download saved data from the file 700 on the memory device of the sport ball 106. In this way, communications between the portable electronic device 306 and the sport ball 106 can be reduced to only the most essential communications, and data storage on the memory of the sport ball 106 can be managed. In another embodiment, the sport ball 106 may broadcast the status of its memory capacity without prompting for such information by the portable electronic device 306. In an alternate embodiment, the portable electronic device 306 may constantly download saved data from the file 700 on the memory device of the sport ball 106.

Figure 25:
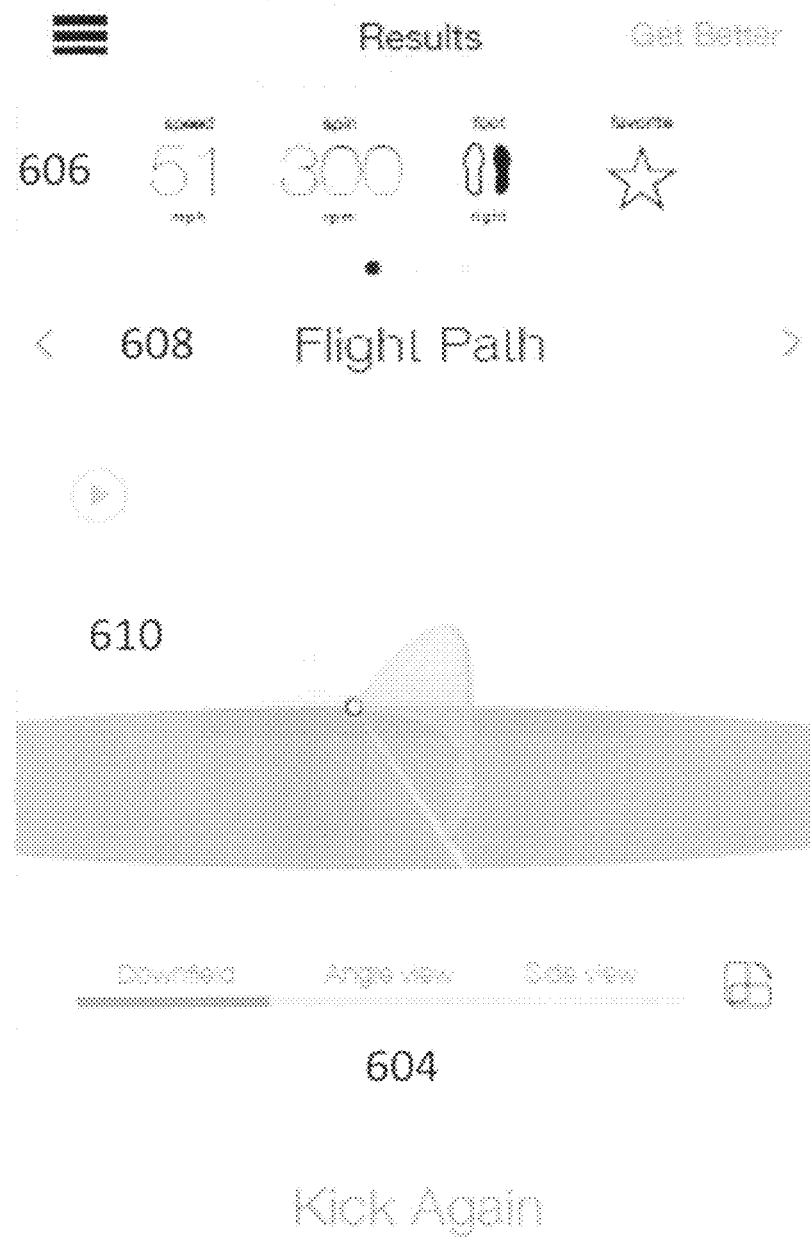
FIG. 25 is a graphical user interface for a sport ball motion monitoring application according to an embodiment of the present invention.

FIG. 25 is an exemplary GUI window that may be provided by the kick it module that provides a visual display to the individual 10 giving them feedback about the motion characteristics of the soccer ball 106 during their kick. The exemplary GUI includes a statistical display bar 606 that may provide, for example, information on the maximum speed of the soccer ball 106 during the post-kick flight or information on the maximum spin rate of the soccer ball 106 during the post-kick flight. In some embodiments, the statistical display bar 606 may also provide an indication of which foot 12 the individual 10 kicked the soccer ball 106 with, as well as an indication of whether the individual 10 has designated the kick as a "favorite" kick.

The exemplary GUI of FIG. 25 also includes a video element 610. The exemplary video element 610 shown is an animation that represents the flight path of the kicked soccer ball 106 in three dimension, set upon the background of a representation of a soccer goal. In some embodiments the animation may start automatically, while in other embodiments the individual 10 must provide an input to the portable electronic device 306 to request that the video play. In one embodiment, the perspective of the animated flight path may change such that the individual's 10 perspective may appear to rotate around the animated flight path to provide a better perspective on the flight path. In another embodiment the individual 10 may be presented with a selection icon 604 allowing the individual 10 to choose different animated views of the kick and fight path such as, for example, a downfield view, an angled view, or a side view. The particular flight path shown and animated may be based partially or entirely on the determined motion characteristics of the soccer ball 106, such that the flight animated flight path is a realistic approximation of the actual flight path of the kicked soccer ball 106.

Other visual displays giving feedback about the motion characteristics of the soccer ball 106 during their kick may also be provided to the individual 10. In one embodiment, as shown in FIG. 25, a swipe element 608 may indicate to the individual 10 that swiping their finger across the display screen may lead to other pages that display additional feedback. In other embodiments, buttons, switches, links, or other elements may be substituted for a swipe element 608.

Figure 26:
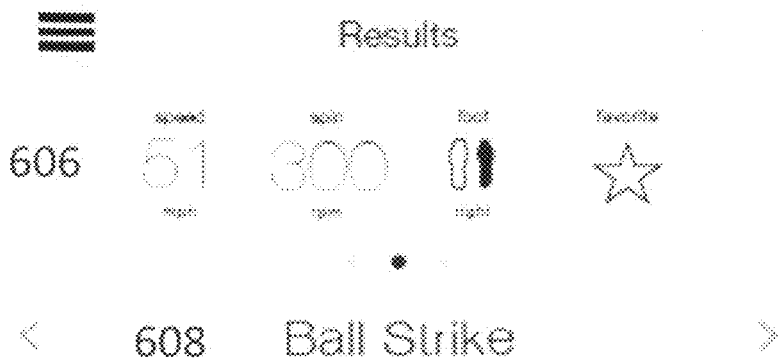
FIG. 26 is a graphical user interface for a sport ball motion monitoring application according to an embodiment of the present invention.
Figure 26:
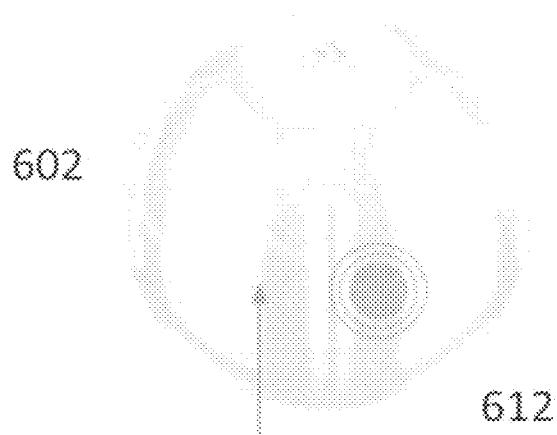

FIG. 26 is an exemplary GUI window that may be provided by the kick it module that provides one such other visual display—a ball strike display. For example, the exemplary GUI window of FIG. 26 could be displayed to the individual 10 after the individual 10 swiped the display of the exemplary GUI window of FIG. 25 to transition from the display of flight path feedback to the display of FIG. 26.

FIG. 26 provides information on point of impact 150 data. Such data may be obtained, for example, according to a regression process 460 analysis as described above with respect to FIGS. 16-21. As noted above, a relationship exists between the location of the point of impact 150 between an individual's 10 foot 12 and a soccer ball 106 and motion characteristics of the soccer ball 106 during and after it is kicked. The exemplary GUI display FIG. 26 illustrates a point of impact icon 612 overlaid on top of a ball icon 602, where the point of impact icon 612 is representative of the calculated point of impact 150 derived from the regression process 460 analysis as described above with respect to FIGS. 16-21. In other words, the point of impact icon 612 displayed via portable electronic device 306 corresponds to the calculated point of impact 150 that represents the location on the surface of the soccer ball 106 that approximately coincides with the center of the area of the foot 12 in contact with the soccer ball 106.

Accordingly, the methods previously described for analyzing the relationship between the location of the point of impact 150 between an individual's 10 foot 12 and a soccer ball 106 and motion characteristics of the soccer ball 106 during and after it is kicked can be used to generate feedback to the individual 10 via the portable electronic device 306, such as visually illustrating the location of a point of impact icon 612 overlaid on top of a ball icon 602, as shown in FIG. 26. The point of impact icon 612 shown in FIG. 26 includes a circular dot with a series of animated rings that may visually "pulse" to help draw attention to the location of the point of impact icon 612. This particular point of impact icon 612 appears below and to the right of the center of the soccer ball 106, as viewed from a front perspective.

The exemplary GUI window of FIG. 26 also includes the same statistical display bar 606 shown in FIG. 25 that provides information on the maximum speed of the soccer ball 106 during the post-kick flight, information on the maximum spin rate of the soccer ball 106 during the post-kick flight, an indication of which foot 12 the individual 10 kicked the soccer ball 106 with, as well as an indication of whether the individual 10 has designated the kick as a "favorite" kick. The exemplary GUI window of FIG. 26 additionally includes the same swipe element 608 shown in FIG. 25 that may indicate to the individual 10 that swiping their finger across the display screen may lead to other pages that display additional feedback. Again, other embodiments, buttons, switches, links, or other elements may be substituted for a swipe element 608.

Figure 27:
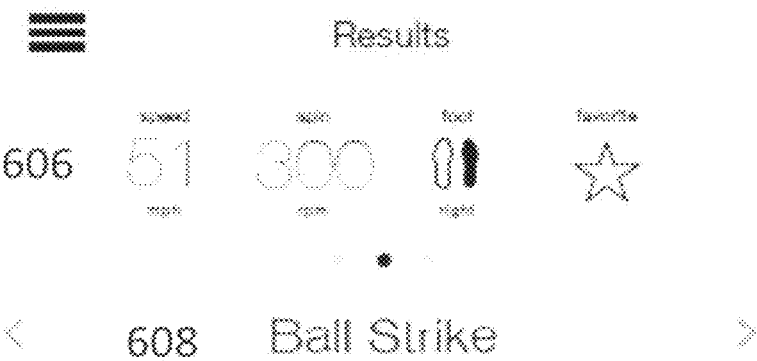
FIG. 27 is a graphical user interface for a sport ball motion monitoring application according to an embodiment of the present invention.

In one embodiment of the present invention, the motion monitoring system 100 application running on the portable electronic device 306 may log and display multiple point of impact icons 612 corresponding to multiple points of impact 150 between an individual's 10 foot 12 and a soccer ball 106 during multiple kicks. Such a display is illustrated in FIG. 27. The displayed kicks may be consecutive kicks from a single session, or may be from other periods of time. In an embodiment, the ball strike display may be limited to generating a display corresponding to a certain number of most recent points of impact 150, such as the last five points of impact 150, or the last ten points of impact 150. In one embodiment, multiple point of impact icons 612 corresponding to each point of impact 150 are displayed as a heatmap overlay over a single ball icon 602. Point of impact icons 612 associated with earlier kicks may be displayed as somewhat transparent, becoming progressively more transparent over time until they are removed. In addition, or alternatively, point of impact icons 612 associated with more recent kicks may be larger, getting progressively smaller over time until they are removed. In some embodiments, the ball icon 102 is lightened in the ball strike view of FIG. 26 so as to reduce contrast so that the point of impact icon 612 heatmap is easier to see.

At any time when viewing their results, the individual 10 may be presented with a prompt to tap the ball icon 602—or to tap a separate icon such as an icon including an message to "kick again" as shown in FIG. 27—in order to repeat the soccer ball 106 kicking and tracking sequence. In this way, a series of kicks may be tracked and feedback may be provided as described above.

Other visual displays giving feedback about the motion characteristics of the soccer ball 106 during their kick may also be provided to the individual 10. In one embodiment, as shown in FIG. 27, a swipe element 608 may indicate to the individual 10 that swiping their finger across the display screen may lead to other pages that display additional feedback. Again, in other embodiments, buttons, switches, links, or other elements may be substituted for a swipe element 608.

Figure 28:
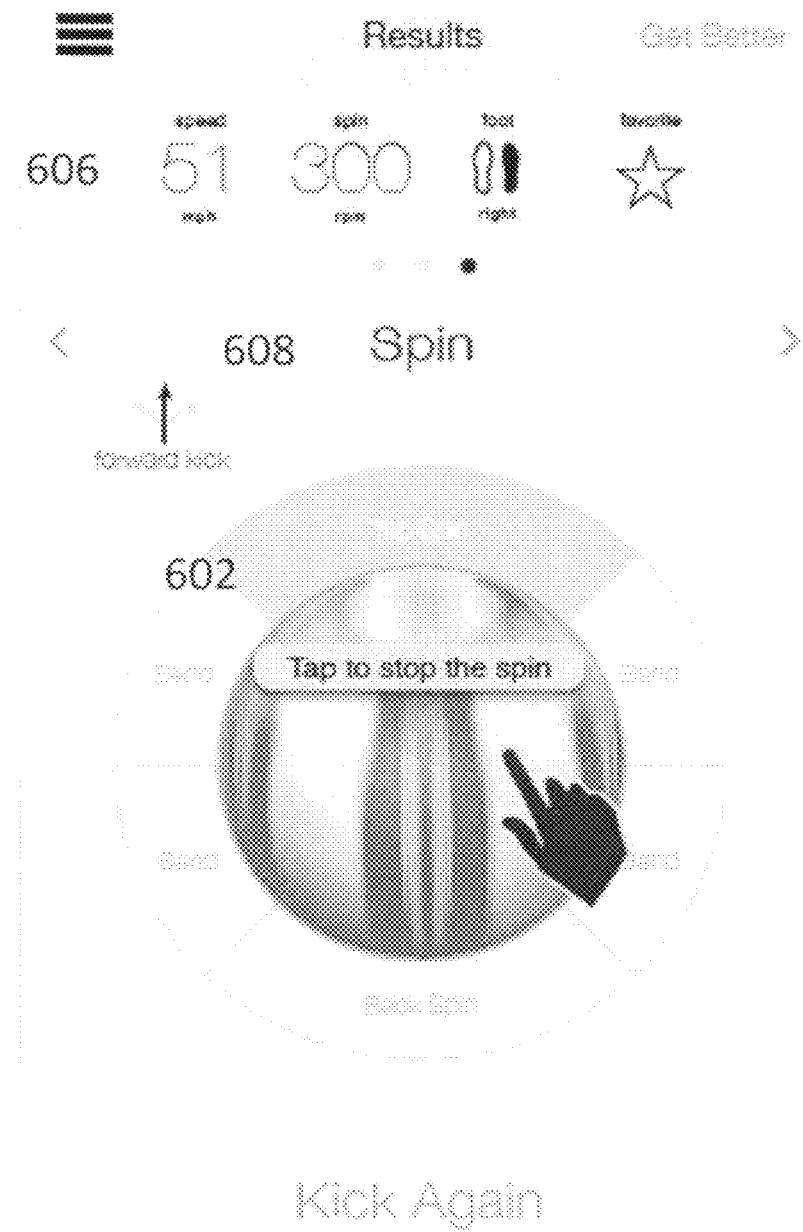
FIG. 28 is a graphical user interface for a sport ball motion monitoring application according to an embodiment of the present invention.

FIG. 28 is an exemplary GUI window that may be provided by the kick it module that provides one such other visual display—a spin display. For example, the exemplary GUI window of FIG. 28 could be displayed to the individual 10 after the individual 10 swiped the display of the exemplary GUI window of FIG. 25, 26, or 27 to transition from the display of flight path or ball strike feedback to the spin display of FIG. 28.

FIG. 28 provides information on ball spin data. Such data may be obtained, for example, according to analysis as described above with respect to FIGS. 9-14 using a sport ball 106 having a sensor module 102. The exemplary GUI window of FIG. 28 also includes the same statistical display bar 606 shown in FIG. 25 and other figures that provides information on the maximum speed of the soccer ball 106 during the post-kick flight, information on the maximum spin rate of the soccer ball 106 during the post-kick flight, an indication of which foot 12 the individual 10 kicked the soccer ball 106 with, as well as an indication of whether the individual 10 has designated the kick as a "favorite" kick. The exemplary GUI window of FIG. 26 additionally includes the same swipe element 608 shown in FIG. 25 and other figures that may indicate to the individual 10 that swiping their finger across the display screen may lead to other pages that display additional feedback. Again, other embodiments, buttons, switches, links, or other elements may be substituted for a swipe element 608.

The exemplary GUI window of FIG. 28 features a ball icon 602. In one embodiment, this ball icon 602 may be animated or otherwise depicted to represent the actual spin rate and spin axis of the soccer ball 106 during flight. For example, the ball icon 602 illustrated in FIG. 28 appears to be spinning rapidly with topspin. In embodiments of the present invention, the ball icon 602 may depict ball spin by way of animation, by way of a stationary image with indicia (e.g. arrows) to indicate a direction of spin, or by simply providing a numerical spin rate value, such as three hundred revolutions per minute. In some embodiments, as depicted in FIG. 28, the ball icon 602 may include a ringed border demarcating various zones such as topspin, backspin, or various "bend" zones. The bend zones may correspond to kicks that have sidespin alone or some degree of sidespin coupled with topspin or backspin.

In one embodiment of the preset invention, the visually depicted spin rate of an animated spinning ball icon 602 may be equal to the calculated spin rate of the soccer ball 106 as determined by the sensor module 102. For example, if the calculated spin rate of the soccer ball 106 is three hundred revolutions per minute, the visually depicted spin rate of an animated spinning ball icon 602 may three hundred revolutions per minute. In another embodiment of the present invention, the visually depicted spin rate of an animated spinning ball icon 602 may be proportional to, but not equal to, the calculated spin rate of the soccer ball 106 as determined by the sensor module 102. For example, if the calculated spin rate of the soccer ball 106 is three hundred revolutions per minute, the visually depicted spin rate of an animated spinning ball icon 602 may half of that spin rate—or one hundred and fifty revolutions per minute. In still other embodiments, the visually depicted spin rate of an animated spinning ball icon 602 may not be correlated to the calculated spin rate of the soccer ball 106.

In one embodiment where the portable electronic device 306 utilizes a touch screen display, the individual 10 may tap the animated spinning ball icon 602 to stop the spinning animation. In other embodiments, other forms of user input may be used to stop the spinning animation. When the spinning animation is stopped, in some embodiments, a point of impact icon 612 is overlaid on top of a now static ball icon 602, where the point of impact icon 612 is representative of the calculated point of impact 150, as described above with respect to FIGS. 26 and 27. In other embodiments, the point of impact icon 612 may be displayed over a still spinning animated spinning ball icon 602, or a spinning ball icon 602 that has reduced its rate of spinning to better allow for viewing of the point of impact icon 612. In embodiments where the spinning animation is stopped by the individual 10 tapping the ball icon 602, the individual 10 re-tapping the stopped icon may restart the spinning.

In this way, the ball flight path, ball strike, and ball spin visual display and feedback features illustrated in FIGS. 25-28 can provide an individual 10 with useful and visually interesting feedback on the motion characteristics of their kicks of a sport ball 106, such as a soccer ball 106. As previously noted, in some embodiments, the statistical display bar 606 may provide an indication of whether the individual 10 has designated a particular kick as a "favorite" kick. The individual 10 may designate a kick as a favorite kick after reviewing their feedback while viewing a display such as those of FIGS. 25-28 by providing a user input to portable electronic device 306, such as by tapping a "favorite" icon. The motion monitoring system 100 will then save a record of the kick being a favorite kick of the individual 10 in a memory device in one or more of the portable electronic device 306, or at a remote server 302.

Figure 29:
FIG. 29 is a graphical user interface for a sport ball motion monitoring application according to an embodiment of the present invention.
Figure 29:
Figure 29:
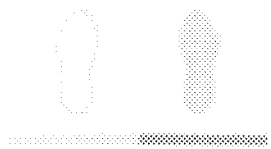

Embodiments of the present invention may also provide for live video recording of kicks that can provide additional feedback to the individual 10 on their kick. FIG. 29 is an exemplary GUI window that may be provided by the kick it module that includes a video element 610 icon to enable this functionality. In one embodiment, the video element 610 icon may only be displayed if the individual's 10 portable electronic device 306 includes or is paired to a suitable video recording component, such as a digital video camera of the portable electronic device 306. FIG. 29 also shows a prompt to tap the ball icon 602 when they are ready to monitor a kick using the motion monitoring system 100, similar to the display depicted in FIG. 24. If not previously selected, the individual 10 may activate a selection video element 610 icon for indicating a desire to use the video recording features. When the ball icon 602 is tapped indicating a desire to proceed with a kick with the video features enabled, in one embodiment, the GUI background may appear with a view of a live video feed from the video camera of the portable electronic device 306.

Figure 30:
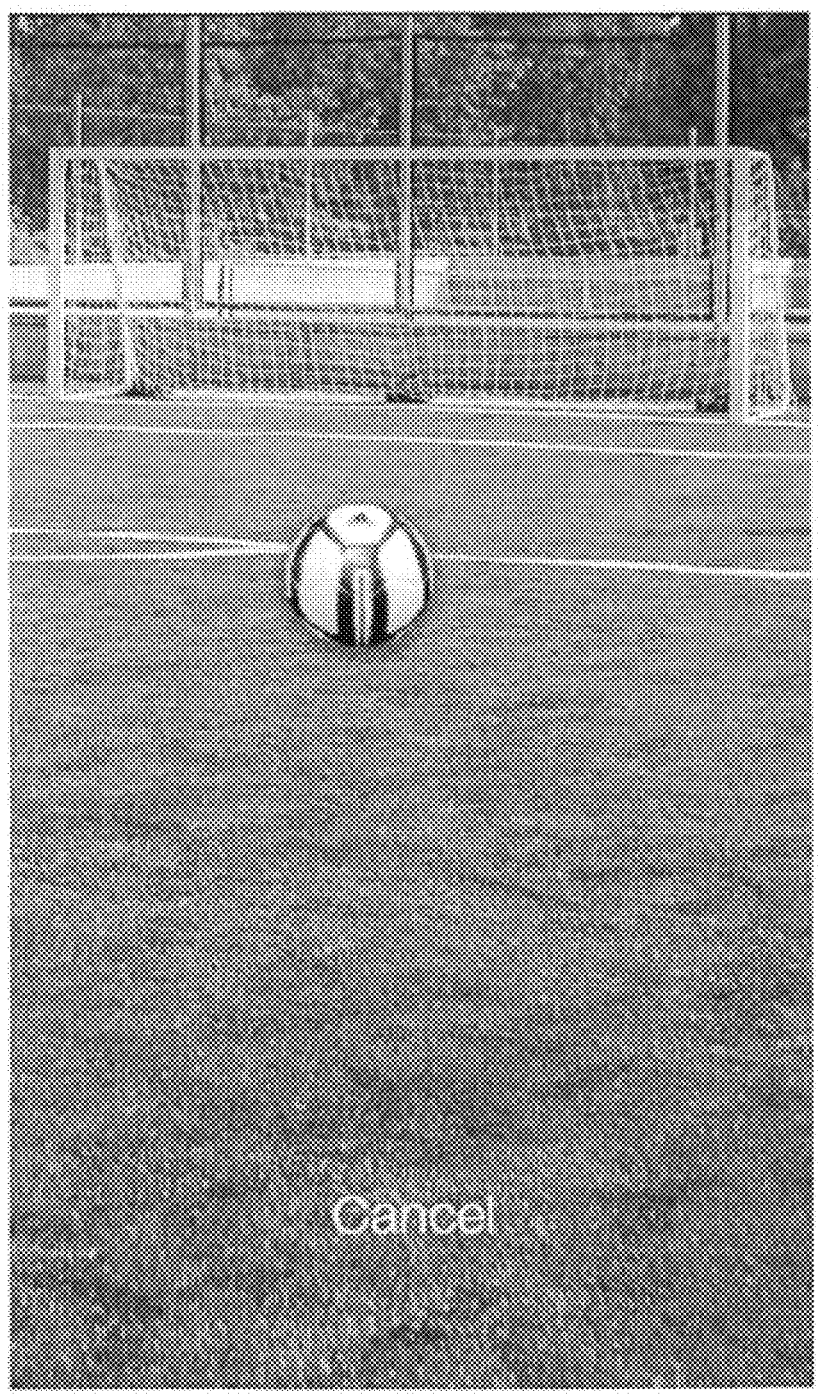
FIG. 30 is a graphical user interface for a sport ball motion monitoring application according to an embodiment of the present invention.

FIG. 30 is an exemplary GUI window showing a view of a live video feed from the video camera of the portable electronic device 306. In this example, the individual 10 has oriented the portable electronic device 306 and its camera such that the soccer ball 106 and an intended soccer goal are visible, including the individual's 10 likely approach route to the soccer ball 106 and the soccer ball's 106 likely flight path area. An individual 10 may achieve this portable electronic device 306 and camera orientation by, for example, having a friend or coach hold and position the portable electronic device 306 or by setting the portable electronic device 306 on the ground or other surface, with or without a stand or other support.

As previously described, in response to receiving an indication that the individual 10 is ready to monitor a kick (e.g. the individual 10 taps the ball icon 602), the portable electronic device 306 may communicate with the soccer ball 106 having a sensor module 102 to notify the soccer ball 106 to expect a kick. In another embodiment, the soccer ball 106 may send a return signal to the portable electronic device 306 to indicate that the soccer ball 106 is ready to be kicked. As this data communicating process is occurring, in one embodiment, the portable electronic device 306 may continue to present a GUI background with a view of a live video feed from the video camera of the portable electronic device 306, possibly with status updates displayed overlaying the live video feed informing the individual 10 of the communication status and finally informing the individual 10 that they may kick the soccer ball 106.

When the soccer ball 106 is kicked, the sensor module 102 is capable of recording movement date associated with the kick, as described above with respect to FIGS. 8-21. The soccer ball 106 having the sensor module 102, alone or in combination with the portable electronic device 306, may be capable of determining motion characteristics of the soccer ball 106 including ball speed, ball spin rate, ball spin axis, and ball launch angle, as previously described. In another embodiment, the video camera of the portable electronic device 306 may record a video that captures a result of the impact of the sport ball by the individual during the course of an athletic activity, and use video motion analysis techniques to determine motion characteristics of the soccer ball 106 including ball speed, ball spin rate, ball spin axis, and ball launch angle. In other embodiments, these motion characteristics of the soccer ball 106 may be determined using both sensor module 102 and video motion analysis techniques to increase accuracy.

Figure 31:
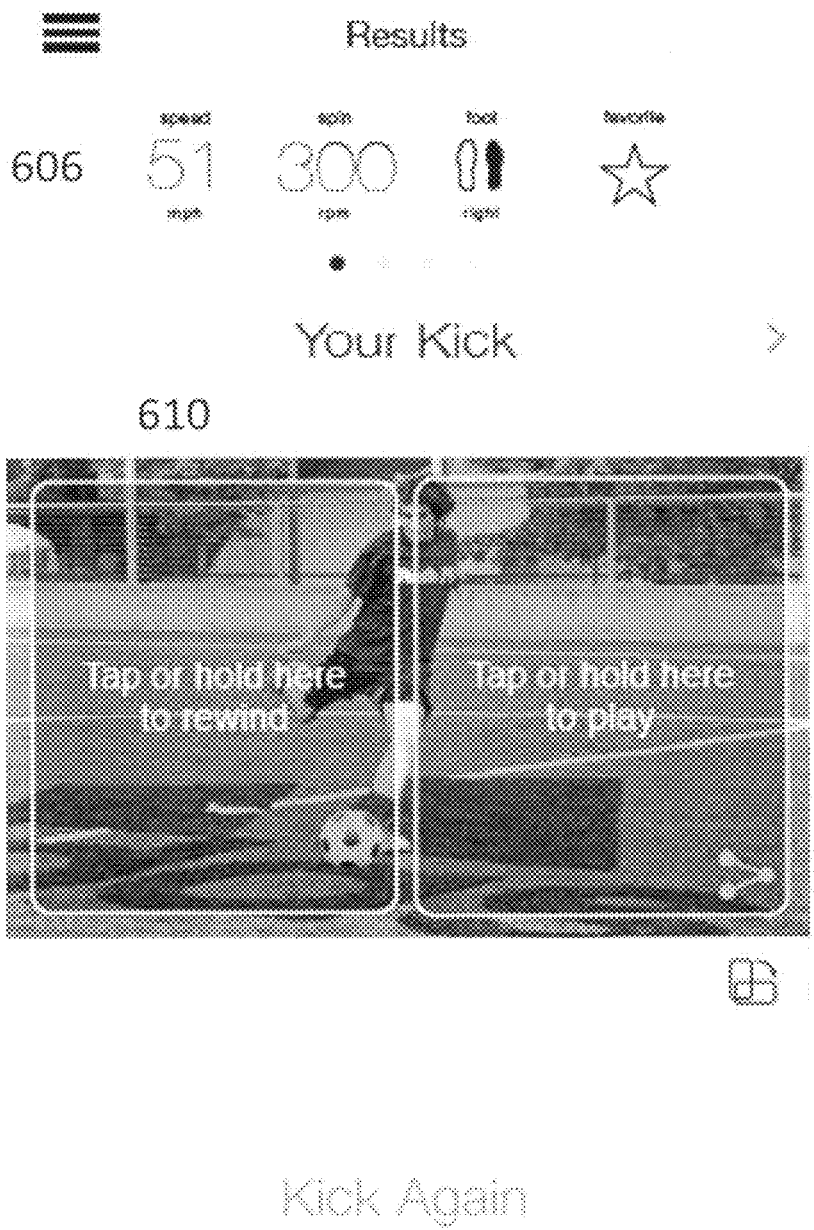
FIG. 31 is a graphical user interface for a sport ball motion monitoring application according to an embodiment of the present invention.

When the video features of the present invention are enabled, FIG. 31 is an exemplary GUI window that may be provided by the kick it module that provides a visual display to the individual 10 giving them feedback about the motion characteristics of the soccer ball 106 during their kick, including video feedback.

As with previous exemplary GUIs discussed, the exemplary GUI of FIG. 31 includes a statistical display bar 606 that may provide, for example, information on the maximum speed of the soccer ball 106 during the post-kick flight or information on the maximum spin rate of the soccer ball 106 during the post-kick flight. In some embodiments, the statistical display bar 606 may also provide an indication of which foot 12 the individual 10 kicked the soccer ball 106 with, as well as an indication of whether the individual 10 has designated the kick as a "favorite" kick. The exemplary GUI of FIG. 31 also includes a video element 610.

In one embodiment, video recording is enabled as soon as the individual 10 enters an input to the portable electronic device 306 indicating that video recording is desired. In another embodiment, however, nothing is recorded by the motion monitoring system 100 until the soccer ball 106 is kicked, or until another event has occurred.

In another embodiment of the present invention, the portable electronic device 306 may process video data in a temporary buffer memory and later store video data in a more permanent memory file only after it is determined that the memory device of the sport ball 306 has reached a certain level of capacity. This video data processing procedure may be similar to the system described for managing acceleration data storage on the memory of the sport ball 106 using a circular buffer previously described above.

After the kick, the video may be auto-clipped at, for example, two seconds prior to the memory device of the sport ball 306 reaching a certain level of capacity, such as 10% full, and then clipped again, for example, six seconds later, for a final eight-second video. This approach captures the duration of a typical kick and generates a video that is reasonably sized for sharing via a variety of social media or other communication channels. In another embodiment, if the individual 10 proceeds to conduct and take video recordings of additional kicks, the software application may auto-clip the video again once additional kicks are initiated to create an even shorter clip to further save on memory space.

In an embodiment, the video may initially display as a still image on the display screen, prompting the individual 10 to tap the screen. Simple text overlays may be provided to explain the desired user interface interaction, and may fade out once the screen is tapped. In an embodiment, when the screen is tapped the video will advance one frame either forwards or backwards depending on the tap location. For example, the right half of the screen may advance the video forward, while the left half of the screen may advance the video backward. Enabling the individual 10 to advance the video one frame at a time in this manner may aid in carefully examining the individual's 10 form during a kick as well as the flight path and characteristic of the soccer ball 106 during the kick. In this way, the individual 10 is provided with both recorded video feedback as well as the calculated feedback described above.

The embodiment depicted in FIG. 31 includes a statistical display bar 606 that may provide, for example, information on the maximum speed of the soccer ball 106 during the post-kick flight or information on the maximum spin rate of the soccer ball 106 during the post-kick flight at the top of the display. In some embodiments, instead of always displaying maximum speed and maximum spin rate, the statistical display bar 606 may display an instantaneous speed and spin rate that are correlated with the displayed video feedback. For example, the motion monitoring system 100 software application may correlate speed, spin rate, and other motion data with the displayed video feedback based on the time associated with the motion data and each individual video frame. In this way, as the individual 10 advances the video frame-by-frame either forwards or backwards in slow motion or at a faster pace, the statistical display bar 606 may change the value for the speed, spin rate, and other motion data displayed to match what was determined for the point in time corresponding to the current video image being shown.

While viewing the video display screen, a swipe element 608 may indicate to the individual 10 that swiping their finger across the display screen may lead to other pages that display additional feedback, such as the exemplary pages shown in FIGS. 25-28.

As noted above with respect to FIG. 22, the individual 10 may navigate to a menu 600 GUI that includes several icons or indicia corresponding to, for example, kick it, get better, challenges, and record book modules, as well as icons or indicia corresponding to settings or help features. The individual 10 may cause different GUI pages to be provided by different modules by selecting their corresponding icons using user input controls. Additional icons corresponding to sub-modules or program wizards associated with a particular module may pop up or otherwise be displayed to the individual 10 if the individual 10 selects, swipes, or hovers over a module icon with a cursor.

Figure 32:
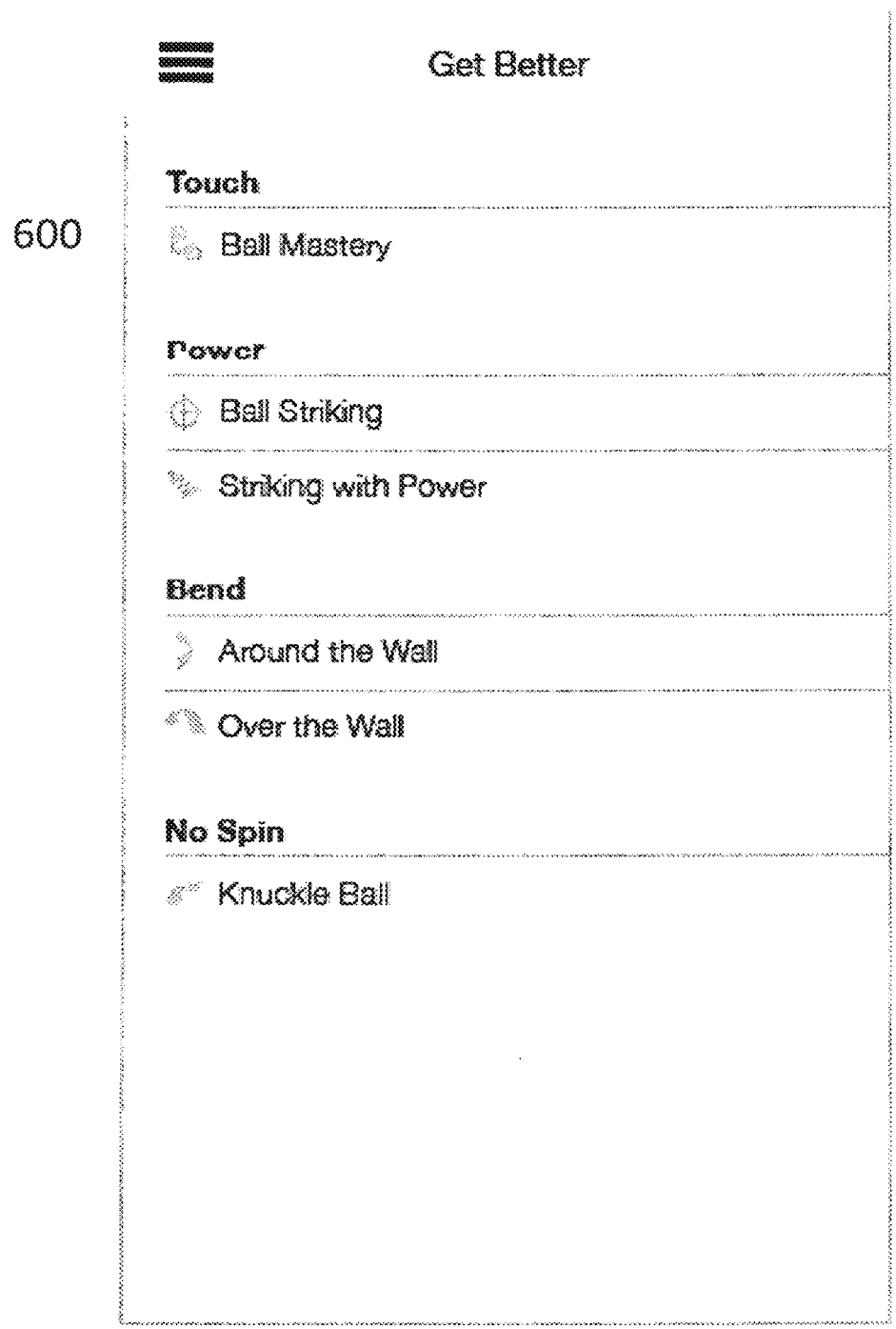
FIG. 32 is a graphical user interface for a sport ball motion monitoring application according to an embodiment of the present invention.

FIG. 32 is an exemplary GUI window depicting a get better menu GUI that includes several icons or indicia corresponding to several different sub-modules offering training via several different drills for specific sport ball 106 performance skills, such as particular soccer ball 106 kicking skills. Sub-modules may exist for drills to enhance the individual's 10 general form in kicking a soccer ball 106, their ability to generate a more powerful kick, their ability to bend a soccer ball 106 with a kick (i.e. impart desired relatively high level of spin), and their ability to kick a knuckle ball (i.e. kick a ball with little or no spin). In one embodiment, specific ball mastery, ball striking, striking with power, around the wall, over the wall, and knuckle ball modules are offered.

When a ball mastery sub-module is selected and executed by the portable electronic device 306 for the individual 10, a display of the portable electronic device 306 may provide the individual 10 with a menu of training videos to choose from. The training videos may provide the individual 10 with instructions and examples of how to execute general soccer ball 106 handling movements. Videos, still images, audio, and/or text may be provided to the individual 10. For example, in one embodiment the individual 10 may be presented with instructions for executing toe taps and outside rolls. A video of toe taps and outside rolls may be provided. Before, after, or during the video, audio or text may inform the individual 10 that they should start slowly, be on their toes and add a little hop when they roll outside, and that both of their feet should be working together, using both the inside and soles of the feet. In some embodiments, the soccer ball 106 having a sensor module 102 may be used to monitor the individual's 10 execution of the toe taps and outside roll maneuver and provide feedback on the performance.

In one embodiment of the present invention, the videos and/or still images may provide the individual 10 with instructions and examples of how to execute general soccer ball 106 handling movements that provide guidance, in part, based on exterior markings 202 of the soccer ball 106, such as those briefly noted above with respect to FIGS. 5 and 16. In addition to exterior markings 202 being useful to indicate the optimum orientation of soccer ball 106 for charging, such exterior markings 202 may additionally or alternatively be useful to help the individual 10 properly orient their soccer ball 106 prior to a kick and to serve as landmarks for their intended point of impact 150 with the soccer ball 106. For example, in the exemplary embodiment of FIG. 16, the illustrated point of impact 150 is vertically aligned with the linear exterior markings 202 on the front face and center of the soccer ball 106. In an embodiment, instructions and examples of how to kick a soccer ball 106 may incorporate references to locations of one or more exterior markings 202, such as a videos and/or still images showing the individual 10 that they should attempt to kick the soccer ball 106 with their foot 12 so that the point of impact 150 is vertically aligned with the central linear exterior marking 202.

In another embodiment, when a ball striking sub-module is selected and executed by the portable electronic device 306 for the individual 10, a display of the portable electronic device 306 may provide the individual 10 with instructions on general soccer ball 106 kick striking tips. Videos, still images, audio, and/or text may be provided to the individual 10. For example, in one embodiment the individual 10 may be presented with instructions for general soccer ball 106 kick striking. A video of general soccer ball 106 kick striking may be provided. Before, after, or during the video, audio or text may inform the individual 10 that they should plant their foot 12, strike the soccer ball 106, and follow through. For example, the individual 10 may be instructed to "land on your plant foot just behind the ball with it pointed toward the target, and allow enough space between your plant foot and the ball to ensure full extension of your kicking foot." An accompanying video, animation, or still image may be provided for guidance. The individual 10 may also be instructed to "keep your foot pointed down with your ankle locked as you swing your leg to strike, and drive the top of your boot squarely into the center of the ball," and to "make sure you focus on the connection with ball before lifting your head and going into your follow through, and keep your follow through relatively low for this type of strike." Again, an accompanying video, animation, or still image may be provided for guidance, and they may incorporate references to locations of one or more exterior markings 202 of the soccer ball 106. At this point, the individual 10 may then be tested on their comprehension and mastery of this skill.

In response to receiving an indication that the individual 10 is ready to monitor a kick (e.g. the individual 10 taps the ball icon 602) to test their general soccer ball 106 kick striking skills via the ball strike sub-module, the portable electronic device 306 may communicate with the soccer ball 106 having a sensor module 102 to notify the soccer ball 106 to expect a kick, as previously described. When the soccer ball 106 is kicked, the sensor module 102 is capable of recording movement date associated with the kick, as described above with respect to FIGS. 8-21. The soccer ball 106 having the sensor module 102, alone or in combination with the portable electronic device 306, may be capable of determining motion characteristics of the soccer ball 106 including ball speed, ball spin rate, ball spin axis, and ball launch angle, as previously described.

Figure 33:
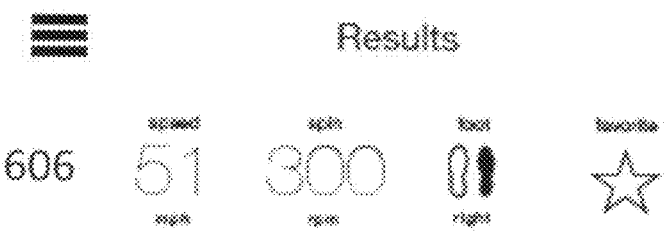
FIG. 33 is a graphical user interface for a sport ball motion monitoring application according to an embodiment of the present invention.
Figure 33:
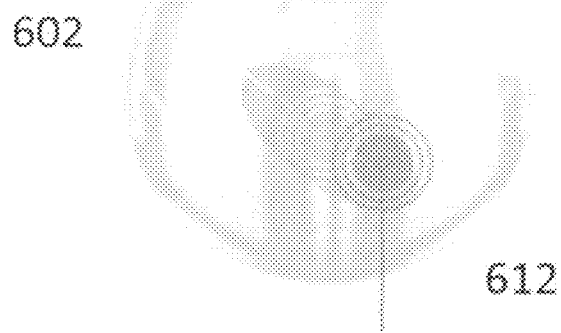

When the individual 10 is testing their general soccer ball 106 kick striking skills via the ball strike sub-module, FIG. 33 is an exemplary GUI window that may be provided showing a visual display to the individual 10 giving them feedback about the motion characteristics of the soccer ball 106 during their kick, including feedback on whether they were properly striking the soccer ball 106, as evidenced in part by their point of impact 150. As with previous exemplary GUIs discussed, the exemplary GUI of FIG. 33 includes a statistical display bar 606 that may provide, for example, information on the maximum speed of the soccer ball 106 during the post-kick flight or information on the maximum spin rate of the soccer ball 106 during the post-kick flight. The exemplary GUI of FIG. 33 also illustrates a point of impact icon 612 overlaid on top of a ball icon 602, where the point of impact icon 612 is representative of the calculated point of impact 150 derived from the regression process 460 analysis as described above with respect to FIGS. 16-21. In other words, the point of impact icon 612 displayed via portable electronic device 306 corresponds to the calculated point of impact 150 that represents the location on the surface of the soccer ball 106 that approximately coincides with the center of the area of the foot 12 in contact with soccer ball 106. In addition, in some embodiments, a desired strike zone 140 and/or point of impact 150 corresponding the preferred strike zone 140 and/or point of impact 150 based on the general soccer ball 106 kick striking tips previously provided may also be displayed.

Accordingly, the methods previously described for analyzing the relationship between the location of the point of impact 150 between an individual's 10 foot 12 and a soccer ball 106 and motion characteristics of the soccer ball 106 during and after it is kicked can be used to generate feedback to the individual 10 via the portable electronic device 306, such as visually illustrating the location of a point of impact icon 612 overlaid on top of a ball icon 602. In this way, the individual 10 can visually see how they need to adjust their kick mechanics to achieve a better kick. In FIG. 33, the individual's 10 recorded point of impact icon 612 appears just below and to the right of the preferred point of impact 150 based on the general soccer ball 106 kick striking tips previously provided may also be displayed. In one embodiment, the motion monitoring system 100 application may provide feedback to the individual 10 that "your kick is a bit low and to the right of the strike zone, you should adjust your kick to strike closer to the center of the ball."

In another embodiment, when a striking with power sub-module is selected and executed by the portable electronic device 306 for the individual 10, a display of the portable electronic device 306 may provide the individual 10 with instructions on general soccer ball 106 kick striking tips to enhance the power (i.e. speed) of a kick. Execution of this sub-module is in many ways similar to the execution of the soccer ball 106 strike module just described. The individual 10 may be provided with videos, animations, audio and/or text explaining how they should plant their foot 12, strike the soccer ball 106, follow through, and make any other necessary adjustments to generate more power (i.e. speed) for their kicks.

Figure 34:
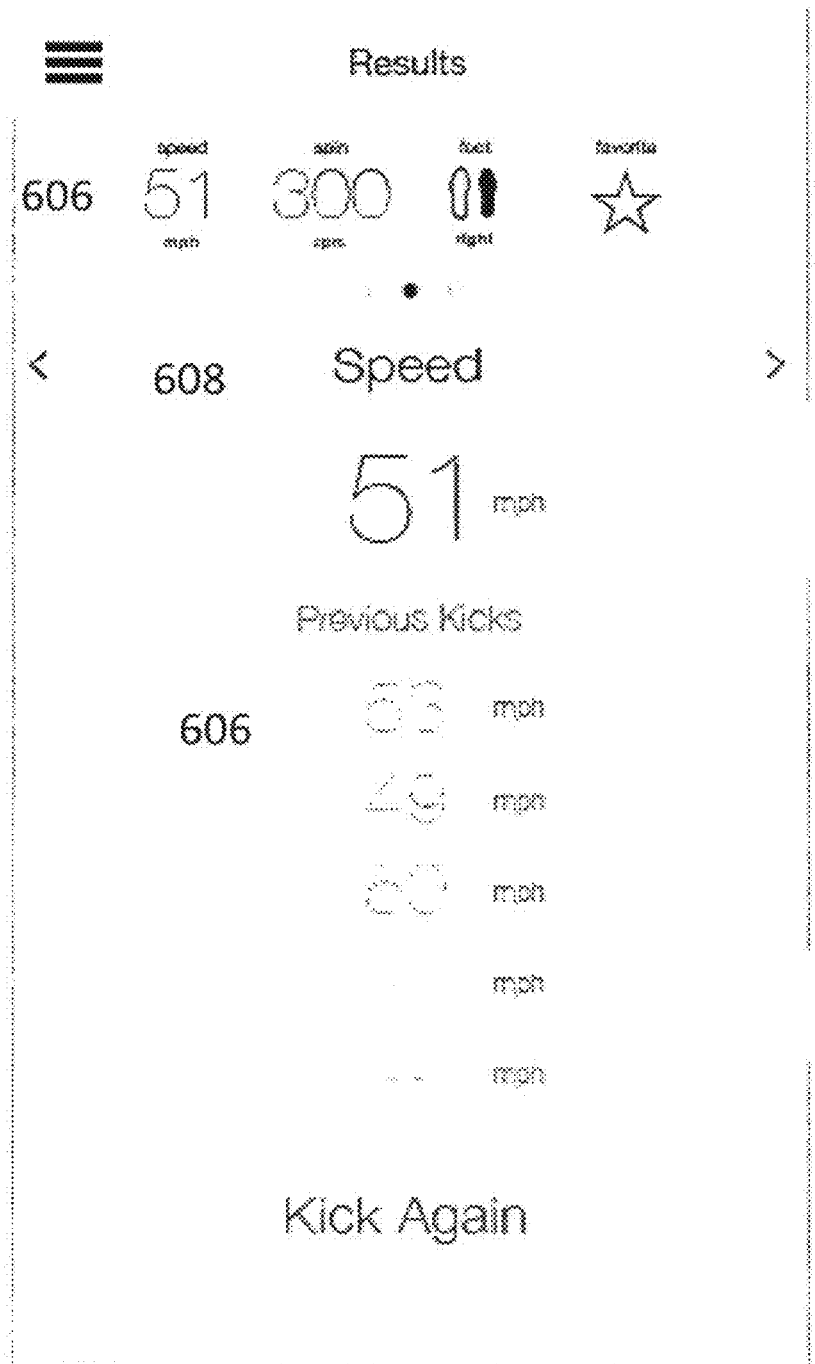
FIG. 34 is a graphical user interface for a sport ball motion monitoring application according to an embodiment of the present invention.

GUIs displayed to provide feedback to the individual 10 for the striking with power sub-module may be similar to those previously described with respect to FIGS. 25-28 and 33. In addition, when the individual 10 is testing their general power soccer ball 106 kick striking skills via the striking with power sub-module, FIG. 34 is an exemplary GUI window that may be provided showing a visual display to the individual 10 giving them feedback about the power characteristics of the soccer ball 106 during their kick, including feedback on the speed of the soccer ball 106. In addition to the statistical display bar 606 that may provide, for example, information on the maximum speed of the soccer ball 106 during the post-kick flight or information on the maximum spin rate of the soccer ball 106 during the post-kick flight at the top of the window, a different statistical display area 606 focused on speed may also be presented. In an embodiment, this statistical display area 606 may include a speed number animation that starts with a display of zero and rapidly builds up to the result. The last five speed readings for recent kicks may also be displayed immediately below. For example, the exemplary embodiment of FIG. 34, an animated display would cycle up from zero miles per hour to a display of 51 miles per hour, and recent kick speeds of 53 and 49 miles per hour would be displayed below this.

In another embodiment, when a bend around the wall sub-module is selected and executed by the portable electronic device 306 for the individual 10, a display of the portable electronic device 306 may provide the individual 10 with instructions on soccer ball 106 kick striking tips to be able to bend a kick (i.e. apply targeted spin) around a defensive wall (i.e. a line of defenders forming a barrier against a free kick taken near the penalty area). Execution of this sub-module is in many ways similar to the execution of the ball strike and striking with power sub-modules just described. The individual 10 may be provided with videos, animations, audio and/or text explaining how they should plant their foot 12, strike the soccer ball 106, follow through, and make any other necessary adjustments to generate bend (i.e. targeted spin) for their kicks. Again, an accompanying video, animation, or still image may be provided for guidance, and they may incorporate references to locations of one or more exterior markings 202 of the soccer ball 106.

Figure 35:
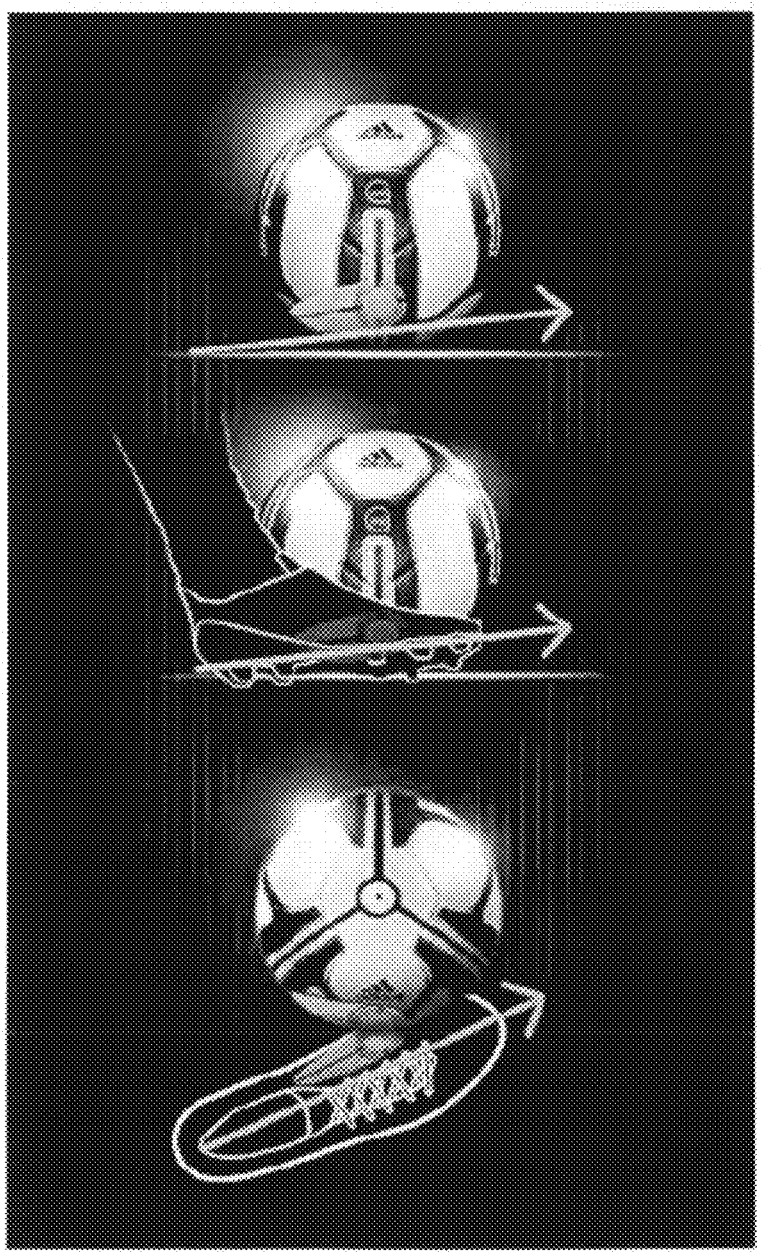
FIG. 35 is a graphical user interface for a sport ball motion monitoring application according to an embodiment of the present invention.

FIG. 35 is an exemplary GUI window that may be provided showing a visual display to the individual 10 giving them video, animated, and/or still image instructions on how generate bend (i.e. targeted spin) for their kicks. For example, the individual 10 may be instructed to "approach the ball from a 45 degree angle" and to "aim to stroke the ball low with your heel close to the turf and lock your ankle throughout the strike." The video, animated, and/or still images, such as the exemplary ones shown in FIG. 35, may further aid the individual 10 in understanding the mechanics needed to achieve the desired outcome. In an embodiment, videos, animations, and/or still images may further be provided illustration what a successful kick around a wall (i.e. around a line of defenders forming a barrier against a free kick taken near the penalty area) would look like. Again, an accompanying video, animation, or still image may be provided for guidance, and they may incorporate references to locations of one or more exterior markings 202 of the soccer ball 106. As shown in FIG. 35, more exterior markings 202 are visible to the individual 10 in the GUI display and can therefore be used for additional guidance landmarks.

Other GUIs displayed to provide feedback to the individual 10 for the bend around the wall sub-module may be similar to those previously described with respect to FIGS. 25-28 and 33. In other words, feedback may be given to the individual 10 regarding the speed, spin, spin axis, launch angle, flight path, and/or point of impact 150 for their kicks.

In another embodiment, when a bend over the wall sub-module is selected and executed by the portable electronic device 306 for the individual 10, display of the portable electronic device 306 may provide the individual 10 with GUIs and feedback very similar to those provided for the bend around the wall sub-module. In an embodiment, the primary difference is in the coaching related to how the individual 10 should plant their foot 12, strike the soccer ball 106, follow through, and make any other necessary adjustments to generate bend (i.e. targeted spin) for their kicks to go over a wall as opposed to around a wall. For example, the individual 10 may be instructed to "approach the ball from a 45 degree angle" and to "aim to stroke the ball low with your heel close to the turf and lock your ankle in an upward motion."

In another embodiment, when a knuckle ball sub-module is selected and executed by the portable electronic device 306 for the individual 10, display of the portable electronic device 306 may provide the individual 10 with GUIs and feedback similar to those provided for the bend around the wall and bend over the wall sub-modules. In an embodiment, the primary difference is in the coaching related to how the individual 10 should plant their foot 12, strike the soccer ball 106, follow through, and make any other necessary adjustments to generate a knuckle ball (i.e. kick a soccer ball 106 with little or no spin). For example, the individual 10 may be instructed to "make contact with the ball using the ankle joint center part of your foot looking to hit the ball in the middle to take the bend off." As with previously described embodiments, suitable videos, animations, and/or still images may further be provided illustration what a successful knuckle ball kick would look like. Again, an accompanying video, animation, or still image may be provided for guidance, and they may incorporate references to locations of one or more exterior markings 202 of the soccer ball 106.

Figure 36:
FIG. 36 is a graphical user interface for a sport ball motion monitoring application according to an embodiment of the present invention.
Figure 36:

GUIs displayed to provide feedback to the individual 10 for the knuckle ball sub-module may be similar to those previously described with respect to FIGS. 25-28 and 33. In addition, when the individual 10 is testing their knuckle ball kick striking skills via the knuckle ball sub-module, FIG. 36 is an exemplary GUI window that may be provided showing a visual display to the individual 10 giving them feedback about the spin characteristics of the soccer ball 106 during their kick. In addition to the statistical display bar 606 that may provide, for example, information on the maximum speed of the soccer ball 106 during the post-kick flight or information on the maximum spin rate of the soccer ball 106 during the post-kick flight at the top of the window, a different statistical display area 606 focused on speed may also be presented. In an embodiment, this statistical display area 606 including a ball icon 102 may be provided.

As shown in FIG. 36, a series of concentric circles in a "bull's-eye" style configuration may provide several spin ranges, with the inner most circle being a relatively high spin range (e.g. over 200 revolutions per minute) and the outer most circle being a relatively low spin range (e.g. 0 to 20 revolutions per minute). For a kick registering a relatively high spin rate (e.g. 300 rpm), a ball icon 102 may appear in the center of the bull's-eye with the rate of 300 rpm shown. But as shown in FIG. 36, for a kick registering a relatively low spin rate (e.g. 12 rpm), a series of ball icons 102 may be illustrated as moving outward from the center of the bull's-eye toward the outer low-spin ring, this giving the impression of a soccer ball 106 moving without much spin—in other words a knuckle ball. In this way, the individual 10 is provided with additional visual feedback on how they are progressing to meeting their goal of kicking a knuckle ball in accordance with the guidelines of the knuckle ball sub-module.

As noted above with respect to FIG. 22, the individual 10 may navigate to a menu 600 GUI that includes several icons or indicia corresponding to, for example, kick it, get better, challenges, and record book modules, as well as icons or indicia corresponding to settings or help features. The individual 10 may cause different GUI pages to be provided by different modules by selecting their corresponding icons using user input controls. Additional icons corresponding to sub-modules or program wizards associated with a particular module may pop up or otherwise be displayed to the individual 10 if the individual 10 selects, swipes, or hovers over a module icon with a cursor.

Figure 37:
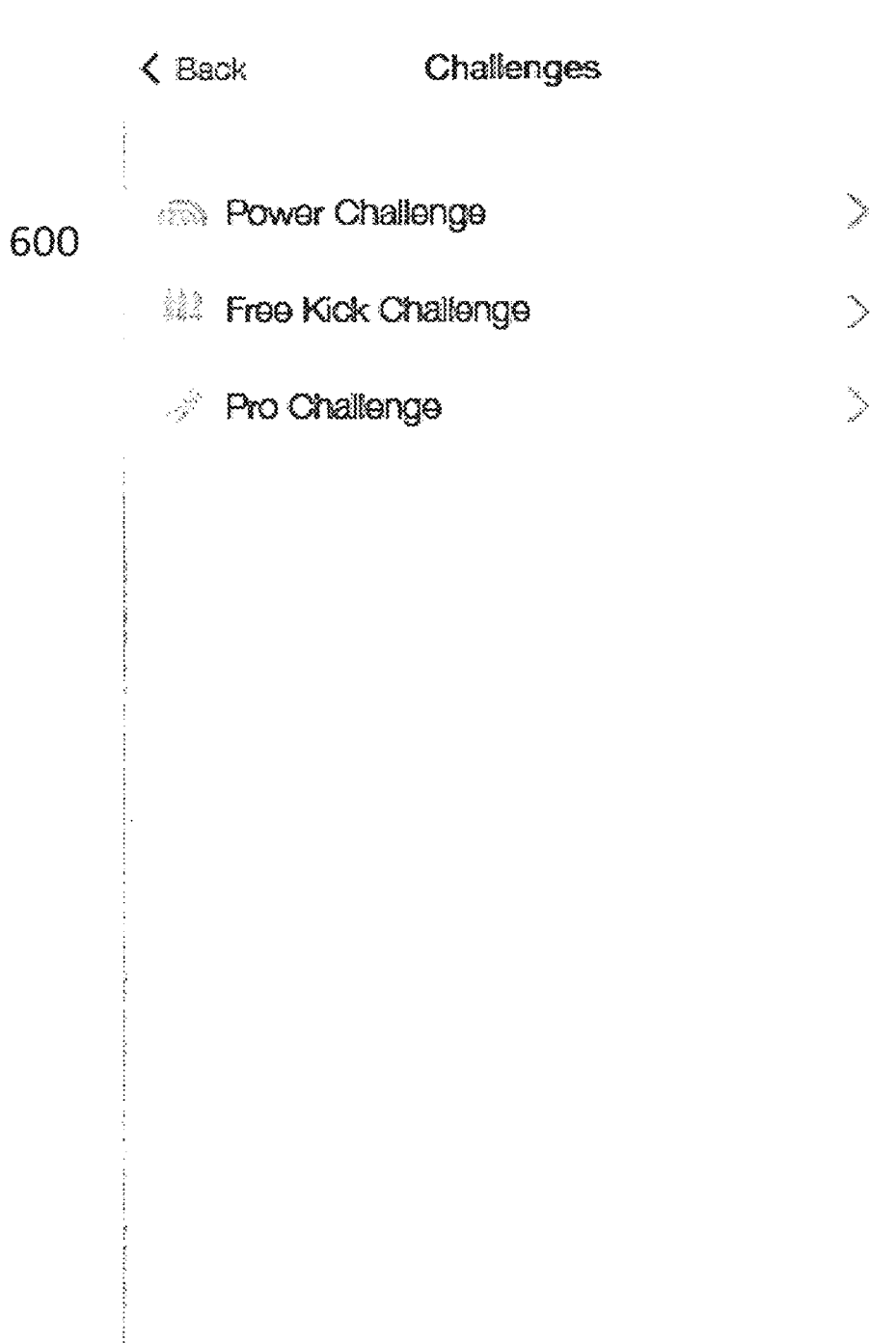
FIG. 37 is a graphical user interface for a sport ball motion monitoring application according to an embodiment of the present invention.

FIG. 37 is an exemplary GUI window depicting a challenges menu GUI that includes several icons or indicia corresponding to several different sub-modules offering additional ways for an individual 10 to further train or test their soccer ball 106 kicking skills. Sub-modules may exist for drills to improve or to test the individual's 10 ability to control their kick power (i.e. speed), control the bend of their kick (i.e. spin), or to mimic the power, bend, flight trajectory, or other characteristics of a sample kick from a professional soccer player. In one embodiment, specific power challenge, free kick challenge, and pro challenge modules are offered.

Figure 38:
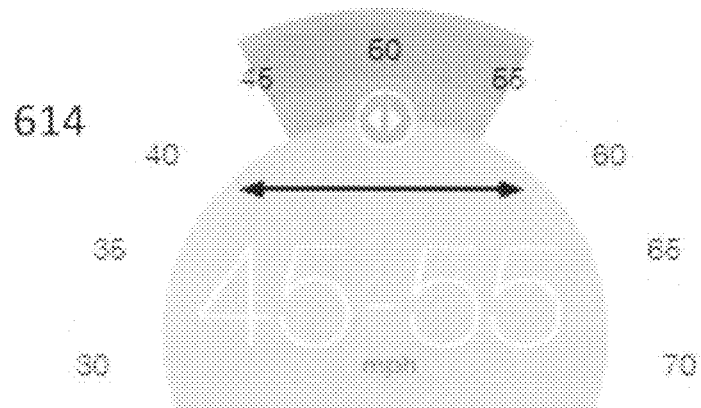
FIG. 38 is a graphical user interface for a sport ball motion monitoring application according to an embodiment of the present invention.
Figure 38:
Figure 39:
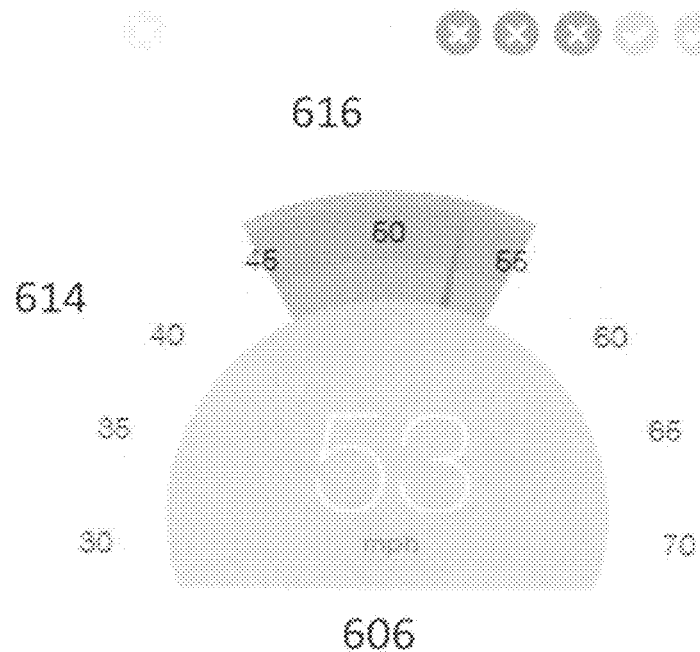
FIG. 39 is a graphical user interface for a sport ball motion monitoring application according to an embodiment of the present invention.
Figure 40:
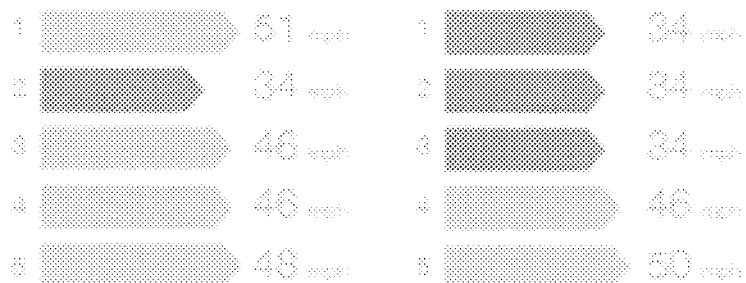
FIG. 40 is a graphical user interface for a sport ball motion monitoring application according to an embodiment of the present invention.
Figure 40:
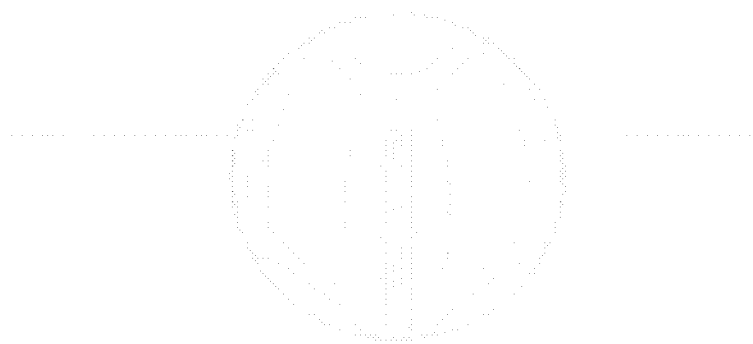
Figure 40:

When a power challenge sub-module is selected and executed by the portable electronic device 306 for the individual 10, a display of the portable electronic device 306 may provide the individual 10 with feedback on their control their kick power (i.e. speed), such as via the exemplary GUI windows of FIGS. 38-40.

FIG. 38 is an exemplary GUI window illustrating features of the power challenge sub-module. Initially, when a power challenge sub-module is selected and executed by the portable electronic device 306 for the individual 10, display of the portable electronic device 306 may provide the individual 10 with GUIs and feedback similar to those described above. As with previously described embodiments, suitable videos, animations, and/or still images may be provided.

In on embodiment, a selection icon 604 in the form of a range selector may be presented to allow the individual 10 to set a desired kick speed range. For example, kick speed ranges may be set to have ranges of five, ten, or fifteen miles per hour. In the embodiment illustrated in FIG. 38, a ten mile per hour range has been selected, meaning that the individual's 10 goal will be to kick the soccer ball 106 at a speed that falls within a ten mile per hour range—here, 45 to 55 miles per hour. FIG. 38 also depicts a range wheel 614 that visually depicts the selected range of target kick speeds. In an embodiment, after initially selecting a speed range via the selection icon 604, the individual 10 can adjust the range by a user input such as a touch screen interface. For example, the individual 10 could rotate the range wheel 614 such that the ten mile per hour range covers a different range of speeds that are higher or lower that the initially presented speeds. In another embodiment, the individual 10 could expand or reduce the range by pinching or stretching over the portion of the range wheel icon that highlights the selected range. As shown in GIF. 38, the range wheel icon may also display the numerical range of the desired speeds in its center.

In some embodiments, the power challenge sub-module present the individual 10 with a solo challenge. In other embodiments, the power challenge sub-module can present the challenge to two or more individuals 10 so that they can compete against each other. A selection icon 604, such as that depicted in FIG. 38, may allow the individual 10 to choose whether to engage in a solo challenge or whether to compete against two or more individuals 10.

When the individual 10 is ready to begin the challenge, they may be presented with a prompt to tap a ball icon 602 when they are ready to monitor a kick using the motion monitoring system 100, similar to the display depicted in FIG. 24. In some embodiments, the GUIs displayed to provide feedback to the individual 10 for the power challenge may be similar to those previously described with respect to FIGS. 25-28 and 34. In addition, when the individual 10 is engaged in a power challenge, FIG. 39 is an exemplary GUI window that may be provided showing a visual display to the individual 10 giving them feedback about their control of power (i.e. speed) characteristics of the soccer ball 106 during their kicks.

The exemplary embodiment of FIG. 39 depicts a scorecard 616 at the top of the display. The depicted embodiment is a challenge between two players, Player 1 and Player 2. The scorecard 616 provides information on how many kicks each player has taken, and how many kicks each player is made. In one embodiment, the motion monitoring system 100 application running on the portable electronic device 306 will prompt the players to switch off during the course of the challenge, with Player 1 kicking one ball, then Player 2 kicking one ball, trading off until each player has kicked a maximum number of balls, such as five each.

For each kick, in one embodiment, the application may display a statistical display 606 overlaid on top of the range wheel 614, as shown in FIG. 39. In this exemplary embodiment the range wheel 614 previously shown when setting up the challenge may be presented again, while an arm is displayed overlaid on top of the range wheel pointing to the speed value associated with the individual's 10 last kick. In the depicted embodiment, the last kick was 53 miles per hour, resulting in the numerical display of 53 miles per hour, as well as the display of a dial arm pointing to a value of 53 miles per hour, which falls inside of the predetermined speed challenge range of 45 to 55 miles per hour. Because such a kick would be a successful kick in the challenge, the scorecard 616 would be updated to reflect a successful kick for that individual 10.

FIG. 40 is an exemplary GUI window illustrating an additional power challenge feedback display, which could also serve as a final summary display for the challenge. As shown in this figure, a power challenge for kicks in the range of 45-55 miles per hour between two players named Tom and Julio was completed. As shown by the scorecard 616, which has a different appearance than the scorecard 616 of FIG. 39, Tom successfully completed his first, third, fourth, and fifth kicks, but his second kick was only 34 miles per hour, which was under the goal range of 45-55 miles per hour. On the other hand, Julio only successfully completed his fourth and fifth kicks, with his first three kicks being only 34 miles per hour, which was under the goal range of 45-55 miles per hour. Accordingly, Tom is declared the winner of the two-player power challenge.

A power challenge conducted as a solo challenge with only one player would proceed similarly to the two-player challenge outlined above, except that the individual 10 could take all five of their shots in sequence without interruption from another player. In another embodiment, if a two-player challenge is tied at the end of the set amount of kicks (e.g. five kicks each), the challenge may proceed to "sudden death" rounds where the players would trade off one kick at a time until one player failed to meet their goal in a round where the other player did meet their power goal.

Figure 41:
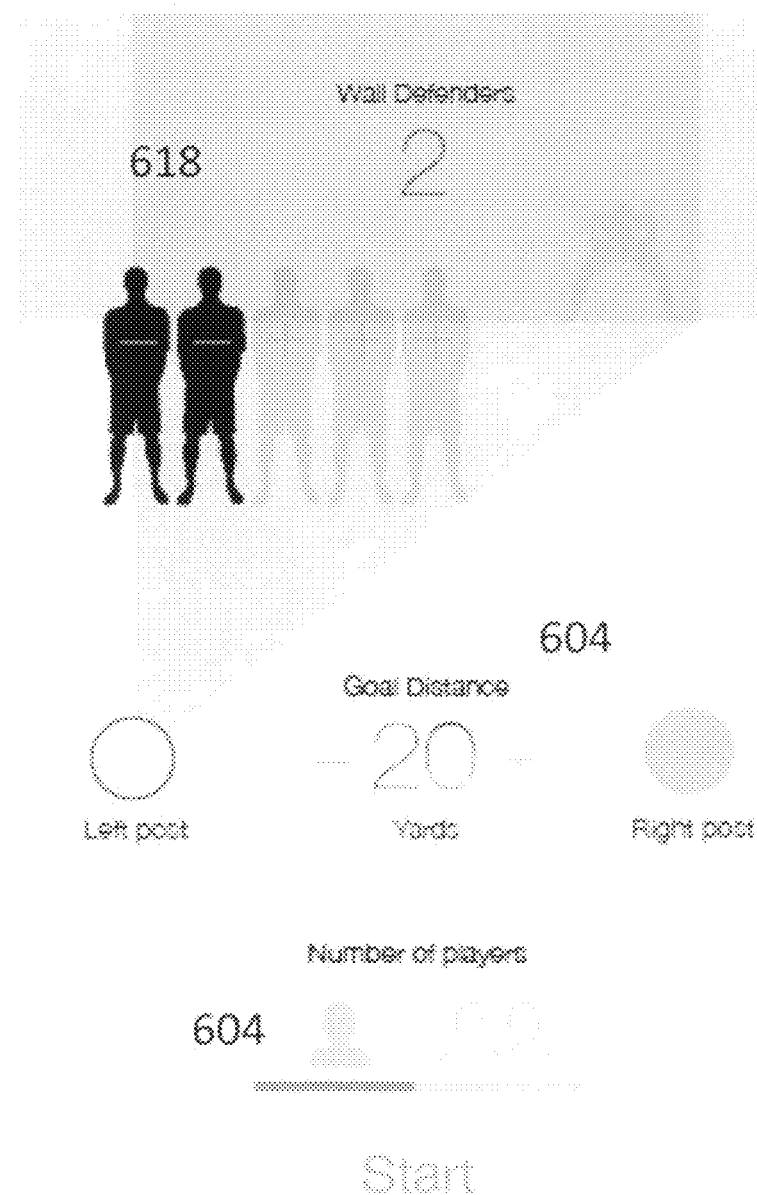
FIG. 41 is a graphical user interface for a sport ball motion monitoring application according to an embodiment of the present invention.
Figure 42:
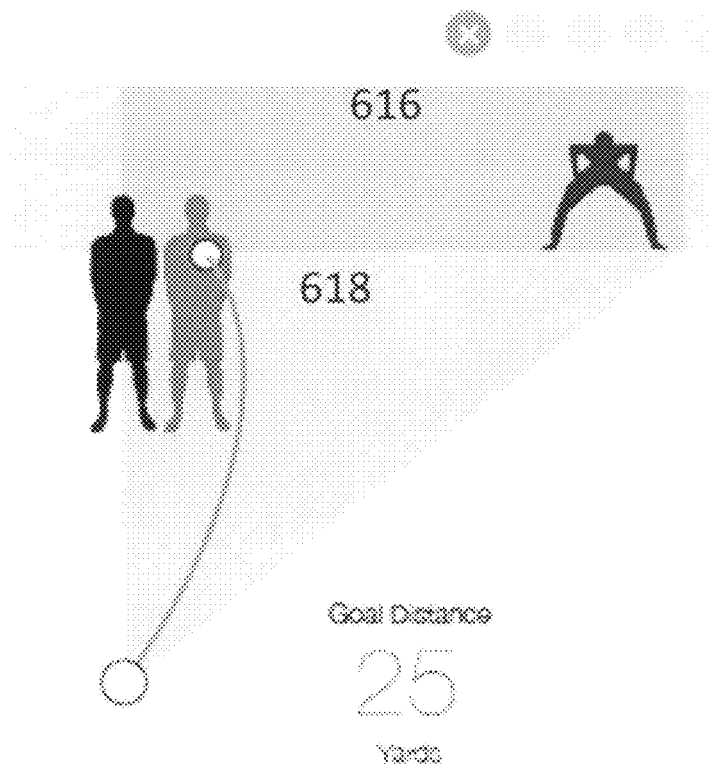
FIG. 42 is a graphical user interface for a sport ball motion monitoring application according to an embodiment of the present invention.
Figure 43:
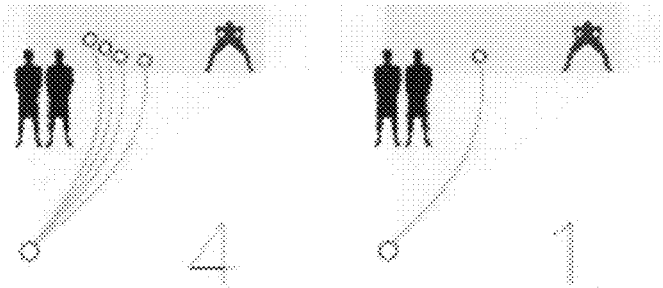
FIG. 43 is a graphical user interface for a sport ball motion monitoring application according to an embodiment of the present invention.
Figure 43:
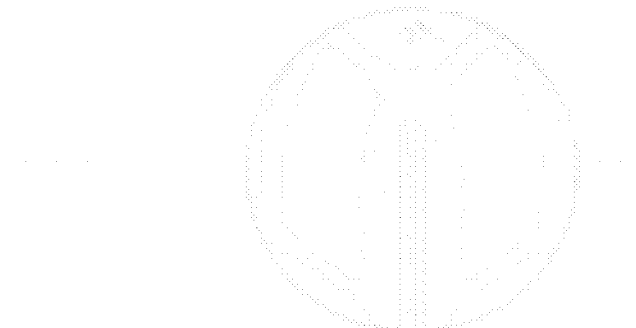
Figure 43:

When a free kick challenge sub-module is selected and executed by the portable electronic device 306 for the individual 10, a display of the portable electronic device 306 may provide the individual 10 with feedback on their control the bend of their kick (i.e. spin), such as via the exemplary GUI windows of FIGS. 41-43.

FIG. 41 is an exemplary GUI window illustrating features of the free kick challenge sub-module. Initially, when a free kick challenge sub-module is selected and executed by the portable electronic device 306 for the individual 10, display of the portable electronic device 306 may provide the individual 10 with GUIs and feedback similar to those described above. As with previously described embodiments, suitable videos, animations, and/or still images may be provided.

In one embodiment, a wall icon 618 may be presented representing one or more defenders arranged in a "wall" formation to oppose a player taking a free kick toward a goal. As shown in FIG. 41, the wall icon 618 may numerically indicate the number of defenders making up the wall and may further graphically illustrate each wall defender. In some embodiments, the individual 10 may increase or decrease the number of wall defenders by entering an input into the portable electronic device 306, which will change the numerical indication of the number of wall defenders as well as the graphical illustration of the wall defenders.

FIG. 41 also illustrates a selection icon 604 in the form of a goal distance selector that may be presented to allow the individual 10 to set a desired kick distance (i.e. distance from the goal). For example, selection icon 604 may allow the individual 10 to increase the distance to the goal in increments of five yards. The exemplary embodiment of FIG. 41 also includes a selection icon 604 for aligning the wall defenders with the left post of the goal or the right post of the goal. Increasing or decreasing the number of defenders, increasing or decreasing the distance to the goal, and switching the alignment of the wall defenders form the left to the right post will impact the nature of a kick that will successfully score a goal. In one embodiment, increasing the number of wall defenders will decrease the width of zone where a goal could be successfully kicked into the net, which may be illustrated in the GUI display by more wall defender images being added. Similarly, increasing the distance to the goal will effectively decrease the height of zone where a goal could be successfully kicked into the net, which may also be illustrated in the GUI display by a shortening of a rectangle representing the soccer goal. Switching the alignment of the wall defenders between the left or right post will require the individual 10 to be able to bend their soccer ball 106 in one way or another to clear the wall defenders but still make the goal. In some embodiment, as illustrated in FIG. 41, a goalkeeper defender may also be illustrated and may partially block the goal.

In some embodiments, the free kick challenge sub-module may present the individual 10 with an solo challenge. In other embodiments, the free kick challenge sub-module can present the challenge to two or more individuals 10 so that they can compete against each other. A selection icon 604, such as that depicted in FIG. 41, may allow the individual 10 to choose whether to engage in a solo challenge or whether to compete against two or more individuals 10.

When the individual 10 is ready to begin the challenge, they may be presented with a prompt to tap a ball icon 602 when they are ready to monitor a kick using the motion monitoring system 100, similar to the display depicted in FIG. 24. In some embodiments, the GUIs displayed to provide feedback to the individual 10 for the free kick challenge may be similar to those previously described with respect to FIGS. 25-28 and 33. In addition, when the individual 10 is engaged in a free kick challenge, FIG. 42 is an exemplary GUI window that may be provided showing a visual display to the individual 10 giving them feedback about their control of bend (i.e. spin) characteristics of the soccer ball 106 during their kicks.

The exemplary embodiment of FIG. 42 depicts a scorecard 616 at the top of the display, which is similar to the scorecard of FIG. 39. The depicted embodiment is a challenge between two players, Player 1 and Player 2. The scorecard 616 provides information on how many kicks each player has taken, and how many kicks each player is made. In one embodiment, the motion monitoring system 100 application running on the portable electronic device 306 will prompt the players to switch off during the course of the challenge, with Player 1 kicking one ball, then Player 2 kicking one ball, trading off until each player has kicked a maximum number of balls, such as five each.

For each kick, in one embodiment, the application may display a kick flight path overlaid on top of the wall icon 618, as shown in FIG. 42. In this exemplary embodiment the wall icon 618 and accompanying goal background previously shown when setting up the challenge may be presented again, while a kick flight path is displayed overlaid on top of the wall icon 618 and accompanying goal background. In the depicted embodiment, the last kick hit the second member of the wall, resulting in a failure to score a goal. Because such a kick would be an unsuccessful kick in the challenge, the scorecard 616 would be updated to reflect an unsuccessful kick for that individual 10.

FIG. 43 is an exemplary GUI window illustrating an additional free kick challenge feedback display, which could also serve as a final summary display for the challenge. As shown in this figure, a free kick challenge with two wall defenders lined up on the left goal post between two players named Tom and Julio was completed. As shown by the scorecard 616, Tom scored four goals by bending soccer balls 106 around the wall. On the other hand, Julio only successfully scored one goal. Accordingly, Tom is declared the winner of the two-player power challenge. Each of Tom's and Julio's successful goals are illustrated by flight path lines traveling unimpeded into the goal. Although failed goals are not illustrated in FIG. 43, in some embodiment, failed goals such as those blocked by a wall defender or goalie may also be illustrated.

A free kick challenge conducted as a solo challenge with only one player would proceed similarly to the two-player challenge outlined above, except that the individual 10 could take all five of their shots in sequence without interruption from another player. In another embodiment, if a two-player challenge is tied at the end of the set amount of kicks (e.g. five kicks each), the challenge may proceed to "sudden death" rounds where the players would trade off one kick at a time until one player failed to meet make a goal in a round where the other player did make a goal.

Figure 44:
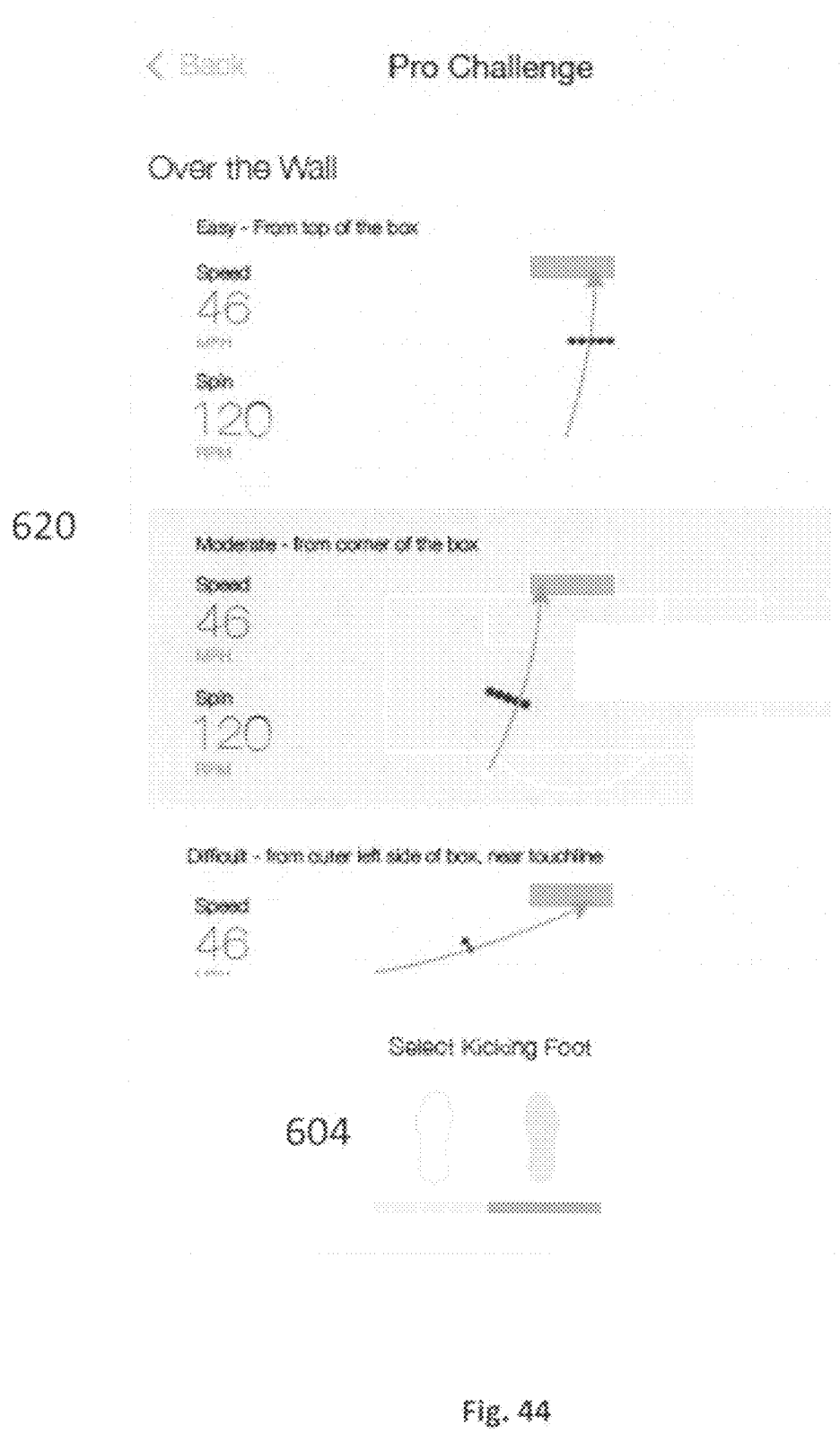
Figure 45:
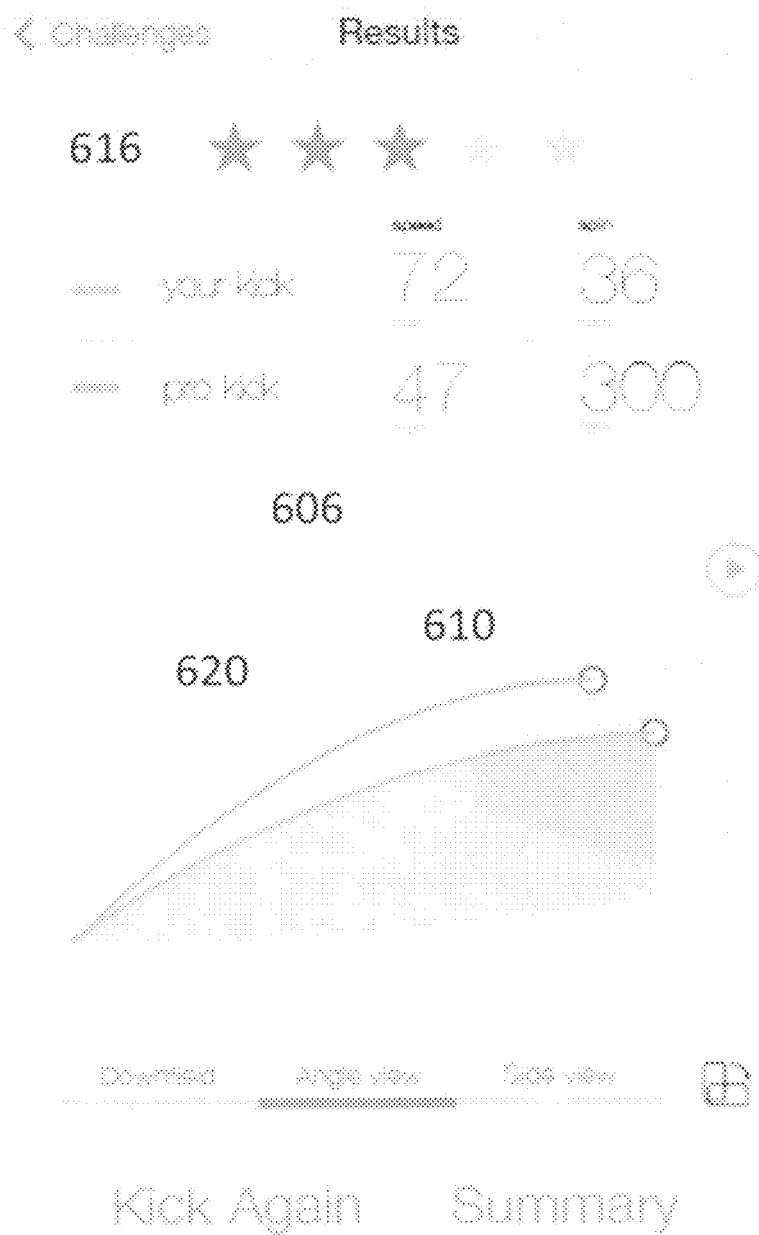
FIG. 45 is a graphical user interface for a sport ball motion monitoring application according to an embodiment of the present invention.

When a pro challenge sub-module is selected and executed by the portable electronic device 306 for the individual 10, a display of the portable electronic device 306 may provide the individual 10 with challenge the individual 10 to mimic the power, bend, flight trajectory, or other characteristics of a sample kick from a professional soccer player, such as via the exemplary GUI windows of FIGS. 44 and 45.

FIG. 44 is an exemplary GUI window illustrating features of the pro challenge sub-module. Initially, when a pro challenge sub-module is selected and executed by the portable electronic device 306 for the individual 10, display of the portable electronic device 306 may provide the individual 10 with GUIs and feedback similar to those described above. As with previously described embodiments, suitable videos, animations, and/or still images may be provided. In particular, videos, animations, and/or still images of a professional soccer player executing a specific kick or other maneuver, along with accompanying written or audio explanation, may be provided. Again, an accompanying video, animation, or still image may be provided for guidance, and they may incorporate references to locations of one or more exterior markings 202 of the soccer ball 106.

As shown in FIG. 41, a series of pro challenge icons 620 may be presented to the individual 10. A pro challenge icon 620 may include a starting location for a soccer ball 106 to be placed with respect to a goal, a target ball speed, a target ball spin rate, a target ball trajectory, and other suitable characteristics. For example, the first pro challenge icon 620 of FIG. 44 illustrates a challenge where the individual 10 is tasked with kicking a soccer ball 106 around forty-six miles per hours with about 120 revolutions per minute of spin over the top of a five person wall from just outside the middle of the penalty area. In some embodiments, a selection icon 604 may also be used to indicate which foot 12 the individual 10 is kicking with. Specific pro challenges may be associated with specific professional soccer players. In this case, videos, animations, and/or still images of the player may be shown to illustrate the kick, or written or audio explanation may be provided from the player.

In some embodiments, the pro challenge sub-module may present the individual 10 with a solo challenge. In other embodiments, the pro challenge sub-module can present the challenge to two or more individuals 10 so that they can compete against each other.

When the individual 10 is ready to begin the pro challenge, they may be presented with a prompt to tap a ball icon 602 when they are ready to monitor a kick using the motion monitoring system 100, similar to the display depicted in FIG. 24. In some embodiments, the GUIs displayed to provide feedback to the individual 10 for the pro challenge may be similar to those previously described with respect to FIGS. 25-28. In addition, when the individual 10 is engaged in a pro challenge, FIG. 45 is an exemplary GUI window that may be provided showing a visual display to the individual 10 giving them feedback about their ability to mimic the power, bend, flight trajectory, or other characteristics of a sample kick from a professional soccer player during their kicks.

The exemplary embodiment of FIG. 45 provides a visual display to the individual 10 giving them feedback about the motion characteristics of the soccer ball 106 during their kick, and how it compares to the professional's kick. The exemplary GUI includes a statistical display 606 that may provide, for example, information on the maximum speed of the soccer ball 106 during the post-kick flight or information on the maximum spin rate of the soccer ball 106 during the post-kick flight, as well as how these speed and spin numbers compare to any target numbers provided for the model professional kick. For example, in the illustrated embodiment, the targets for the professional model kick were forty-seven miles per hour and three hundred revolutions per minute, while the individual's 10 recorded kick was seventy-two miles per hour and thirty-six revolutions per minute.

FIG. 45 further illustrates a scorecard 616, which awards the individual 10 anywhere from one to five stars based on how closely they matched the model professional kick. In the illustrated embodiment, the individual 10 was awarded three stars.

The exemplary GUI of FIG. 25 also includes a video element 610. The exemplary video element 610 shown is an animation that represents the flight path of the kicked soccer ball 106 in three dimension, set upon the background of a representation of a soccer goal, as well as a an animation that represents the flight path of the model professional kick. In some embodiments the animation may start automatically, while in other embodiments the individual 10 must provide an input to the portable electronic device 306 to request that the video play. In one embodiment, the perspective of the animated flight path may change such that the individual's 10 perspective may appear to rotate around the animated flight path to provide a better perspective on the flight path. In another embodiment the individual 10 may be presented with a selection icon 604 allowing the individual 10 to choose different animated views of the kick and fight path such as, for example, a downfield view, an angled view, or a side view. The particular flight path shown and animated may be based partially or entirely on the determined motion characteristics of the soccer ball 106, such that the flight animated flight path is a realistic approximation of the actual flight path of the kicked soccer ball 106. In other embodiments, the individual 10 may be able to toggle the view between that of the flight path of the kicked soccer ball 106 and the flight path of the model professional kick.

FIG. 46 is an exemplary GUI window depicting a record book menu GUI that includes several icons or indicia corresponding to several different categories of "favorite" kicks, such as the individual's 10 most powerful kicks, their kicks with the most spin, and best knuckle balls. As previously described, at any point during regular use of the motion monitoring system 100 application, the individual 10 may designate a kick as a "favorite" kick after reviewing their feedback while viewing a display such as those of FIGS. 25-28 by providing a user input to portable electronic device 306, such as by tapping a "favorite" icon. The motion monitoring system 100 will then save a record of the kick being a favorite kick of the individual 10 in a memory device in one or more of the portable electronic device 306, or at a remote server 302.

Figure 47:
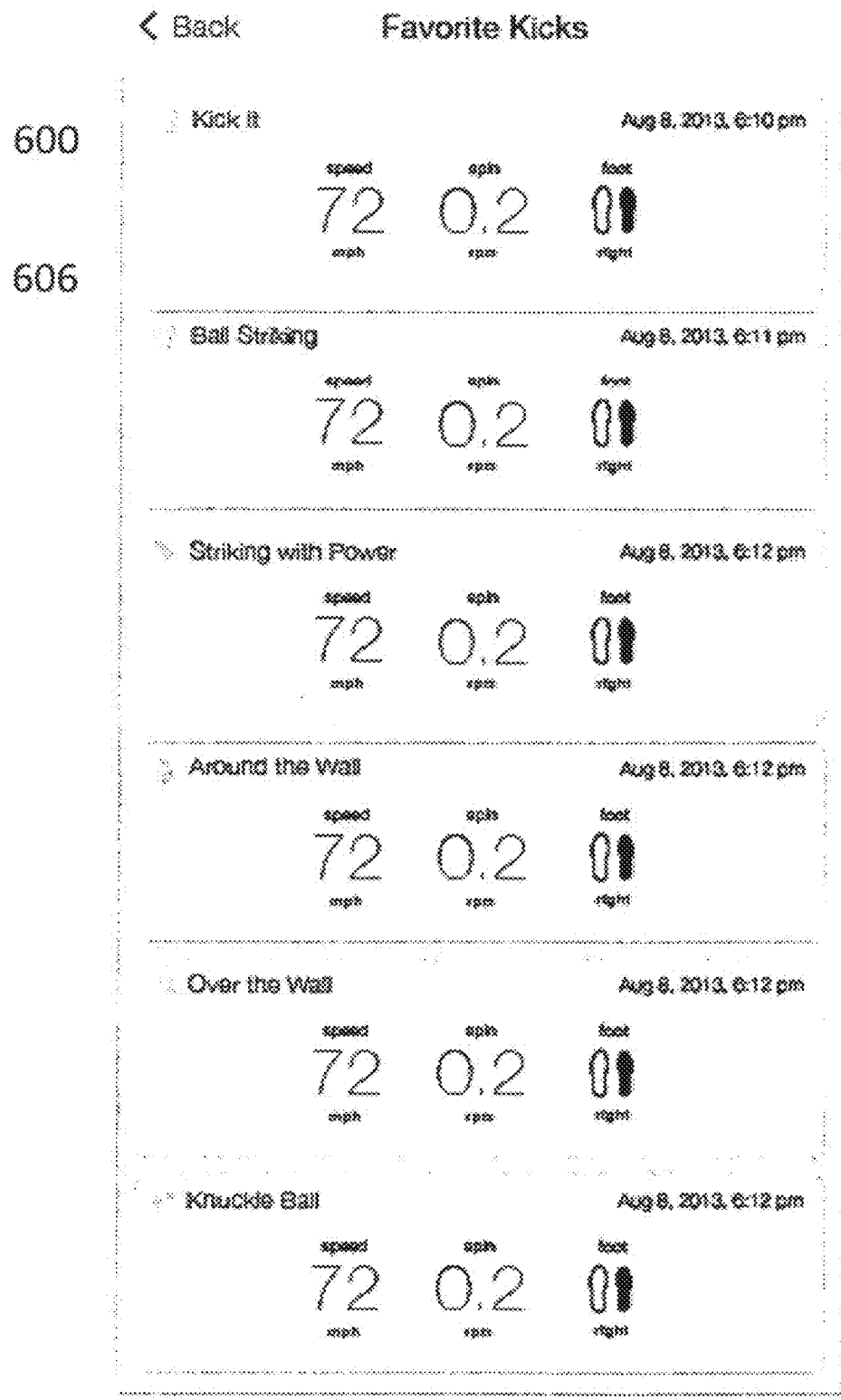
FIG. 47 is a graphical user interface for a sport ball motion monitoring application according to an embodiment of the present invention.

FIG. 47 is an exemplary GUI window showing a menu 600 of various saved favorite kicks for an individual 10. Each entry includes a statistical display 606 listing, for example, the speed of the kick, the spin for the kick, if the kick was associated with any particular drill or challenge, which foot 12 the individual 10 used for the kick, and the date and time of the kick. In one embodiment, selecting an entry for a kick may drill down to provide more detail about the kick, such as the information provided in FIGS. 25-28.

Figure 48:
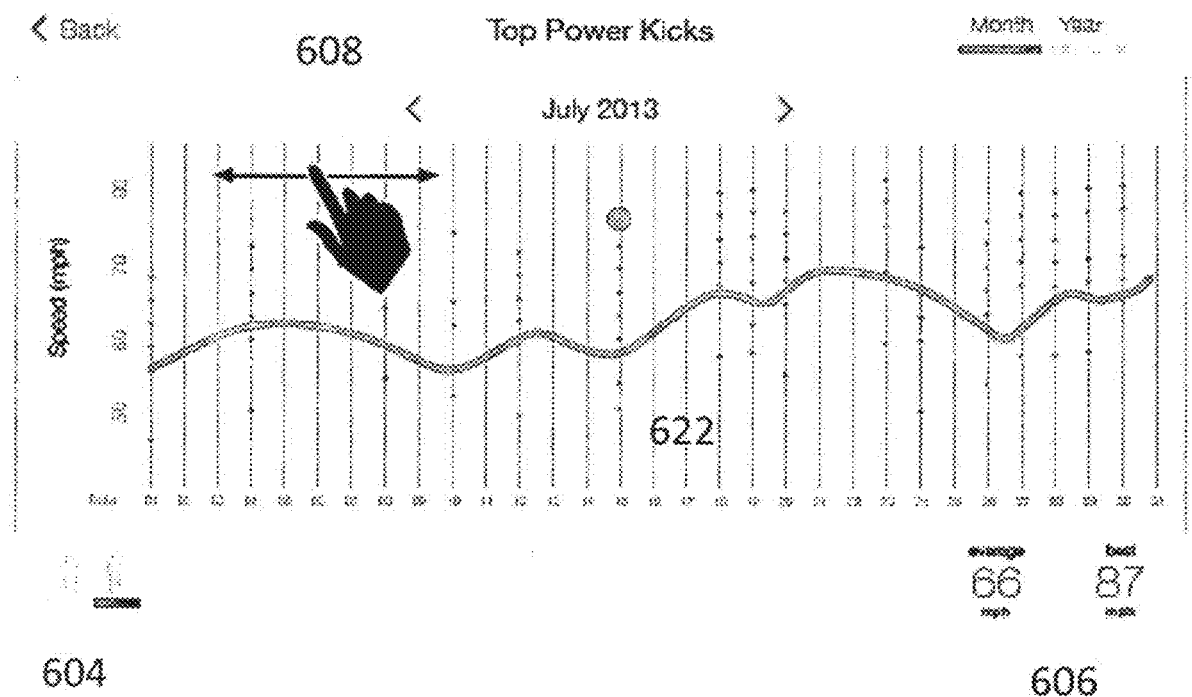
FIG. 48 is a graphical user interface for a sport ball motion monitoring application according to an embodiment of the present invention.

FIG. 48 is an exemplary GUI window showing a timeline 622 display. The timeline display 622 may provide an overview of the individual's 10 performance with the soccer ball 106 over a period of time. As illustrated in FIG. 48. The individual's 10 history of kick records may be displayed in association with the date that the kick was conducted. In some embodiments all kicks are included I the timeline, while in other embodiments only "favorited" kicks are included in the timeline. In some embodiments only a single category of kick data is plotted versus time, such as kick speed as shown in FIG. 48. In an embodiment, only a maximum number of kicks, such as ten, can be displayed for a given day if more than ten kicks were taken and record that day. For example, only the top ten best kicks may be saved.

The timeline display 622 may also include an average line plotting the running average for the plotted variable versus time. In addition, as shown in the bottom right hand corner of FIG. 48, the numerical average of speed and spin for the given time period may also be shown.

As with other embodiments discussed above, the timeline display 622 may include a swipe element 608 to allow the individual 10 to change the display. In some embodiments swiping may more the timeline display 622 forward or backward in time. In other embodiments swiping may toggle between the display of speed, spin, or other characteristics.

Figure 49:
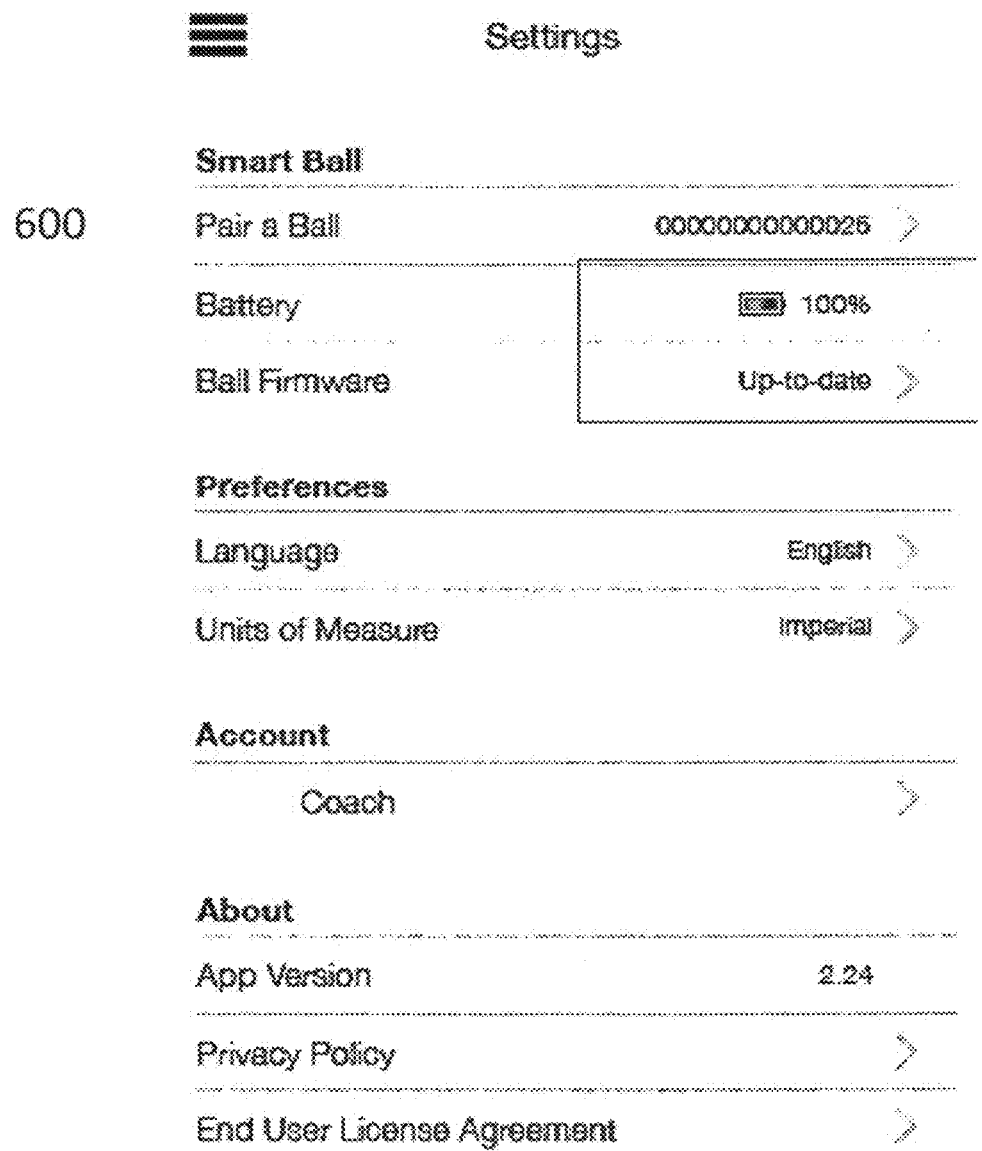
FIG. 49 is a graphical user interface for a sport ball motion monitoring application according to an embodiment of the present invention.

FIG. 49 is an exemplary GUI window depicting a setting screen for the motion monitoring system 100 applications. Settings may include indicators for the soccer ball 106 pairing status, soccer ball 106 serial number, the battery status for the soccer ball 106, information on the soccer ball's 106 firmware, language and measurement unit preferences, and whether the individual 10 has linked the application to other coaching or social media accounts. In an embodiment, any of the information or GUIs discussed herein can be uploaded and shared via social media platforms.

V. Additional Exemplary Embodiments

For ease of description, embodiments of the present invention are often described with reference to a sport ball 106, and in particular to a soccer ball 106. The disclosure herein, however, is applicable to sports objects (i.e., objects used for an athletic activity) that are balls, as described, and sports objects that are not balls, such as, for example a skateboard, a surfboard, a hockey stick, a hockey puck, a heart rate monitor, an arrow, a discus, a javelin, a bowling pin, munitions, a tennis racket, a golf club, a boomerang, and a kite. The disclosure herein, however, is also applicable to objects that are not sports objects, such as, for example, an aircraft (e.g., model plane).

In addition, embodiments of the present invention are often described with reference to a sensor module 102 including an acceleration sensor 118 and calculations based from acceleration sensor 118 readings. In other embodiments, however, the sensor module 102 may include other sensors, such as a magnetic field sensor 120 and/or an angular momentum sensor 124, instead of or in addition to the acceleration sensor 118, and calculations may be based off of one or more of acceleration sensor 118, magnetic field sensor 120, and/or an angular momentum sensor 124 readings.

In some embodiments of the present invention, the monitoring system 100 may also include or interact with an interactive retail system. The interactive retail system could be, for example, presented to an individual 10 via a screen on the individual's 10 portable electronic device 306. The interactive retail system could provide a platform for selecting and/or ordering products offered by the provider of the system. Based on the activity metric or specific athletic movement provided by the monitoring system 100, and/or based on any training or coaching provided, as described above, the interactive retail system could suggest specific products or product lines that may be helpful to the individual 10 in improving their future performance. In some embodiments, personal data about the individual 10 stored by the monitoring system 100 may also be used in making the determination of suitable products or product lines.

For example, a soccer player trying to improve her shots may receive a recommendation for a new pair of soccer cleats, while a basketball player trying to improve his jumping ability may receive a recommendation for a new pair of basketball shoes. These recommendations may ultimately be based on data derived from monitoring the individuals 10 body 106, and/or from monitoring the individual's 10 athletic equipment 108. For example, a source of inadequate performance may be the individual's 10 performance or it may be that the individual's 10 current equipment 108 has worn out. In some embodiments, the individual 10 may be provided with the option to purchase the new product at the time of receiving the any training or coaching provided.

In one embodiment, the activity metric or specific athletic movement data and/or any training or coaching provided may be used for the online customization of certain products. For example, this data can be used to customize an article of footwear, an article of compression clothing, a helmet, or other piece of clothing or athletic equipment to enable toe clothing or other equipment to help the individual 10 in improving their future performance. In some embodiments, customized products may have an unique styles, varied materials, or different accessories for the individual 10 to choose from.

In some embodiments, certain products or product lines may be "unlocked" for individuals 10 to purchase only after the individual 10 achieve certain milestones for performance or improvement such as certain levels of an activity metric or certain mastery of a specific athletic movement.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems.

Program products, methods, and systems for providing sport ball motion monitoring services of the present invention can include any software application executed by one or more computing devices. A computing device can be any type of computing device having one or more processors. For example, a computing device can be a workstation, mobile device (e.g., a mobile phone, personal digital assistant, tablet computer, or laptop), computer, server, compute cluster, server farm, game console, set-top box, kiosk, embedded system, a gym machine, a retail system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In an embodiment, the one or more processors can be part of a computing device incorporated in a clustered computing environment or server farm. Further, in an embodiment, the computing process performed by the clustered computing environment may be carried out across multiple processors located at the same or different locations.

Software of the present invention may be stored on any computer-usable medium.

Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the monitoring system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

What is claimed is:

1. A method for monitoring the motion of a sport ball that has been impacted by an individual during the course of an athletic activity, the method comprising:
    a mobile phone wirelessly receiving acceleration data from the sport ball;
    the mobile phone determining a rate of spin of the sport ball after the impact based on the acceleration data;
    the mobile phone determining a speed traveled by the sport ball after the impact based on the acceleration data, wherein determining the speed traveled by the sport ball comprises comparing the rate of spin of the sport ball after the impact to a predetermined threshold rate of spin; and
    the mobile phone determining a point of impact based on the speed traveled by the sport ball and the rate of spin of the sport ball, wherein the point of impact comprises a location on a surface of the sport ball where the impact occurred.

2. The method of claim 1, further comprising the mobile phone generating a graphical display, wherein the graphical display comprises an animation representing the flight path of the impacted sport ball.

3. The method of claim 1, further comprising the mobile phone generating a graphical display, wherein the graphical display comprises a graphical representation of the point of impact overlaid on top of an image of the sport ball.

4. The method of claim 1, further comprising the mobile phone determining the point of impact based on the acceleration data by conducting a regression analysis.

5. The method of claim 4, wherein the speed traveled by the sport ball and the rate of spin of the sport ball are variables in the regression analysis.

6. The method of claim 1, wherein the graphical display comprises feedback on how the result of the impact of the sport ball by the individual during the course of an athletic activity compares to a model result.

7. A method for monitoring the motion of a sport ball that has been impacted by an individual during the course of an athletic activity, the method comprising:
- a portable electronic device wirelessly receiving motion data from the sport ball;
- the portable electronic device determining a point of impact based on the motion data, wherein the point of impact comprises a location on a surface of the sport ball where the impact occurred; and
- the portable electronic device generating a graphical display, wherein the graphical display comprises a graphical representation of the point of impact overlaid on top of an image of the sport ball.

8. The method of claim 7, further comprising the portable electronic device determining the point of impact based on the motion data by conducting a regression analysis.

9. The method of claim 7, further comprising the portable electronic device determining a spin axis orientation for the sport ball after the impact based on the acceleration data.

10. The method of claim 7, further comprising the portable electronic device determining a launch angle for the sport ball after the impact based on the acceleration data.

11. The method of claim 10, further comprising the portable electronic device determining the point of impact based on a speed, spin rate, spin axis, and launch angle of the sport ball.

12. The method of claim 7, further comprising the portable electronic device determining a speed traveled by the sport ball after the impact based on the motion data.

13. The method of claim 12, further comprising the portable electronic device generating a graphical display, wherein the graphical display comprises an animation representing the flight path of the impacted sport ball.

14. The method of claim 13, wherein the graphical display comprises feedback on how the result of the impact of the sport ball by the individual during the course of an athletic activity compares to a model result.

15. The method of claim 7, wherein the portable electronic device is a mobile phone.

16. The method of claim 7, further comprising the portable electronic device recording a video that captures a result of the impact of the sport ball by the individual during the course of an athletic activity.

17. The method of claim 16, further comprising the portable electronic device correlating speeds traveled and rates of spin at a plurality of time periods to corresponding time periods of portions of the recorded video based on the plurality of time periods at which the speeds traveled and rates of spin occurred and at which the portions of the video were recorded.

* * * * *